US009302982B2

(12) United States Patent
Christian

(10) Patent No.: US 9,302,982 B2
(45) Date of Patent: *Apr. 5, 2016

(54) PHARMACEUTICAL DOPAMINE GLYCOCONJUGATE COMPOSITIONS AND METHODS OF THEIR PREPARATION AND USE

(75) Inventor: Samuel T. Christian, Alabaster, AL (US)

(73) Assignee: GLYCON LLC, Riverside, AL (US)

( * ) Notice: Subject to any disclaimer, the term of this patent is extended or adjusted under 35 U.S.C. 154(b) by 255 days.

This patent is subject to a terminal disclaimer.

(21) Appl. No.: 13/551,131

(22) Filed: Jul. 17, 2012

(65) Prior Publication Data

US 2013/0203855 A1 Aug. 8, 2013

Related U.S. Application Data

(63) Continuation-in-part of application No. 11/965,444, filed on Dec. 27, 2007, now Pat. No. 8,252,752, which is a continuation of application No. 10/625,645, filed on Jul. 22, 2003, now Pat. No. 7,345,031, application No. 13/551,131, which is a continuation-in-part of application No. 12/913,543, filed on Oct. 27, 2010, now Pat. No. 9,023,818, which is a continuation of application No. 11/343,266, filed on Jan. 30, 2006, now abandoned, which is a continuation of application No. 09/547,501, filed on Apr. 12, 2000, now abandoned.

(51) Int. Cl.

| *A61K 31/7008* | (2006.01) |
| *A61K 31/7032* | (2006.01) |
| *C07H 5/04* | (2006.01) |
| *C07H 15/18* | (2006.01) |
| *C07C 235/08* | (2006.01) |
| *A61K 47/48* | (2006.01) |
| *A61K 31/704* | (2006.01) |
| *C07H 17/00* | (2006.01) |

(52) U.S. Cl.
CPC .............. *C07C 235/08* (2013.01); *A61K 31/704* (2013.01); *A61K 47/48092* (2013.01); *C07H 5/04* (2013.01); *C07H 17/00* (2013.01)

(58) Field of Classification Search
CPC .. C07H 15/2013; C07H 5/06; A61K 31/7032; A61K 31/7008
See application file for complete search history.

(56) References Cited

U.S. PATENT DOCUMENTS

| 3,929,813 A | 12/1975 | Higuchi |
| 3,962,447 A | 6/1976 | Higuchi et al. |
| 4,032,676 A | 6/1977 | Heins et al. |
| 4,190,672 A | 2/1980 | Fahn |
| 5,380,837 A | 1/1995 | Nakada et al. |
| 5,639,737 A | 6/1997 | Rubin |
| 6,339,064 B1 | 1/2002 | McDevitt et al. |
| 6,548,484 B1 | 4/2003 | Christian |
| 7,345,031 B2* | 3/2008 | Christian ............ 514/62 |
| 8,252,752 B2* | 8/2012 | Christian ............ 514/42 |
| 9,023,818 B2 | 5/2015 | Christian |
| 2006/0189547 A1 | 8/2006 | Christian |

FOREIGN PATENT DOCUMENTS

| WO | 9728174 | 8/1997 |
| WO | 9905089 | 2/1999 |
| WO | 0197244 | 12/2001 |

OTHER PUBLICATIONS

Thomas et al., "Parkinson's Disease" Human Molecular Genetics (2007) vol. 16 rev iss 2, pp. R183-R194.*
Rao et al., "Parkinson's Disease:Diagnosis and Treatment" American Family Physician (2006) vol. 74 No. 2 pp. 2046-2054.*
"Remington: The Science and Practice of Pharmacy, 20$^{th}$ edition", Edited by Alfonso R. Gennaro, published 2000 by Lippincott Williams and Wilkins, pp. 218, 780-786, and 858-863.*
Czarnocki et al., "Enantioselective Synthesis of (R)-(−) Laudanosine and (R)-(−) Glaucine from L-Ascorbic Acid", Tetrahedron: Asymmetry, vol. 7, No. 9, Sep. 1996, pp. 2711-2720.
Doherty, "The Synthesis of Glyconyl Peptides", Journal of Biological Chemistry, vol. 201(2), May 1953, pp. 857-866.
Fernandez et al., "Synthesis and biological studies of glycosyl dopamine deriviatives", Carbohyd. Res. vol. 327, 2000, pp. 353-365.
Glinsky et al., "Inhibition of colony formation in agarose of metastatic human breast carcinoma and melanoma cells by synthetic glycoamine analogs", Clin. Exp. Metastasis, vol. 14(3), May 1996, pp. 253-267.
Haavik et al., "Tyrosine hydroxylase and Parkinson's disease", Molecular Neurobiology, vol. 16, No. 3, Jun. 1998, pp. 285-309.
Jakas et al., "Synthesis and 13C NMR investigation of novel Amadori compounds (1-amino-1-deoxy-D-fructose derivatives) related to the opioid peptide, leucine—enkephalin", J. Chem. Soc., Perkin Trans., vol. 2, DOI: 10.1039/P29960000789, 1996, pp. 789-794.
Jiang et al., "Dopaminergic properties and experimental anti-Parkinsonian effects . . . ", Clin. Neuropharmacol vol. 27, No. 2, 2004, 63-73.
Knoerzer et al., "Dopaminergic Benzo[a]phenanthridines: Resolution and Pharmacological Evaluation of the Enantiomers of Dihydrexidine, the Full Efficacy D1 Dopamine Receptor Agonist", Journal of Medicinal Chemistry, vol. 37 No. 15, Jul. 1994, pp. 2453-2460.
Likhoshersfov et al., "Giycoconjugates of amines: alkylation of primary and secondary amines", Russ. Chem. Bull. vol. 47, No. 6, 1998, pp. 1214-1217.
Likhoshersfov et al., "Synthesis of N-chloroacetyi-B-glycopyranosylamines, derivatives of monosaccharides and lactose.", Russ. Chem. Bl.vol: 45, 1996, pp. 1760-1763.
Maher et al., "Substrate specificity and kinetic parameters of GLUT3", Biochem. J. vol. 315, 1996, pp. 827-831.

(Continued)

*Primary Examiner* — Eric Olson
(74) *Attorney, Agent, or Firm* — Kilpatrick Townsend & Stockton LLP

(57) ABSTRACT

Hydrophilic transportable N-linked glycosyl dopaminergic prodrug compounds and methods of their use.

9 Claims, 22 Drawing Sheets

(56) References Cited

OTHER PUBLICATIONS

Meiergerd et al., "Striatal Transporter for Dopamine: Catechol Structure-Activity Studies and Susceptibility to Chemical Modification", J. Neurochem. vol. 62, No. 3, 1994, pp. 998-1008.

Mizuma et al., "Comparative Study of Active Absorption by the Intestine and Disposition of Anomers of Sugar-Conjugated Compounds", Biochemical Pharmacology. vol. 45 (7), Apr. 1993, pp. 1520-1523.

Mizuma et al., "Intestinal Active Absorption of Sugar-Conjugated Compounds by Glucose Transport System: Implications for Improvement of Poorly Absorbable Drugs", Biochemical Pharmacology, vol. 43, Issue 9, May 1992, pp. 2037-2039.

Mizuma et al., "The Beta-Anomeric and Glucose Preferences of Glucose Transport Carrier for Intestinal Active Absorption of Monosaccharide Conjugates", Biochimica et Biophysica Acta (BBA), vol. 1200 (2), Jul. 1994, pp. 117-122.

Ohnishi et al., "Blood-brain barrier transport of L-tyrosine Conjugates: a model study for the brain targeting using large neutral amino acid transport system", J Drug Target.; vol. 8(6);, 2000, pp. 395-401.

Ovalle et al., "Systematic analysis of oxidative degradation", Carbohyd. Res. vol. 330, 2001, pp. 131-139.

Roper et al., "NMR spectroscopy of N-(1-deoxy-D-fructos-1-YL)-L-amino acids ("fructose-amino acids")", Carbohydrate Research vol. 116, Issue 2, http://dx.doi.org/10.1016/0008-6215(83)88108-7, Jun. 1, 1983, pp. 183-195.

Shukla et al., "Effect of desoxy-fructose derivatives of dopa and dopamine on body temperature", Archly fur Arzneitherapie; vol. 5(1 ),, 1981, pp. 183-195.

Starkstein et al., Journal of Neurology, Neurosurgery, and Psychiatry, British Medical Association, vol. 61,, 1996, pp. 381-387.

Takata et al., "Transport of glucose across the blood-tissue barriers", Int. Rev. Cytology vol. 172, 1997, pp. 1-53.

Tamai et al., "Transporter-mediated permeation of drugs across the blood-brain barrier", Journal of Pharmaceutical Sciences vol. 89 issue 11, Nov. 2000, pp. 1371-1388.

Tarjanyi et al., "Chromatographic Investigation and Computer Simulation of Deprenyl Metabolism", New Approaches in Chromatography, 1993, pp. 243-260.

Tarjanyi et al., "Chromatographic Investigation and Computer Simulation of L-deprenyl Metabolism.", European Journal of Drug Metabolism and Pharmacokinetics, vol. 23 (2), Jun. 1998, pp. 324-328.

Vannucci et al., "Glucose transporter expression in brain: Relationship to cerebral glucose utilization", Dev. Neurosci. vol. 20 (4-5), 1998, pp. 369-379.

Walling et al., Journal of Neuroscience Research, Wiley-Liss, vol. 54, 1998, pp. 301-308.

Wooley et al., "Synthesis of Derivatives of 1,2-Dichloro-4-Benzenesulfonamido-5-Nitrobenzene and Their Use in the Chemotherapy of Spontaneous Cancers" Canadian Journal of Chemistry, vol. 43, pp. 1454-1459.

Wunder et al., "Enhanced Albumin Uptake by Rat Tumors.", International Journal of Oncology, vol. 11 (3), Sep. 1997, pp. 497-507.

"Caplus Abstract: Doherty, D. "The synthesis of glyconyl peptides", J. Biol. Chem. (1953) vol. 201, pp. 857-866".

U.S. Appl. No. 09/547,501, "Office Action", mailed Jul. 29, 2005, 15 Pages.

U.S. Appl. No. 09/547,501 , "Office Action", mailed Feb. 26, 2004, 9 Pages.

U.S. Appl. No. 09/547,501, "OfficeAction", mated Jul. 1, 2003, 9 Pages.

U.S. Appl. No. 10/625,645, "Notice of Allowance", mailed Jul. 25, 2007, 5 Pages.

U.S. Appl. No. 10/625,645 , "Notice of Allowance", mated Sep. 28, 2007, 8 Pages.

U.S. Appl. No. 10/625,645, "Office Action", mated Nov. 16, 2006, 13 Pages.

U.S. Appl. No. 11/343,266, "Office Action", mailed Apr. 27, 2010, 13 Pages.

U.S. Appl. No. 11/965,444, "Notice of Allowance", mated Apr. 3, 2012, 6 Pages.

U.S. Appl. No. 11/965,444, "Office Action", mated Feb. 2, 2011, 18 Pages.

U.S. Appl. No. 11/965,444, "Office Action", mailed Sep. 28, 2011, 9 Pages.

U.S. Appl. No. 12/913,543, "Notice of Allowance", Jul. 29, 2014, 10 pages.

U.S. Appl. No. 12/913,543, "Notice of Allowance", Mar. 13, 2015, 10 pages.

U.S. Appl. No. 12/913,543, "Notice of Allowance", Jan. 10, 2014, 12 pages.

U.S. Appl. No. 12/913,543, "Office Action", Jan. 30, 2013, 44 Pages.

\* cited by examiner

Rota-rod Test with IPX-750 (20mg/kg)/0.9% NaCl in heterozygous/WT Mice

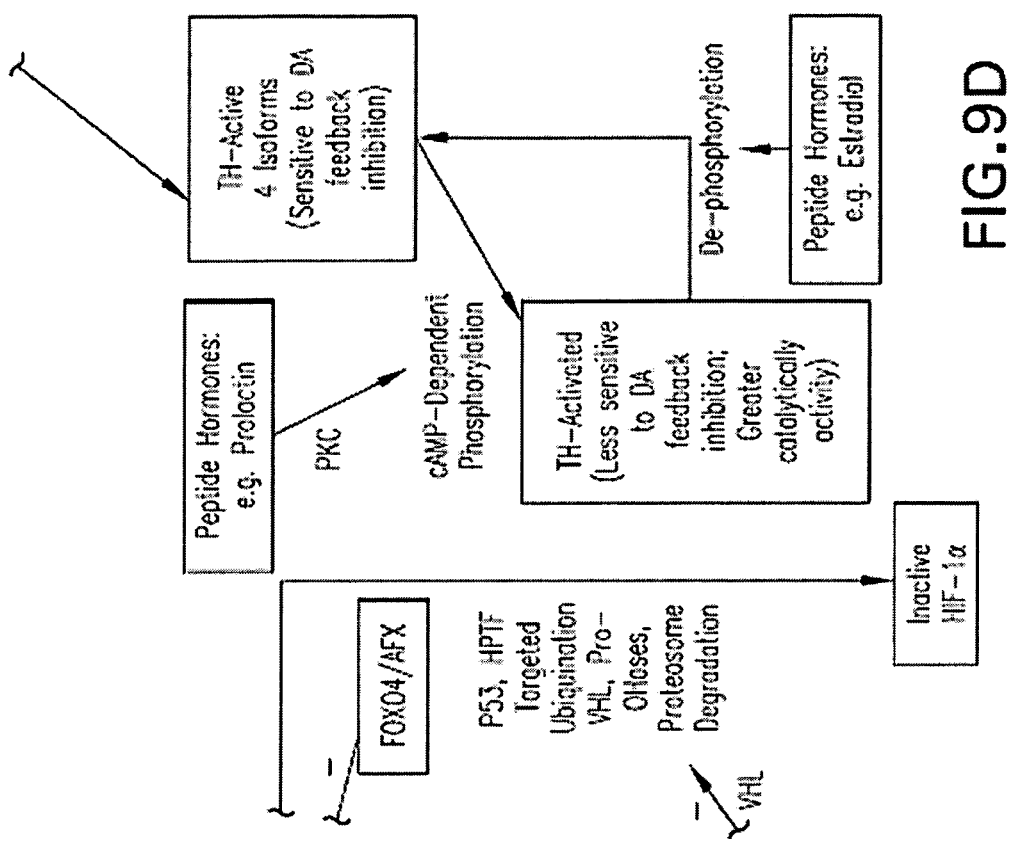

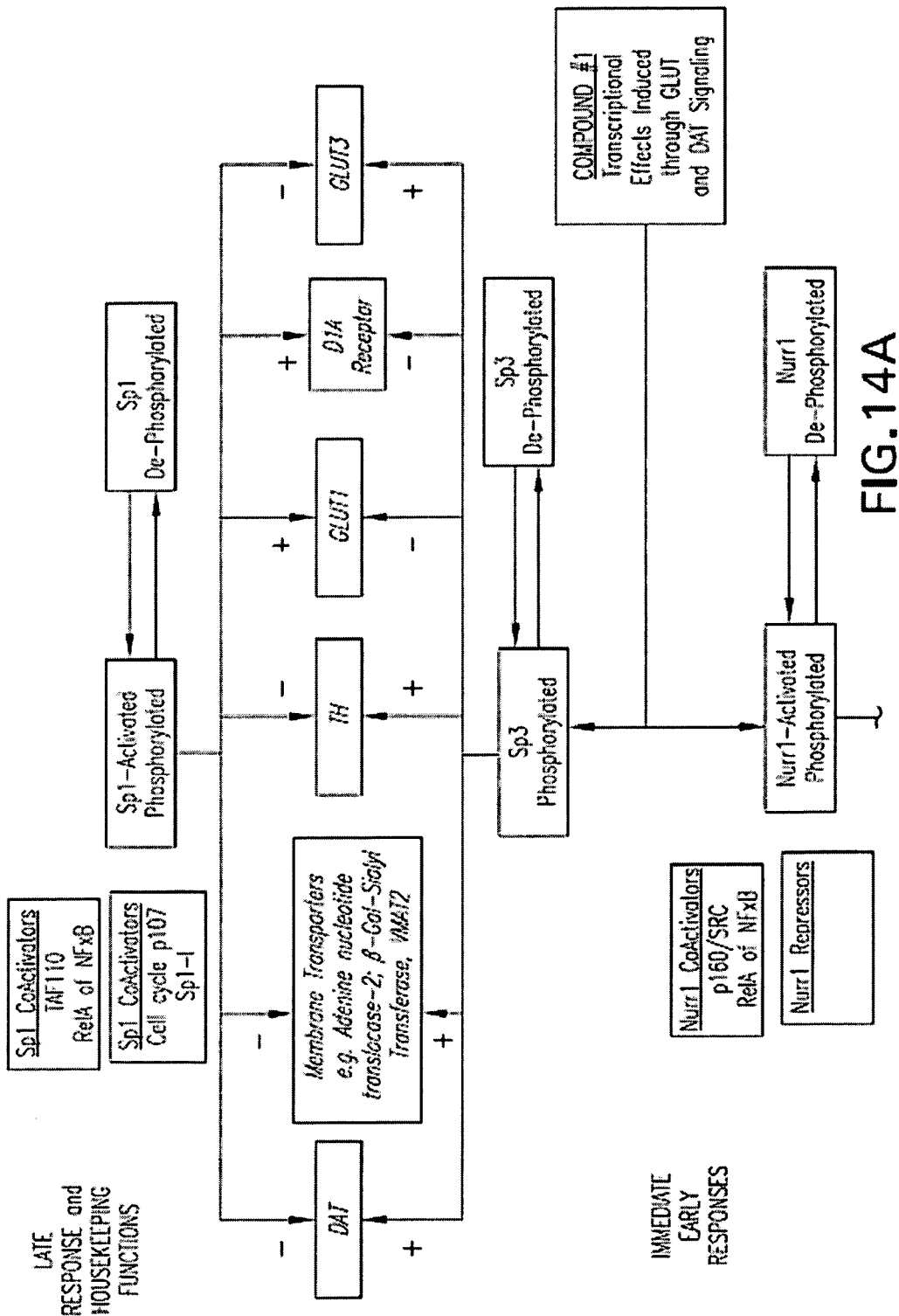

PHARMACEUTICAL DOPAMINE GLYCOCONJUGATE COMPOSITIONS AND METHODS OF THEIR PREPARATION AND USE

PRIOR RELATED APPLICATIONS

The present application is a continuation-in-part of U.S. patent application Ser. No. 11/965,444, filed Dec. 27, 2007, which issued as U.S. Pat. No. 8,252,752 on Aug. 28, 2012, which is a continuation of U.S. patent application Ser. No. 10/625,645, filed Jul. 22, 2003, which issued as U.S. Pat. No. 7,345,031 on Mar. 18, 2008. The present application is a continuation-in-part of U.S. patent application Ser. No. 12/913,543, filed Oct. 27, 2010, now U.S. Pat. No. 9,023,818 which is a continuation of U.S. patent application Ser. No. 11/343,266, filed Jan. 30, 2006, which is abandoned and is a continuation of U.S. patent application Ser. No. 09/547,501, filed Apr. 12, 2000, which is abandoned. The foregoing patents and patent applications are incorporated herein by reference in their entirety.

FIELD OF THE INVENTION

The invention relates generally to dopaminergic compositions and methods of their preparation and use for treating neurological diseases including Parkinson's and related diseases.

BACKGROUND OF THE INVENTION

Parkinson's disease reportedly affects one person in fifty over fifty years of age and one in twenty over seventy. A degenerative disease of the nervous system described in 1817 and characterized by progressive loss of nigrostriatal neurons, a shaking palsy with tremor at rest, muscular rigidity and slowness of movement, the possible etiology, the cell biology, biochemistry and pathophysiology are still areas of intense speculation and ongoing research. Diseases related by clinical symptomology, and progressive clinical symptomology in Parkinson's patients, including post-encephalitic syndromes, Wilson's disease, Parkinsonism secondary to cerebrovascular trauma and stroke, dementia, Alzheimer's disease, Lou Gehrig's disease, psychomotor retardation, certain schizophreniform behavior, anxiety and depression. The primary biochemical defect in Parkinson's disease is loss of nigrostriatal dopamine synthesis.

Catecholamines including dopamine, norepinephrine and epinephrine are produced by chromaffin cells in the adrenal medulla responding as a specialized ganglion to sympathetic enervation from preganglionic fibers of the splanchic nerve. However, catecholamines do not cross the blood-brain barrier, hence, the need for synthesis within the CNS. L-Dope, the precursor of dopamine, readily crosses the blood-brain barrier but is unstable and rapidly inactivated in blood. Levodopa (a precursor of dopamine) and its derivatives are used for treatments of Parkinson's disease. Dopamine administered intravenously, while not crossing the blood brain barrier, binds D1-like and D2-like dopamine receptors in the periphery and is reportedly useful in certain treatments for peripheral defects such as congestive heart failure and hypertension (e.g., Kuchel, 1999).

Pharmaceutical compositions for treatments of Parkinsonism include: Levodopa (e.g., U.S. Pat. No. 3,253,023, U.S. Pat. No. 3,405,159), Carbidopa (e.g., U.S. Pat. No. 3,462,536), aminoindans (e.g., U.S. Pat. No. 5,891,923), benzhydrylamines (e.g., Diphenhydramine, U.S. Pat. No. 2,427,878); benzenemethanamines (e.g., U.S. Pat. No. 2,599,000; U.S. Pat. No. 5,190,965), piperidines (e.g., Budipine, U.S. Pat. No. 4,016,280; Biperiden, U.S. Pat. No. 2,789,110; Trihexylphenidyl, U.S. Pat. No. 2,682,543), pyrrolidines (e.g., Procyclidine, U.S. Pat. No. 2,891,890), tropines (e.g., Benztropine, U.S. Pat. No. 2,595,405; Hyoscyamine, Fodor et al. 1961), criptines (e.g., Bromocriptine, U.S. Pat. No. 3,752,814) and ergolines (e.g. Pergolide, U.S. Pat. No. 4,166,182).

Metabolic replacement therapy compounds that are endogenously converted to dopamine, e.g., Levodopa, results in stimulation of both D1-like and D2-like dopaminergic families of receptors. While agonists are theoretically superior to Levodopa (i.e., because they should not be dependent on enzymatic conversion), in clinical use they have been shown to lack the therapeutic potency of Levodopa. Direct acting D2 agonists (e.g., bromocriptine, lisuride and pergolide) have shown limited efficacy in monotherapy and are primarily used as add-on therapy to L-Dopa. Recent identification of novel structural classes of D1-selective isochroman dopamine agonists has led to renewed interest in possible use of D1 selective agonists in treatments for Parkinson's and other neurological diseases. However, any interest in dopaminergic agonists has recently been tempered by reports that direct neural injections of dopamine may be toxic to certain neurons (e.g. Rabinovic et al.; Luo et al.); possibly by overloading nascent vesicular monoamine transporters (e.g. Reveron et al.) and inducing apoptosis (e.g. Hou at al.; Panet et al.; Weingarten et al.) through postulated formation of toxic dopamine oxidative metabolites (e.g., Daily et al.) that might be transportable by a dopamine transporter (DAT; Xia et al.).

L-dopa, Levodopa, Cardiodopa (an inhibitor of dopa decarboxylase), Deprenyl (inhibiting dopamine degrading monoamine oxidase), Sinemet (a controlled release form of Levodopa) and their combinations and derivatives suffer from many major disadvantages. Commonly these agents have poor aqueous solubility and relatively short half-lives. Observed side effects accompanying chronic use include motor fluctuation, dysfunctions, peak-dose dyskinesia, requirements for frequent dosing involuntary movements, psychosis, confusion, visual hallucinations, bradykinesia, rigidity, tremors, gastrointestinal and gentiourinary dyantonomia, hypotension and cognitive decline (Hurtig, 1997). Often after 3-5 years of treatment patients develop complex dose-related unpredictable response fluctuations usually leading to a progressive decrease in therapeutic efficacy and also possible onset of serious side effects such as abnormal involuntary movements, end-of-dose deterioration and abrupt near instantaneous on-off changes in patient disability. "Adaptation" by neural tissues to chronic administration is complex, and may include down-regulation of dopamine receptor expression as well as metabolic changes in post-striatal neurons. In certain patients dyskinesia and response fluctuations would desirably be controlled by continuous intravenous infusion of drug at a constant level, however, because of the low aqueous solubility of Levodopa this is not a feasible solution. In addition to these neurologic disadvantages, metabolism of oral dope compounds to dopamine in the stomach and gastrointestinal tract (even in the presence of decarboxylase inhibitors) can often lead to unwanted side effects including severe nausea and hypotension. Levodopa methyl and ethyl esters given orally suffer many of these same problems. Thus, all current therapies suffer from serious side effects, bioavailability problems, or both, and there has been a long-felt need for improved pharmaceutically active agents for metabolic replacement therapy in Parkinson's and related diseases (Hurtig, 1997). There has also been a long-standing need for improved dopaminergic catechol agonists with improved bioavailability and penetrability of myelinated nerves, i.e., for peripheral use in treatments of e.g. hypertension and congenital heart diseases.

Molecular cloning studies have identified several genes encoding dopamine receptors. D1-like receptors, (recognized pharmacologically by the SCH23390 agonist), activate adenylate cyclase resulting in increased intracellular cAMP. Two gene products have been identified, i.e., D1A and D1B. D1B may have been previously identified pharmacologically as D5 and may be responsible for SCH23390 specific agonist activity. D2-like dopamine receptors, (recognized pharmacologically by spiperone and sulpride agonists), appear to be encoded by three genes with multiple possible splice variants expressed in different brain regions, i.e., D2S, D2L, D3 and D4. D2-like receptors do not appear adenylate cyclase-linked and may decrease intercellular cAMP levels, perhaps a result of kinase-mediated phosphorylation. D2-like receptors have been identified as a potential target for development of antipsychotic agents and treatments for schizophrenia, i.e., based on antipsychotic effects of chlorpromazine occurring with resultant drug-induced Parkinson's symptoms and increased risk of tardive dyskinesia. Schizophrenia is (at present) believed to result from hyperactive dopaminergic transmission in the mesolimbic region of the brain. While antipsychotic drugs with fewer side-effects have been developed (e.g., haloperidol, fluphenazine, clozapine, olanzapine, risperidone), to date, no consensus antipsychotic dopaminergic antagonist pharmacologic or receptor profile has emerged and approaches under active consideration include: (i) combination approaches for blockade of D2-like and D1-like receptors as well as $5-HT_2$ and $\alpha_1$ adrenergic receptors; (ii) selective approaches for blocking D2 subtypes, e.g., D3 and/or D4 or D2L/S and D4; and (iii) attempts to develop partial agonists to compete with dopamine binding.

In pharmacologic studies conducted over the past 20 years, the results seem to suggest relatively stringent structural requirements for activation of the D1 receptors, particularly in regard to any nitrogen atoms present in the compound (e.g., see Seller et al., 1991; Berger et al., 1989; Brewster et al., 1990; Kaiser et al., 1982; Dandridge et. al., 1984; Brewster et al. 1990; Weinstock et al., 1985; Riggs et al.; Seiler et al., 1982; Shah et al., 1996; Knoerzer et al., 1994). In addition, the nature of the terminal group (i.e., amino), or presence or length of an n-alkyl chain (Iorio et. al, 1986) may reportedly influence binding interactions at D1 sites. Based on experience with different pharmacophores, several receptor models have been proposed (Seiler and Markstein, 1989; Petersson et. al., 1990; Brewster et. al., 1990; Knoerzer et. al., 1994; Snyder et. al., 1995; Minor et. al., 1994). By comparison, pharmacologic studies of D2-like receptors suggest somewhat less rigid overall structural requirements, but also restrictions around any nitrogen atoms (e.g., see McDermed et al. 1979; Freeman and McDermed, 1982.; Liljefors et al., 1986; van de Waterbeemd et al., 1987).

The $Na^+/Cl^-$ dependent dopamine transporter, DAT1, granule system mediates calcium-dependent outward dopamine release into the synaptic cleft and inward energy-dependent dopamine vesicular re-uptake into the cytoplasm of presynaptic neurons. Loading of biosynthetic dopamine into granules is effected by the vesicular monoamine transporter (VMAT2; reviewed in Miller et. al., 1999). DAT may also control movements of other monoamines in brain tissues. Cocaine, amphetamines, phencyclidine and certain anti-depressants and uptake inhibitors interfere with dopamine transport by DAT (e.g., see Jones at al, 1999; Giros et. al., 1992). DAT function may be regulated by steroid hormones, has second order dependence on $Na^+$ (Earles et. al, 1999) and may be coupled (or uncoupled) to modulatory second messenger systems, (e.g., down-regulation of DAT accompanying activation of protein kinase C by phorbol esters), and ionic currents (Melikian et al., 1999; reviewed in Figlewicz, 1999). Radiotracer imaging methods have been used to localize DAT (e.g., within the nucleus accumbens and mid-brain regions) and D1 and D2 receptors (e.g., in nigrostrial pathways) in the brains of normal subjects, as well as in patients with Parkinson's disease and neuropsychiatric diseases such as schizophrenia (reviewed in Verhoeff 1999). Structure activity studies of antagonists have suggested that: (i) the DAT transporter may be sensitive to N-substitution (Choi et al., 2000); (ii) N-phenyl-substituted analogues may inhibit transport (Prakash et al., 1999; Husbands, et al., 1999); (iii) certain energetically unfavored boat conformations of rings may have high affinity for DAT (Prakash at al, 1999); (iv) structural rearrangement of the DAT protein may occur and be required for inward transport (Chen et al., 2000); (v) the DAT protein contains an endogenous $Zn^{2+}$ binding site (Loland et al., 1999); (vi) DAT transporter function is sensitive to aromatic substitutions (Husbands, et al., 1999); and, (vii) apparent ordered kinetics for DAT transporter function is $Na^+$ binding first, then dopamine and then $Cl^-$.

Several tissue enzyme systems exist for altering catecholamines, including dopamine. Monoamine oxidases, MAO-A in neural tissues and MAO-B in other tissues including stomach and intestine, are oxioreductases that deaminate dopamine and other catecholamines with preferential activity manifest for 2-phenylethylamine and benzylamine. Catechol-O-methyltransferase is a cytosolic enzyme that catalyzes addition of a methyl group, usually at the 3 position of a benzyl ring. O-methoxylated derivatives may be further modified by conjugation with glucuronic acid. Non-neuronal dopamine transporter uptake mechanisms may also exist, e.g., in kidney (Sugamori et. al., 1999).

Oral delivery of drugs constitutes special chemical challenges, i.e., general simultaneous requirements for intestinal penetration, blood borne delivery, blood-brain-barrier penetrability and maintenance of functional (receptor binding and/or metabolic) utility. CNS active drugs constitute yet additional special and challenging problems, i.e., low pH stability (or protection) and intestinal transport. Intestinal intracellular transport mechanisms for amino acids, vitamins and sugars are varied. Glucose transport has recently been reviewed (Takata et. al, 1997). Transport mechanisms for glucose include intestinal transport vesicles and $Na^+$/glucose co-transporters (SGLTs), i.e., driving active transport of glucose and galactose across the intestinal brush border by harnessing $Na^+$ gradients across the cell membrane. Net rates of vesicle transport and exocytosis have been estimated to be in the range of 10 thousand to 1 million per second (Wright et. al, 1997). Missense mutations in SGLT1 reportedly result in potentially lethal inability to transport glucose and galactose (Martin et. al, 1996). Certain sugar specificity's, structural requirements and capabilities of $Na^+$-dependent glucose transport carriers have been investigated with impure receptor membrane preparations, and/or mixtures of receptors, with the findings that the glucosyl transporter in human erythrocytes (i.e., GLUT1): (i) seems to require that the ring oxygen atoms at positions C1, C3, C4, and possibly C6, be capable of forming hydrogen bonds with the transporter protein, and (ii) a hydrophobic group at C5 may increase affinity for the transporter (Barnett et al., 1973). Intestinal glucose transporter mechanisms reportedly prefer: (i) β-anomers to α-anomers; (ii) β-D-glucose to β-D-galactose; and, (iii) β-glucoside>α-glucoside>β-galactoside>α-galactoside. The α-anomers of glucose and galactose were reportedly hydrolyzed to their aglycone constituents during a non-$Na^+$-dependent desglucosylation transport (Mizuma et. al., 1992, 1993, 1994). Apparently unrelated studies of antiviral glycosides have reportedly found that: (i) C1 phenyl-substituted glycosides and para-substituted butyl-phenyl derivatives may inhibit glucose transporters (Arita et. al, 1980); (ii) C1 O-acyl glycoside derivatives with alkyl chains or carbonyl groups (as an aglycone substituent) may act as non-penetrating inhibitors of glucose transport (Ramaswamy et. al., 1976); and (iii) 1-5-anhydroglucitol and 6-deoxyglucose may be transportable (Alvarado et. al., 1960). Thus, like dopaminergic receptor binding, the art suggests that special chemical structural requirements may exist for intestinal transport.

Unlike intestinal transport, neural glucose transport at the blood brain barrier appears to be mediated: (i) by endothelial cells and a sodium-independent facilitative transporter known as GLUT1 (Kumagai et. al., 1999); and (ii) at neuronal cells by GLUT3 (Vannucci, S J. et. al., 1998). GLUT1 also a predominant glucose transporter expressed in human erythrocytes. Neural tissue is almost entirely dependent on glucose transport for normal metabolic activity because tissue stores of glucose are low (relative to demand). Thus, current understanding suggest that GLUT1/3 competitive agents might have undesirable side effects. Specificity of neural GLUT1/3 is an area of active current investigation.

In mammals, glucuronidation of drug metabolites is common, e.g., involving the hepatic glucuronostransferase system and enzyme systems in kidney and intestine. Catecholamine glucuronidation is reportedly an important metabolic pathway in the rat and dopamine glucuronides we reportedly identified in rat cerebrospinal fluid (Wang et. al., 1983). Many drugs investigated for dopaminergic agonists and antagonist properties are reportedly metabolized and/or excreted as glucuronides, e.g., SCH23390 (a Schering prototype D1 receptor antagonist; Barnett, et. al., 1992), CGS15873 (a Ciba-Geigy dopamine agonist; Leal et. al., 1992), Carmoxirole (a Merck dopamine agonist; Meyer et. al., 1992), Olanzapine (a Lilly dopaminergic compound; Mattiuz et. al. 1997) and CP-93, 393 (a Pfizer anxiolytic drug candidate; Prakash et. al., 1998). Within this general class of cyclic Parkinson's drugs, several investigators have suggested glucuronidation as one common mechanism for targeting removal of phenolic drugs by urinary and biliary excretion, e.g., Mico et al., 1986 (indolone agonists); Gerding et. al., 1990 (N-0437, a tetralin agonist); Wang et. al., 1983 (catecholamines); Green et. al., 1996 (hydroxylated and carboxylated phenolic compounds); Poochiari et. al., 1986 (Ibopamine); Claustre et. al., 1990 and Alexander et. al, 1984 (dopamine). Shindo et. al., 1973 reportedly studied absorption of L- and D-dopa in vitro in ligated rat intestinal loops and found active transport and metabolism to dopamine glucuronides.

The blood brain barrier effectively limits neuraxial delivery of many pharmaceutically active compounds, including dopamine. Approaches disclosed for delivering drugs to the brain include lipophilic additions and modifications of hydrophilic drugs, (e.g., N-methylpyridinium-2-carbaldoxime chloride; 2-PA; U.S. Pat. Nos. 3,929,813 and 3,962,447; Bodor et. al, 1976, 1978 and 1981); linkage of prodrugs to biologically active compounds, (e.g., phenylethylamine coupled to nicotinic acid and modified to form N-methylnicotinic acid esters and amides; Bodor et. al., 1981 and 1983; PCT/US83/00725; U.S. Pat. No. 4,540,564); derivatization to centrally acting amines (e.g., dihydropyridinium quaternary amine derivatives; PCT/US85/00236); and enclosing compounds in cyclodextrin complexes (e.g., Yaksh et. al, U.S. Pat. No. 5,180,716).

Neuraxial delivery of many cyclic and heterocyclic compounds is problematic. Objects of the invention provide new classes of CNS-active compounds which circumvent problems of low aqueous solubility of dopaminergic compounds and the varied transport, receptor binding and stability problems encountered with dopaminergic drugs, including their relatively poor blood-brain barrier penetrability.

SUMMARY OF THE INVENTION

Hydrophilic transportable N-linked glycosyl dopaminergic prodrug compounds, their methods of preparation and uses are disclosed. The compounds are described by the general structure of FORMULA I, "A-B-D-E"                                                Formula I wherein: each of "—" constitutes a single bond; the "A"-moiety constitutes a dopaminergic cyclic radical; the "B"-moiety constitutes a "bridging" alkyl moiety; the "D"-moiety constitutes a nitrogen "linker"; and, the "E"-moiety constitutes a saccharide as set forth further below, e.g., a mono-, di-, tri- or oligosaccharide. Preferred compounds thus configured are: (i) ligands for a dopaminergic receptor; (ii) transportable in an intact form by an intestinal saccharide transporter system; (iii) transportable in an intact form by an endothelial blood brain barrier saccharide transporter system; (iv) transportable by neural dopamine transporters; and (v) metabolizable to provide a metabolic replacement therapy.

BRIEF DESCRIPTION OF THE FIGURES

In FIG. 9-12, positive (+) signs associated with arrows depict that the factor at the beginning of the arrow increases expression or activity of the factor at the arrow head; negative (−) signs depict that the indicated factor decreases expression or activity; and, all indicated activities are as they would occur in wild-type neural cells in the *substantia nigra*.

FIG. 10 schematically depicts the disclosed regulatory mechanisms operative at the GLUT1 (vascular endothelial glucose transporter) gene by cis- and trans-acting elements affecting the promoter region of the gene, i.e., as set forth further in regard to EXAMPLE 17, below.

FIG. 11 schematically depicts the disclosed regulatory mechanisms operative at the GLUT3 (neural glucose transporter) gene by cis- and trans-acting elements affecting the promoter region of the gene, i.e., as set forth further in regard to EXAMPLE 17, below.

FIG. 12 schematically depicts the disclosed regulatory mechanisms operative at the DAT (dopamine re-uptake neural transporter) gene by cis- and trans-acting elements affecting the promoter region of the gene, i.e., as set forth further in regard to EXAMPLE 17, below.

DETAILED DESCRIPTION OF THE PREFERRED EMBODIMENT

Figure 1:
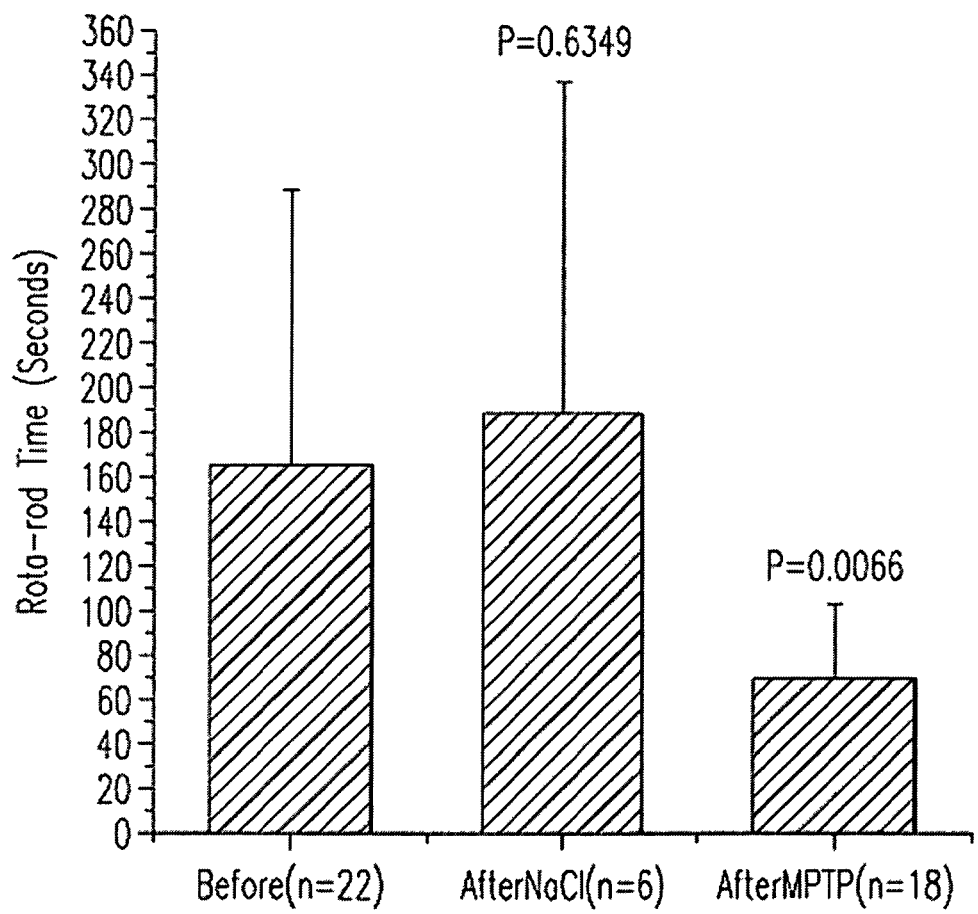
FIG. 1. MPTP treatment of mice resulted in neural lesions that significantly reduced coordination and balance as measured by the time animals were able to remain on a slowly rotating rod, "Rota-Rod", as depicted graphically in the figure and as set forth further in regard to EXAMPLE 13, below. Rota-Rod performance times of C57BL/6 mice before and after lesioning with MPTP, or as a negative control, NaCl.

Objects of the invention provide improved novel chemical entities (NCEs) for metabolic replacement therapy in Parkinson's and related disease. Objects of the invention also provide dopaminergic NCEs with simultaneously enhanced hydrophilicity, i.e., facilitating blood-borne transport; improved intestinal transport; improved blood-brain-barrier endothelial transport; and improved neuronal transport. In other objects, the invention provides NCEs that are N-substituted dopaminergic compounds that, unexpectedly, fulfill the structural binding requirements of dopaminergic receptors despite their N-substitution. In yet other objects, the invention provides a NCEs comprising dopaminergic (dihydroxy-phenyl-) glycosyl-compounds which, unexpectedly, do not inhibit intestinal glucose transporters, but instead, are transportable by these proteins. In other objects, the invention provides N-substituted compounds unexpectedly transportable by dopamine transporters (DAT) in the brain. In still other objects, the invention provides N-phenyl-derivatives that do not inhibit DAT. In other objects, the invention provides N-phenyl derivative compounds that bind DAT and do not inhibit normal loading of $Na^+$ and $Cl^-$ by DAT, or inhibit normal structural conformational changes in the DAT protein required for inward transport of dopamine. In other objects the invention provides domaminergic agonist and partial agonist compounds that do not down-regulate transporter function, e.g., by activating a cellular protein kinase. In other objects, the invention provides compounds that are not modified by monoamine oxidases, catechol-O-methyltransferase or glucuronidation mechanisms operative in the intestine and stomach. In still other objects, the invention provides dopaminergic prodrug NCEs which, unexpectedly, are not metabolized or glucuronidated by intestinal transport mechanisms, and instead, are transported intact. In still other objects, the invention provides a class of dopaminergic NCEs that, unexpectedly, do not alter intestinal or brain glucose or dopamine transport in an adverse manner. In other objects, the invention provides dopamine NCEs having a high degree of innate aqueous solubility, e.g., up to 500 mg/ml. Thus, in other objects the invention provides hydrophilic therapeutic NCE prodrug pharmaceutical compositions which, when administered orally are sequentially transportable in an intact form across the intestine; are also transportable in blood; are also transportable across the blood brain barrier; are transportable by DAT transporters; and are capable of binding to dopamine receptors. In other objects, the invention provides pharmaceutical compositions for metabolic replacement therapy in subjects with Parkinsonism and related diseases. In yet other objects, because the special aqueous solubility of the instant NCE prodrug compounds, the invention provides novel pharmaceutical compositions containing relatively high concentrations of active ingredients allowing administration of a therapeutically effective unit dose in a relatively small volume, i.e., a particular advantage for multi-dose, timed-release, subcutaneous and Intradermal, intranasal, buccal, and trouch pharmaceutical compositions, as well as for pharmaceutical compositions designed to achieve steady-state plasma concentrations. In still other objects, the invention provides bioavailable dopaminergic NCE prodrugs lacking in a reactive carboxylic acid, making co-administration of a decarboxylase or a monoamine oxidase inhibitor unnecessary in a treatment for Parkinson's disease. In other objects, the invention provides dopaminergic NCE prodrug compounds that may be activatable by a brain amidase, e.g., glucosaminidase, galactosaminidase and the like. In other objects, the invention provides dopaminergic NCE prodrug compounds that may be capable of promoting their own transport by upregulating expression and transport rates of intestinal saccharine transporters in gastrointestinal cells. In other objects, the invention provides dopaminergic prodrug NCE compounds comprising a saccharide-transporter-enhancing functionality, (i.e. a dopaminergic moiety), that may compensate for Parkinson's malabsorption, erratic gastrointestinal absorption, irregular gastric contractions, and the like. In still other objects, the invention provides dopaminergic NCE prodrug compounds comprising a dopamine-receptor-enhancing functionality (i.e., a sugar or oligosaccharide moiety) capable of upregulating dopaminergic receptor function, i.e., particularly useful in advanced Parkinsonism where a limited number of functional nigrostriatal neurons may be available and possible glutamate-induced dyskinesia is evident. In other objects, the invention provides stable dopaminergic pharmaceutical compositions suitable for transcutaneous delivery, i.e., not possible with many prior dopa compounds because of their chemical instability.

Applicants do not believe it has been appreciated, until now, that a single chemical entity can affect glucose transporters and dopamine receptors to promote its own transport and receptor binding. Fischer et. al., 1995 reported that tryptamine, 5-OH-tryptamine and dopamine may elicit about a 3-5 fold increase in glucose transport with about 1.8- and 1.5-fold increases in the amount of cell surface GLUT1 and GLUT4 transporters, respectively. Whitfield et al., 1974 suggested that catecholamines, including dopamine, might stimulate carrier-mediated transport of 3-O-methylglucose and galactose in avian erythrocytes. Coffey at al, 1994 suggested that binding of a radiolabeled tropane to a rat striatal membrane dopamine receptors might be increased in the presence of sucrose, fructose and mannose, but not dextrose or N-methyl-D-glucosamine (Coffey, et al. 1994). These respective reports utilized separate dopaminergic and sugar chemical entities, not a single chemical entity, to achieve their measured results.

Embodiments of the invention provide dopaminergic compounds having improved hydrophilicity, bioavailability and blood brain barrier penetration. In other embodiments, the invention provides novel compounds capable of binding to a dopaminergic receptor, a dopamine transporter and a glucose transporter protein. In other embodiments, the invention provides dopaminergic pro-drug compounds that are transportable by all of the following: namely, intestinal transporters, blood transporters and blood-brain-barrier transporters. In yet other embodiments, the invention provides dopaminergic prodrug compounds comprising glycosyl-pro-drug compounds that are: (i) ligands for a dopaminergic receptor; (ii) transportable in an intact form by an intestinal saccharide transporter system; (iii) transportable in an intact form by an endothelial blood brain barrier saccharide transporter system; (iv) transportable by neural dopamine transporters; and (v) metabolizable to provide metabolic replacement therapy. In yet other embodiments, the invention provides novel dopaminergic agonist and partial agonist compounds finding a variety of different potential therapeutic uses in treating peripheral diseases including e.g., congestive heart disease and hypertension.

For purposes of organizing the following disclosure, as well as, improved understanding of the scope and breadth of the instant compounds and their constituent structure, embodiments of the invention are described by the general structure of FORMULA I, "A-B-D-E"  Formula I wherein: each of "—" constitutes a single bond; the "A"-moiety constitutes a dopaminergic cyclic radical; the "B"-moiety constitutes a "bridging" alkyl moiety; the "D"-moiety constitutes a nitrogen "linker"; and, the "E"-moiety constitutes a saccharide as set forth further below, e.g., a mono-, di-, tri- or oligosaccharide. While certain preferred instant compounds according to FORMULA I are set forth below as representative examples, i.e., FORMULAS VII and VIII, below, whereby certain of the preferred constituents are disclosed, before addressing the specifics, the meanings of general terms relating to FORMULA I are provided as follows: namely, "Dopaminergic cyclic radical", as used in reference to the "A-moiety", FORMULA I (supra), is intended to mean a group according to FORMULA II, below, (as depicted linked through a single bond to the B-moiety, supra):

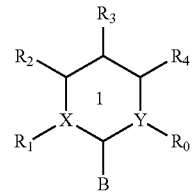

Formula II wherein,

Ring 1 comprises am optionally substituted cyclic or heterocyclic ring, or an optionally substituted aromatic ring, composed of about 4 to about 8 carbon atoms, among which are counted "X" and "Y"; preferably, Ring 1 comprises an optionally substituted aryl or heteroaryl ring; and most preferably, a substituted aryl ring; wherein, $R_1$, $R_2$, $R_3$ and $R_4$ comprise the subject optional ring substituents;

each of X and Y are optional and when present comprise a carbon atom, a halogen atom or a lower alkyl, preferably, a carbon atom or a lower alkyl chain having 2 carbon atoms, most preferably a single carbon atom;

$R_0$ comprises hydrogen;

$R_1$, $R_3$ or $R_4$ comprise a group selected from among hydrogen, hydroxyl, halogen, halo-lower alkyl, alkoxy, alkoxy-lower alkyl, halo-alkoxy, thioamido, amidosulfonyl, alkoxy-carbonyl, carboxamide, amino-carbonyl, and alkylamine-carbonyl;

$R_2$ comprises hydroxyl; and, preferably, both $R_2$ and $R_3$ comprise hydroxyl and $R_1$ and $R_4$ comprise hydrogen.

"Bridge", when used in reference to the B-moiety, of FORMULA I (supra), is intended to mean a group according to FORMULA III, below, (as depicted linked through single bonds to each of the A-moiety and the D-moiety, supra):

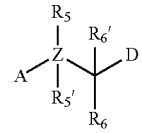

Formula III wherein,

Z is optional and when present comprises a lower alkyl optionally substituted with $R_5$ and $R_{5'}$; preferably, Z is absent or a lower alkyl comprising 1 or 2 carbon atoms; most preferably, Z is absent or a one carbon atom; and, $R_5$ and $R_{5'}$ (when present) and $R_6$ and $R_{6'}$ (when present) are groups selected from among hydrogen, hydroxyl, alkoxyl, carboxyl, alkoxylcarbonyl, aminocarbonyl, alkylamino-carbonyl and dialkylamino-carbonyl.

"Linker", when used in reference to the D-moiety, FORMULA I (supra) is intended to mean an optionally $R_7$-substituted amide or amine linking the B-moiety with the E-moiety, i.e., through each of two single bonds, according to FORMULA IV, below (depicted linking the B- and E-moieties of FORMULA 1): namely,

Formula IV wherein, N comprises a nitrogen atom of a primary or secondary amine or an amide, preferably $R_7$ is a hydrogen or methyl, most preferably, $R_7$ is hydrogen.

Thus, according to the foregoing disclosure, the assemblage of constituents A-B-D-E (FORMULA I) comprises compounds having the general structure according to FORMULA V: namely,

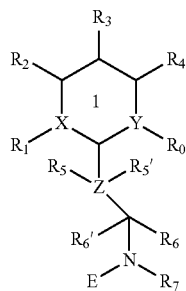

Formula V wherein, the constituents of Formula V are as set forth above; the relationship of "Z" with $R_5$, $R_{5'}$, $R_6$ and $R_{6'}$ may be cis or trans; and, the relationship of "N" with $R_6$, $R_{6'}$, $R_7$, "Z" and "E" may be either cis or trans.

"Saccharide" is intended to mean a mono-, di-, tri- or oligosaccharide made up of n sugar subunits linked to each other by glycosidic bonds, which subunits, when n is greater than 1, may be the same or different in respect to: (i) the type of constituent sugar residues (e.g., homo- or heteropolymeric); and, (ii) the localization of axial and equatorial ring substituents, i.e., $R_{8-11}$ (supra); (iii) the number of carbon atoms (i.e., $C_{1-9}$ supra); and (iv) the ring carbon locations and orientations of hydroxyl groups.

"Sugar", used interchangeably with monosaccharide, when used in reference to constituents groups of the "B-moiety" (supra), is intended to mean a substituted or unsubstituted sugar residue having 3 carbon atoms (trios) 4 carbons (tetraose), 5 carbons (pentose), 6 carbons (hexose), 7 carbons (heptose), 8 carbons (octose) or 9 carbon atoms (nonose). FORMULA VIa, VIb, VIc and VId illustrate the interrelated straight chain, hemiacetal and acetal forms of a hexose sugar, i.e., depicted in FORMULA VIa and VIb using a modified Fischer projection formula, and depicted in FORMULAS VIc and VId using modified Haworth projection formulas:

and, while for purposes of illustration the Fischer and Hayworth formulas are set forth in FORMULAS Va, Vb, Vc and Vd depicting the configuration of a glucosyl residue, the scope of the invention is not intended to be so limited, as set forth further in the accompanying disclosure, below;

The numbers "1", "2", "3", "4", "5", "6" and the like appearing in FORMULA VIa and VIb, are intended, to refer to particular numbered carbon atoms in the respective different sugar residues, e.g., $C_1$, $C_2$, $C_3$, $C_4$, $C_5$ and $C_6$, (i.e., $CH_2OH$). In certain optional embodiments, carbon atoms depicted in FORMULAS VIa, VIb, VIc and VId may be optional, e.g., in trioses $C_2$, $C_3$ and $C_4$ are absent. In aldoses, according to convention, positional numbering of carbon atoms is initiated from the chain terminal aldehyde and in ketoses, from the chain terminal carbon atom nearest the ketone. In alternative embodiments, $C_2$, $C_3$ and $C_4$ (FORMULAS VIa, VIb, VIc and VId) are optional; preferably, $C_3$ is present; most preferably, all of $C_2$, $C_3$ and $C_4$ are present;

The optional dotted line connecting the $C_5$ oxygen atom to the $C_1$ carbon atom (FORMULA VIb) is intended to mean an optional ester bond, in the absence of which bond FORMULA VIb is acyclic as depicted in FORMULA VIa;

In certain embodiments, the linkage of the E-moiety to the D-moiety amine or amide (supra) occurs through a single bond formed between the subject amine or amide nitrogen and either of the $C_1$, $C_2$, $C_3$, $C_4$, $C_5$ or $C_6$ carbon atoms of the subject sugar (FORMULAS VIa-VId). Preferably, with hexosyl residues the linkage is between the D-moiety amine or amide and the $C_1$, $C_2$, $C_4$ or $C_5$ carbon, most preferably, the linkage is between the D-moiety amine or amide and the $C_1$ or $C_2$ carbon. Preferably, with pentosyl residues (i.e., the $C_2$ residue depicted in FORMULAS VIa-VId is absent), linkage is between the D-moiety amine or amide and the $C_4$ or $C_5$ carbon atom (i.e., as depicted in FORMULAS VIa-VId). Preferably, with tetraosyl residues (i.e., when both $C_2$ and $C_4$ of FORMULAS VIa-VId are absent), linkage is between the D-moiety amine or amide and the $C_5$ or $C_6$ carbon atom (i.e., as depicted in FORMULAS VIa-VId). Preferably, with triosyl residues (i.e., when $C_2$, $C_3$ and $C_4$ of FORMULAS VIa-VId are absent), linkage is between the D-moiety amine or amide and the $C_5$ or $C_6$ carbon (i.e., as depicted in FORMULAS VIa-VId). Most preferably, the E-moiety is hexosyl and linkage is between the D-moiety amine or amide and the $C_1$, $C_2$ or $C_4$ carbon atoms.

The E-moiety optional substitutions according to FORMULAS VIa, VIb, VIc and VId comprise $R_8$, $R_9$, $R_{10}$, $R_{11}$ and

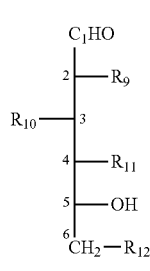

Formula VIa

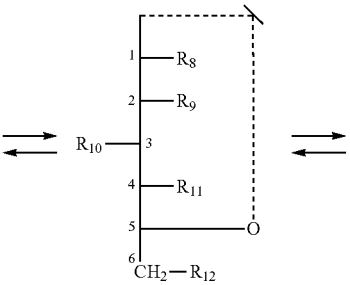

Formula VIb

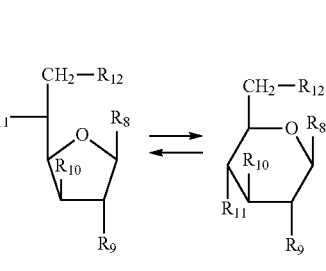

Formula VIc

Formula VId wherein,

The bi-directional arrows between FORMULAS VIa, VIb, VIc and VId are Intended to mean that the subject sugar residues are interconvertible between straight chain, aldosyl, furanosyl and pyranosyl forms at some equilibrium constant;

$R_{12}$; preferably, when the D-moiety forms a carbon to nitrogen bond with $C_1$, then $R_8$ is hydrogen; preferably, when the D-moiety forms a carbon to nitrogen bond with $C_2$, then $R_9$ is hydrogen; when the D-moiety forms a carbon-to-nitrogen bond with $C_3$, then $R_{10}$ is hydrogen; when the D-moiety forms a carbon-to-nitrogen bond with $C_4$ then $R_{11}$ is hydrogen; most preferably, the D-moiety forms a carbon-to-nitrogen bond with either of $C_1$ or $C_2$.

Substituents $R_8$, $R_9$, $R_{10}$, $R_{11}$ and $R_{12}$ (according to FORMULAS VIa-VId) are selected from hydroxyl, hydrogen, methyl, halogen, lower alkyl, halo-lower alkyl, alkoxyl, ketone, carboxyl, amine, amido, N-acetyl, N-methyl, N-linked lower alkyl, aminocarbonyl, alkylaminocarbonyl, dialkylaminocarbonyl, phosphate, sulfate, and thiol. In certain alternative embodiments, $R_{12}$ may be a monosaccharide or disaccharide, with the proviso that $R_{12}$ when present as a substituent in a monosaccharide glucosyl sugar $R_{12}$ is not carboxyl, i.e., the instant sugar is not a $C_6$-glucuronic acid;

Preferably, two of either $R_8$, $R_9$, $R_{10}$, $R_{11}$ and $R_{12}$ are hydroxyl; most preferably, $R_{10}$ and $R_{12}$ are hydroxyl.

Representative examples of E-moiety sugar residues include the following: namely, polyhydroxy $C_1$•aldehydes (e.g. aldoses and ketoaldoses); polyols resulting from e.g., reduction of the $C_1$ aldehyde carbonyl to a hydroxyl (e.g., alditols and ketoses); polyhydroxy acids resulting e.g., from oxidation of the $C_1$ aldehyde and/or the chain terminal hydroxyl (e.g., aldonic, ketoaldonic, aldaric and ketoaldaric); amino-sugars resulting from replacement of any hydroxyl in the chain with an amino (e.g., aldosamines and ketosamines); aldehydro-acids resulting e.g. from oxidation of only the chain terminal hydroxyl in an aldehydro-sugar (e.g., uronic acids and keto-uronic acids); and their various lactones, i.e., cyclic esters of hydroxy carboxylic acids containing one 1-oxacycloalkan-2-one structure. The subject sugars may be straight chains and/or cyclic 3-, 4-, 5-, 6-, 7-, 8- and 9-membered sugar residues (e.g., hemiacetals and acetals) optionally substituted and linked with the D-moiety as set forth, supra. Representative triosyl residues include the aldoses D- and L-glyceraldehyde and derivatives thereof e.g., glyceraldehyde and glyceric acid phosphates; the keto-sugars D- and L-dihydroxyacetone and derivatives thereof. Representative tetraosyl residues include the aldoses D- and L-erythrose, threose, streptose and apiose; the keto-sugars D- and L-erythrulose; and derivatives thereof. Representative pentosyl residues include the D- and L-aldoses ribose, arabinose, xylose and lyxose; the D- and L-ketoses ribulose and xylulose; and, derivatives thereof. Representative hexosyl residues include aldosyl, furanosyl and pyranosyl sugars e.g., cyclic and acyclic D- and L-aldoses such as allose, altrose, glucose, mannose, gulose, idose, galactose, talose, fructose, glucono-1,4-lactone, glucaro-1,4:6,3-dilactone, gluconofuranono-6,3-lactone; the ketoses ribo-hexylose, arabino-hexulolose, xylo-hexylose and lyxo-hexylose; and derivatives thereof. Representative 7-membered residues (i.e., heptosyl residues) include e.g., sedoheptulose and derivatives thereof; and, representative 9-membered residues (i.e., nanosyl residues) include N-acetylneuraminic acid and derivatives thereof. Also representative are, 2-deoxy-ribos, 6-deoxyglucose and 2-deoxyglucose, xyloascorbyllactone, digitoxose (2-deoxyaltromethylose), fucose (6-deoxy-galactose), gluoanolactone, galaconolactone, rhamnose (6-deoxy-mannose), fructose (2-keto-arabohexose), aldaric acids, alditols, aldonic acids, ketoaldonic acids, and amino sugars; with the proviso that the E-moiety is not a cyclodextrin. Representative alditols include e.g., erythritol, threitol, ribitol, arabinitol, xylitol, lyxitol, glucitol, allositol, altrositol, mannositol, gulositol, idositol, galactositol, talositol and their derivatives. Representative aldonic acids include erythronic acid, threonic acid, ribonic acid, arabinonic acid, xylonic acid, lyxonic acid, gluconic acid, allonic acid, altronic acid, mannonic acid, gulonic acid, idonic acid, galactonic acid, tolonic acid and their derivatives. Representative ketoaldonic acids include erythro-tetraulosonic acid, threo-tetraulosonic acid, ribo-pentulosonic acid, arabino-pentulosonic acid, xylo-pentulosonic acid, lyxo-pentulosonic acid, gluco-hexulosonic acid, allo-hexulosonic acid, altro-hexulosonic acid, manno-hexulosonic acid, gulo-hexulosonic acid, ido-hexulosonic acid, galacto-hexulosonic acid, talo-hexulosonic acid and their derivatives. Representative aldaric acids include erythraric acid, threaric acid, ribaric acid, arabinaric acid, xylaric acid, lyxaric acid, allaric acid, altraric acid, glucaric acid, mannaric acid, gularic acid, idaric acid, galactaric acid, talaric acid and their derivatives. Representative of amino sugar include erhtyrosamine, threosamine, ribosamine, arabinosamine, xylosamine, lyxosamine, allosamine, altrosamine, glucosamine, N-acetylglucosamine, N-methlglucosamine mannosamine, gulosamine, idosamine, galactosamine, talosamine and their derivatives. Representative uronic acids include erythrosuronic acid, threosuronic acid, ribosuronic acid, arabinosuronic acid, xylosuronic acid, lyxosuronic acid, allosuronic acid, altrosuronic acid, glucuronic acid, mannosuronic acid, gulosuronic acid, idosurnic acid, galactosurnilc acid, talosuronic acid and their derivatives. Representative keto-uronic acids include keto-crythrosuronic acid, keto-threosuronic acid, keto-ribosuronic acid, keto-arabinosuronic acid, keto-xylosuronic acid, keto-lyxosuronic acid, keto-allosuronic acid, keto-altrosuronic acid, keto-glucuronic acid, keto-mannosuronic acid, keto-gulosuronic acid, keto-idosuronic acid, keto-galactosuronic acid, keto-talosurnic acid and their derivatives. Representative lactones include erythrolactone, threolactone, ribolactone, arabinolacton, xyloslactone, lyxoslactone, allolactone, altrolacone, glucolactone, mannolactone, gulolactone, idolactone, galactolactone, talolactone and their derivatives.

Preferably, the subject E-moiety comprises an aldose or ketose pentose or hexose sugar selected from the group consisting of D- and L-enantiomers of ribose, glucose, galactose, mannose, arabinose, allose, altrose, gulose, idose, talose and their substituted derivatives. Most preferably, the subject E-moiety comprises an aldose pentosyl or hexosyl sugar selected from ribose, glucose, galactose, glucosamine, galactosamine, N-acetylglucosamine, N-acetylgalactosamine, N-acetyl ribosamine, xylose, mannose and arabinose.

"Di-sacchride", when used in regard to the subject E-moiety, is intended to mean a polymeric assemblage of 2 sugar residues. Representative examples of disaccharides include homo-polymeric (e.g., maltose and cellobiose) and heteropolymeric (e.g., lactose and sucrose) assemblages of sugars as set forth supra.

"Tri-saccharide", when used in regard to the subject E-moiety, is intended to mean a polymeric assemblage of 3 sugar residues, e.g., as set forth supra.

"Oligosaccharide", when used in relation to the subject E-moiety, is intended to mean a polymeric assemblage of about 4 to about 10 constituent homo-monosaccharide sugars (i.e., all the same constituent) or hetero-monosaccharide (i.e., different constituent) sugars. Each of the subject constituent sugars is linked one-to-another in a serial array through a series of glycosyl bonds formed between the $C_1$ and $C_4$ carbon atoms; or alternatively, between the $C_1$ and $C_3$ carbon atoms; or alternatively, between the $C_1$ and $C_6$ carbon atoms; with the proviso that when the E-moiety is according to FORMULA VIa, VIb, VIc or VId and comprises glycosidic linkage at $C_1$-$C_4$ then $R_8$ and $R_{11}$ are hydrogen, when linkage is at $C_1$-$C_3$, then $R_8$ and $R_{10}$ are hydrogen, and when linkage is at $C_1$-$C_6$, then $R_8$ and $R_{12}$ are hydrogen.

Preferably, the subject di-, tri- and oligosaccharide E-moieties are metabolizable and/or acid hydrolyzable to mono-, di- and tri-saccharides and transportable by saccharide transporters in mammals; most preferably, when present as an oligosaccharide the subject E-moiety comprises a residue selected from the group of metabolizable di- and tri-saccharides consisting of: (i) homopolymers such as an erythran, a threan, a riban, an arabinan, a xylan, a lyxan, an allan, an altran, a glucan (e.g. maltose, isomaltose, cellobiose), a mannan, a gulan, an idan, a galactan, a talan and their substituted derivatives; (ii) heteropolymers such as erythrosides, threosides, ribosides, arabinosides, xylosides, lyxosides, allosides, altrosides, glucosides (e.g., sucrose; (Glc-β1,4-Frc), galactosides (e.g., lactose; Gal-β1,4-Glc), mannosides, gulosides, idosides, talosides and their substituted derivatives. Other representative oligosaccharides include the following: namely, sucrose glycogen, fucosidolactose, lactulose, lactobionic acid, amylose, fructose, fructofuranose, scillabiose, panose, raffinose, amylopectin, hyaluronic acid, chondroitin sulfate, heparin, laminarin, lichenin and inulin. Preferably, the subject E-moiety, when present as an oligosaccharide, is selected from the group consisting of glucosyl and galactosyl homo- and heteropolymers e.g., glucans, galactans, glucosides and galactosides. The subject E-moiety is not a cyclodextrin or derivative thereof.

Thus according to the foregoing disclosure, embodiments of the invention provide a variety of compounds which are within the spirit and bounds of the instant invention. For example, FORMULA VIIa and VIIb, below, depict an Illustrative E-moiety aldose hexosyl sugar (FORMULA VIIIa) linked at $C_2$ with A-B-D and Interconvertible with its pyranose form (FORMULA VIIb).

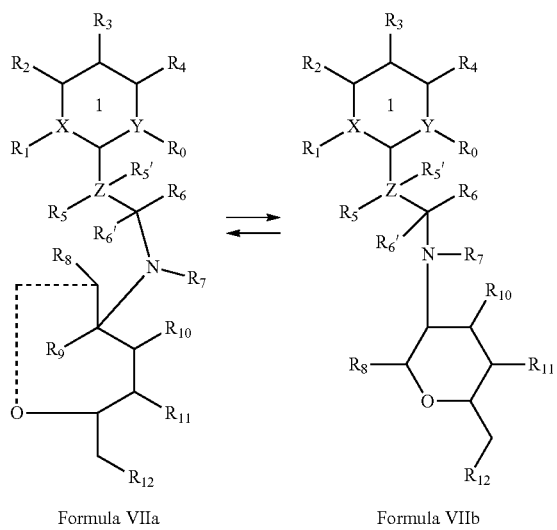

Formula VIIa      Formula VIIb wherein the X, Y, Z and $R_1$-$R_{12}$ are as set forth in regard to FORMULA I, supra.

Those of skill in the art will recognize varied synthetic routes for assembling test compounds from the constituents set forth in the foregoing disclosure. The skill for determining the functionality of a test compound according to the invention is also known in the art. For instance, assays for measuring ligand binding to dopaminergic receptors are known as are assays for determining that a test compound is transportable by a saccharide transporter. (Further disclosure of illustrative testing methods being provided in the accompanying disclosure below.)

In other presently preferred embodiments, the invention provides N-linked transportable and metabolizable dopaminergic compounds according to FORMULAS VIIIA and VIIIB, which follow on the next page.

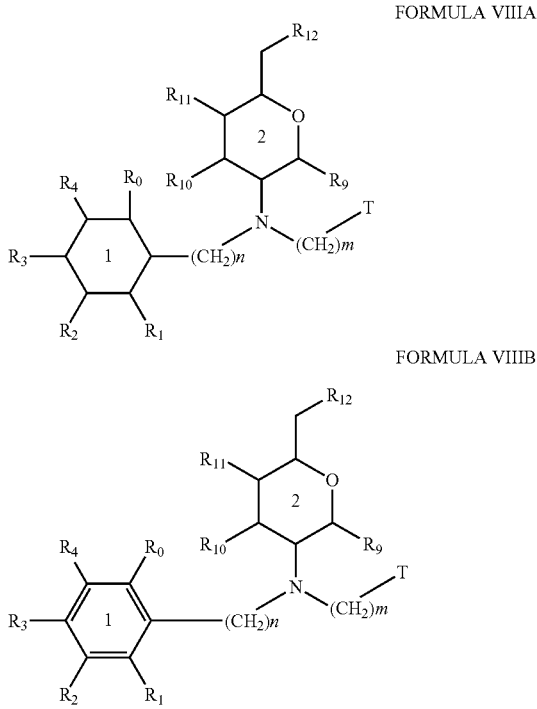

FORMULA VIIIA

FORMULA VIIIB wherein:

Ring 1 is the A-moiety (described supra); substituents $R_1$-$R_4$, $R_8$, $R_{10}$, $R_{11}$ and $R_{12}$ are as described (supra) and Ring 2 is the E-moiety, also as described (supra);

T comprises an optional amine, amide, halogen, thioamido, oxyamido, ureido, thioureido, thiamido, dithiamido, acetyl, carboxylic acid amide, carboxamide, amino-carbonyl, alkylaminocarbonyl, dialkylaminocrbonyl, preferably amine or amide, most preferably amine;

n is an integer selected from within the range of 1 to 4; and, m is an integer selected from within the range of 0 to 4, with the proviso that value of (m+n) is an integer selected from within the range of 1 to 4;

$R_2$ and $R_3$ are hydroxyl;

$R_0$, $R_1$ and $R_4$ are hydrogen;

$R_8$, $R_9$, $R_{10}$ or $R_{11}$ are selected the group consisting of hydrogen, hydroxyl, halogen, hydroxyl substituted lower alkyl, halogen substituted lower alkyl or lower alkyl;

$R_{12}$ is selected from the group consisting of hydrogen, lower alkyl, substituted lower alkyl, hydroxyl, alkoxyl, or halogen, preferably hydrogen, lower alkyl, halogen- or hydroxyl-substituted lower alkyl, haloalkoxy, hydroxyl, alkoxyl, alkoxycarbonyl, thioalkoxy or halogen, or a monosaccharide, disaccharide, trisaccharide or oligosaccharide. Most preferably, $R_{12}$ is hydrogen, hydroxyl or substituted lower alkyl.

In alternative embodiments, compounds according to FORMULA VIIIA or VIIIB are provided in which $R_1$ and $R_4$ comprise a group selected from the group consisting of hydrogen, hydroxyl, halogen, hydroxyl substituted lower alkyl, halogen substituted lower alkyl and carboxyl; preferably, $R_1$ and $R_4$ comprise hydrogen, hydroxyl or halogen.

As used herein, the following additional terms are intended to have meanings as follows: namely, "Halogen" is intended to mean a fluorine, chlorine, bromine, or sulfur atom or ion or group. Preferred halo groups are chlorine, bromine, thiol and sulfonyl and most preferred, chlorine.

"Lower alkyl" is intended to mean a hydrocarbon chain containing fewer than six carbon atoms, preferably fewer than four and most preferably two or 3 carbon atoms. Representative lower alkyl groups include methyl, ethyl, n-propyl, i-propyl, n-butyl, t-butyl and i-butyl. Presently preferred alkyls are methyl, ethyl or i-propyl, and most preferably, ethyl.

"Substituted lower alkyl" is intended to mean a lower alkyl in which one or more of the hydrogen atoms are replaced by a substituent group. Representative substituent groups include hydroxy, alkoxy, halogen, amino, amido, carboxyl, thiol, sulfonyl, methoxy and the like.

"Halo-lower alkyl" is intended to mean a lower alkyl in which one or more of the hydrogen atoms on the hydrocarbon chain has been replaced by a halogen atom.

"Cycloalkyl" is intended to mean a closed saturated monocyclic hydrocarbon ring made up of about 4 to about 9 carbon atoms, preferably about 5 to about 7 carbon atoms and most preferably 6 carbon atoms. Representative examples of cycloalkyl compounds include phenyl, piperidyl, piperazinyl, diazinyl, morpholinyl, isooxazoanyl and the like.

"Heterocyclic" is intended to mean a close saturated monocyclic ring made up of about 4 to about 8 carbon atoms and about 1 to about 2 non-carbon atoms; preferably, about 5 to about 6 carbon atoms and 1 non-carbon halogen or oxygen atom; and, most preferably 5 carbon atoms and 1 non-carbon halogen or oxygen atom.

"Aromatic", and "aryl", are used interchangeably to mean a closed unsaturated monocyclic hydrocarbon ring system made up of about 3 to about 9 carbon atoms having a delocalized π-electron system. Preferably, the subject aryl ring is made up of about 5 to about 7 carbon atoms and most preferably, 6 carbon atoms. Representative aromatic rings include benzyl, pyranyl, pyridyl, pyrimidinyl, thiadiazinyl and pyridazinyl, with benzyl preferred.

"Amine" is intended to mean an —NHR substituent group.

"Amide" is intended to mean an —C(O)N—(R')R" or —HNC(O) substituent group, where R' and R" are hydrogen or a substituent such as hydroxy, lower alkyl, amino, or the like. Preferred amino groups are those wherein R' or R" is hydrogen.

"Alkoxy" is intended to mean an —OR substituent group.

"Halo-lower alkyl" is intended to mean a halogen substituted lower alkyl; preferably, a halogen substituted lower alkyl having 2 to 6 carbon atoms; most, preferably, a chlorine or fluorine substituted lower alkyl having 2 to 4 carbon atoms.

"Alkoxy-lower alkyl" is intended to mean an alkoxy compound, supra, wherein R comprises a lower alkyl; preferably a 2 to 6 carbon lower alkyl; and most preferably, a 2 to 4 carbon lower alkyl.

"Thioalkoxy" is intended to mean an —SOR substituent group.

"Aminocarbonyl" is intended to mean a —C(O)NH$_2$ substituent group.

"Alkylaminocarbonyl" is intended to mean a —C(O)NHR substituent group wherein R is a lower alkyl.

"Alkoxycarbonyl" is intended to mean a —C(O)OR substituent group.

"Carboxamide" is intended to mean a —NR'COR substituent group.

"Dialkylaminocarbonyl" is intended to mean a —C(O)NR'R substituent group, wherein R' and R constitute lower alkyl groups.

"Haloalkoxy" is intended to mean a —OR substituent group where R is a haloalkyl.

"Oxyamido" is intended to mean a —OC(O)NH— or —HNC(O)O-substituent.

"Thioamido" is Intended to mean a —SC(O)NH— or —HNC(S)— substituent.

"Amidosulfonyl" is intended to mean a —NHSO$_2$— substituent.

"Aldose" is intended to mean a polyhydroxyaldehyde of the sugar of the general form H[CH(OH)]$_n$C(=O)H, wherein n is an integer greater than one; preferably, the subject aldose is in equilibrium with furanosyl and pyranosyl forms.

"Ketose", also known as ketoaldose, is intended to mean a sugar containing both an aldehydic group and a ketonic carbonyl group; preferably, the subject ketose is in equilibrium with intramolecular hemiacetal forms.

"Aldaric acid", used interchangeably with glycaric acid, is intended to mean a polyhydroxy dicarboxylic acid of a sugar having the general formula HOC(=O)[CH(OH)]$_n$C(=O)OH, wherein n is greater than 1 and such as may be derived from an aldose by oxidation of both terminal carbon atoms to carboxyl groups.

"Alditol" is intended to mean an acyclic polyol having the general formula HOCH$_2$[CH(OH)]$_n$CH$_2$OH, wherein n is greater than one.

"Aldonic acid", used interchangeably with glyconic acid, is intended to mean a polyhydroxy acid having the general formula HOCH$_2$[CH(OH)]$_n$C(=O)OH, wherein n is greater than one and such as may be derived from an aldose by oxidation of the aldehyde function.

"Amino sugar" is intended to mean a sugar (defined supra) having one alcoholic OH group replaced by an amino group.

"Glycosyl" is intended to mean a hexose sugar substituent group; preferably, a glucosyl or galactosyl substituent.

"Glycosylamine", also known as N-glycosides, is intended to mean glycosyl group attached to an amino —NR$_2$ group; preferably, an N-linked glucosyl or galactosyl substituent.

"Furanose" is intended to mean a cyclic hemiacetal form of a sugar in which the ring is five membered.

"Pyranose" is intended to mean a cyclic hemiacetal form of a hexose sugar in which the ring is six membered.

"Saccharide transporter" is intended to mean a cellular membrane protein capable of binding a saccharide and transporting that saccharide from one location to another on the cell. Representative examples of saccharide transporters include a glucose transporters (e.g., GLUT 1, 2, 3, 4 and 5), galactose transporters, a manose transports, fructose transporters, arabinose transporters and the like. Those skilled in the at are cognizant of methods by which test compounds according to the invention may be shown capable of binding to a saccharide transporter, i.e., as a ligand binding in a specific and saturable manner, i.e., examples of which are provided below. In one illustrative assay a labeled ligand (e.g., $^3$H radiolabeled at a concentration selected from within 0.1 nM to 10 mM) is incubated at room temperature, 37° C., and 4° C. with an aliquot of cells (or a membrane preparation) having a saccharide transporter. After the incubation the cells (or membranes) are washed (e.g., by centrifugation through an isobutylpthalate or sucrose cushion) and the amount of labeled ligand associated with the cell (or membrane) pellet is determined (e.g., by quantifying radioactivity). The data obtained in this manner may be used to conduct a Scatchard binding analysis of the data from which association constant and the relative binding affinity of the transporter for the test compound.

Embodiments of the invention provide a variety of dopaminergic glycoconjugates in which the primary amine of Dopa or dopamine (3-hydroxytryamine) may be viewed as covalently bonded with a sugar, or alternatively, the compounds may be viewed as having a "Dopa-like" substituent covalently bonded with an amino sugar, e.g., glucosamine, galactosamine and the like. Depending upon the view with is taken, a variety of different synthesis roues is available to those of skill in the art, and with different possible reagent starting materials.

Preparation of Dope and dopamine (and their derivatives) are known in the art and variety of compounds are commercially available for use as starting materials in chemical syntheses, some examples of which are disclosed further below. Similarly, methods are known for detection and quantitation of dopamine and N-acyldopamine and dopamine glucosides, e.g., by HPLC in 0.1M potassium dihydrogen phosphate-phosphoric acid buffer pH 2.0 and 0.1M potassium dihydrogen phosphate-phosphoric acid buffer, pH 3.0 acetonitrile (93:7, v/v), respectively (Kawasaki et. al., 1913). General separation and detection methods for distinguishing catechols from dopamine derivatives in complex mixtures are also known, e.g., by C18 column chromatography using two mobile phases (i.e., acetonitrile and methanol/sodium octyl sulfate) with electrodetection (Morgan, et. al., 1987). More recently, positive ion electrospray mass spectrometry (ESMS) and tandem mass spectrometry (ESMS-MS) have been used to identify glucosamine, N-acetyldopamine and catecholamine adducts of glucosamine in complex solutions (Kerwin et al., 1999; Kerwin at al. 1996; Kerwin et. al., 1997).

Assays for determining the substitution ratios of E-moieties covalently bound with A-B-D (FORMULA I, supra), are also known. For example, benzothiazolone hydrazone assays for bound amino sugars are known in the art. In addition, procedures for determination of hexosamines or N-acetylhexosamines based on the procedures of Elson and Morgan (e.g., Horton, 1969) are known. Formation of a chromophore in this case requires the free sugar, e.g., released by hydrolysis. However, quantitative liberation of amino sugars may be difficult because of their extreme stability to strong acid conditions, in this case one alternative method involves reacting with 3-methyl-2-benzthiazolinone hydrazone hydrochloride (MBTH) under mild acidic conditions e.g., 0.5N HCl, to obtain de-N-acetylation with colorimetric determination and quantitation of the resultant benzothiazolones (e.g., Manzi et. al., 1993; Schauer, 1978).

Preparative methods for aldoses, ketoses, pyranosyl- and furanosyl-compounds, and their derivatives, suitable for use as starting materials in synthesis of the compounds of FORMULA I are also known. For example, synthesis routes for amino sugars through aldonic acids by hydrogen cyanide in Strecker- and Fischer-Leuchs-type reactions (Horton, 1969 at pp. 18-62); Kuhn-type amino nitrile condensation reactions of aldoses with ammonia, benzylamidine or arylamine; intramolecular Amadori rearrangements converting aldosylamines into aminoketoses; direct amidation reactions of sugar epoxides; amination displacement of sulfonic esters and sulfones; synthesis by phenylhydrazone or urononitrile reduction; reduction of sugar oximes and aziridine derivatives; ring closure reactions with dialdehydes; and various inter-conversions of axial and equatorial hydroxyl groups. Similarly, routes for obtaining 2-amino-2-deoxy-D-glucose (GlcN) derivatives from natural sources, e.g., chitin, are known (Horton, 1969 at pg. 62). Methods are also described for N-acetylation and selective N-acylation of glucosamine (Horton, 1969 at pp. 63-68) and certain methods for N-alkylation and synthesis of N-aryl compounds have also been described (Horton, 1969 at pp. 71-73), but generally yield may be low and in acid-alcohol mixtures the 3D-glycosides of N-acetylated amino sugars may mutarotate (Horton, 1969 at pp. 71-73 and pg. 91) giving α-D-forms. i.e., a situation where the reverse reaction does not apparently occur.

Aims in common syntheses are retention of the carbon chain of the sugar, but also using reactions which allow simple reagents and uncomplicated non-chromatographic chromatographic workups with use simple protective groups, aiming for stable, crystalline and readily purifiable products, and reasonably high overall yields (e.g., 7S % per step). Comparatively few reaction channels capable of achieving these aims with oligosaccharide E-moieties. For example, in an initial stage the starting sugar material may be frozen in one of its tautomeric forms to provide acyclic furanoid or pyranoid derivatives onto which ensuing chemistry can be unequivocally imposed, i.e., using fixation reactions uncovered before the turn of the century (e.g., mercaptalization of acyclic dithioacetals, isopropylidenation of furanoid systems or generation of pyranoid glycosides, glycals or hydroxyglycal esters). Next, a desired protective group substituent functionality may be introduced, e.g., benzoylation for D-glucose or D-maltose (i.e., forming —OBz protecting groups), or conversion to pyranoid enediolones (dihyropyranones with 2 chiral centers at one side of the ring) may be accomplished in a 4-step procedure with about 60% overall yield by acetonation, oxidation, acid removal of isopropylidene groups and benzoylation under slightly basic conditions (e.g., $NaHCO_3$ as described by Lichtenthaler) to elicit-elimination of benzoic acid. Protected tetrabenzoyl-glucosyl residues are relatively acid-sensitive but alkali-stable.

For preparation of lactones, e.g., starting from glycal or hydroxyglycal esters enantiopure dihydropyranones may be prepared yielding products suitable for use as intermediates in further syntheses. $BF_3$-induced removal of the allylic acyloxy function may be used to form the allylcarboxonion ion, susceptible to attach at C-1 by m-chloroperbenzoic acid (MCPBA) resulting in formation of a perester intermediate which undergoes fragmentation to yield lactones. Lactones may also be prepared using N-acetylglucosminolactone as a starting material. Preparation of amino sugar lactones is known (e.g., Findlay et. al., 1958).

For assembly of heptones, octones and nonone sugars, 5 carbon acyclic pentenal building blocks can be prepared from 6 membered cyclic glycal esters (e.g., triacetyl-glycal or triacetyl-galactal), or from hexoses via enolactone conversion and mercuric ion-catalyzed acid opening of the ring to form e.g., 4,5,6-trihydroxy-hexanals. A reactive $C_1$ carbonyl may be produced at relatively high yield by reacting the intermediate pentenal compound with $NH_2OH$, then MeCHO and NaOAc in $Me_2CO$. The carbonyl produced in such reactions may be suitable for addition of carbon atoms, e.g., attack by a lithium-based 3-carbon synthon such as the lithium enolate of acetone. Enantiomer-specific introduction of a reactive halide leaving group at $C_5$ is also known. Production of reactive 2,6-dihydropyrones is also known, which are, in turn useful for hydride addition, and a variety of C-branching with Grignard or cuprate reagents and Diels-Alder types of cycloadditions. For synthesis of oligosaccharides, anomeric effects at $C_1$ carbons allow entantiomer specific addition of halide leaving groups to 2,6-dihydropyrones, e.g., Br, yielding compounds which are useful in-turn in alcoholysis reactions with simple acid scavengers (e.g., MeOH in $NaHCO_3$) yielding $C_1$ methyl esters at high yields and also providing β-glycosides at relatively high yields. Synthetic methods for lengthening the carbon chain of aldoses is also known, e.g., Kiliani-Fischer synthesis with conversion to glyconic acids of the next higher carbon number by addition of HCN and hydrolysis (under acidic conditions) of the resulting cyanohydrins to glyconolactones followed by reduction to aldoses. Methods for reducing carbon chain length are also known, e.g., Ruff degradation involving conversion to a glyconic acid, formation of a calcium salt and oxidation of the salt by hydrogen peroxide/$Fe^{3+}$ or oxidation (e.g., in nitric acid) of an aldose to a keto acid with cleavage at the resultant carbonyl to form lower carbon number aldaric dicarboxylic acids. Methods for separation of epimers (diastereomers) are also known, e.g., by crystallization of lactone salts with differing physical properties followed by reduction to a single pure aldose or ketose epimer. Methods for converting between epimers are also known, e.g., oxidation to a glyconic acid followed by treatment with pyridine to establish an equilibrium between the epimers, separation of the epimers as lactone salts, followed by reduction to the epimeric pure aldose. Methods for separation of anomeric (i.e., $C_1$) diastereomers are also known. Methods for conversion of aldoses to ketoses, e.g., through enediols under alkaline conditions, are also appreciated in the art as are methods for converting aldoses to glyconic monocarboxylic acids, e.g., by reduction to glycitols and oxidation to glyconic acids.

According to the instant methods, lactones of sugars and their acids are preferred starting materials for synthesis of compounds according to FORMULA I, e.g., aldonic and keto-aldonic acids (supra). Preferably, the starting materials are lactones or aldoses, ketoses, aldonic and keto-aldonic monocarboxylic acids, i.e., aldehydo lactones and lactone acids and their salts. According to instruction provided herein, glucuronic $C_6$ acid lactones are not preferred starting material according to the instant methods, i.e., drug glucuronides being rapidly metabolized and removed from circulation.

Also envisaged as within the scope of the present invention are acid- and alkali-hydrolyzable controlled-release multimers of the compounds of FORMULA I, wherein a first A-B-D-E molecule is linked through a hydrolyzable cross-linker "R" to a second A-B-D-E molecule, e.g., E-D-B-A-R-A-B-D-E. Linkage between the first and the second molecules may be effected at any of the A, B, D or E moieties, e.g., using methods known in the art.

Methods for determining that a test compound synthesized according to the methods of the invention is dopaminergic, i.e., capable of binding a dopamine receptor, may be determined according to methods known in the art. For example, dopamine receptors and receptor ligand binding assays are known in the at including at least assays for D1-like (D1A, D1B/D5), and D2-like (D2S, D2L, D3, D4) receptors using e.g., brain slices, brain region membrane preparations, isolated neuronal cells, cell lines, synaptosomal membrane preparations and cells stably transfected with dopamine receptors e.g., C-6 glioma cells stably transfected with rat cDNA encoding D2L or D3; CHO cells stably transfected with cDNA encoding rat D2S, D2L, D3 or D4; and the like. The binding interactions between a test compound and a dopamine receptor binding may be assessed e.g., using radio-labeled test compounds as ligands. Specificity of binding may be assessed by competition with known dopamine receptor ligands, e.g., the D1 antagonist SCH23390 [(R)-(+)-7-chloro-8-hydroxy-3-methyl-1-phenyl-2,3,4,5-tetrahydro-1H-3-benazepine] and the D2 antagonist haloperidol. Functionality of a test compound according to the invention as a dopaminergic agonist may, for example, be determined using rat striatal membrane preparations and modulation of second messengers sucb cAMP, calcium flux or 5'-O-(gamma-[$^{35}$S]thio) triphosphate ([$^{35}$S]-GTP gamma S) binding. e.g., according to methods such as those described in Geurts, et. al., 1999 and others. In vivo tests for assessing binding of test compounds to dopamine receptors include assays measuring tyrosine hydroxylase activity in mouse and rat brain where dopaminergic agonist-induced increases in enzyme activity which may be measured using conventional methodology (e.g., Kikuchi et al. 1995; Yasuda et. al., 1988). Antagonist activity of a test compound may also be evaluated using assay methods to measure reserpine and gamma-butyrolactone (GBL)-induced increases in tyrosine hydroxylase activity, i.e., the increase in activity is antagonized by D2 receptor antagonists such as haloperidol. Post-synaptic D2 receptor antagonist activity may be confirmed by increased locomotor activity in reserpine-treated mice, or by evaluating rotation in rats with unilateral 6-OH-dopamine lesions (Kikuchi t al., 1995).

Assays for determining that a test compound according to FORMULA I is capable of passaging the blood-brain barrier are also known. For example, a test compound according to the invention may be injected intravenously into test mice and passage of the blood-brain-barrier may be evaluated by measuring a brain penetration index (BPI), wherein the amount of test compound measured per gram of brain tissue is divided by the amount of test compound measured per gram of liver tissue. For comparison, the BPI value for gamma amino butyric acid (GABA) is about 1.0%. Ex-Vivo assays for determining blood brain barrier transport are also known, including e.g., an assay described recently by Duport et al., (1993) using in vitro organ culture to measure the likelihood that a test compound will passage the blood brain barrier. Briefly, in the latter assay slices of selected brain regions are overlaid onto an endothelial cell monolayer in vitro and allowed to form tight junctions over the course of about 10 days of culture. Test compounds are then perfused into the endothelial side of culture and blood brain barrier penetration is detected by measuring the levels of the test compound which enter into the organ slice.

Methods for assessing intestinal transport of a test compound (i.e., according to FORMULA I) we also known. For example, that a compound according to the instant invention is transportable by an intestinal saccharide transporter may be determined e.g., using the ex situ perfused everted rat small intestine (jejunum) model in a Ussing-type chamber, or alternatively, using everted intestinal sacs and rings. In the latter assays, transport of a test compound according to the invention is determined by applying the test compound to the everted luminal epithelium and measuring the amount of compound that reaches the opposite serosal side (e.g., see Mizuma et al., 1994; Diez-Sampedro et al., 1999). For ease of measurement, the subject test compound may be radiolabeled e.g., with $C^{14}$. That a sodium-dependent glucose co-transporter (SGLT1) is specifically involved in transport of a test compound according to the invention may be determined by removing sodium ions from the intestinal perfusate solution, (i.e., the subject saccharide transporter is Na+ dependent and the rate or amount transported in the absence of Na+ ions should decrease), or by adding phlorizin (i.e., an inhibitor of transport).

Methods for testing compounds to determine that they binding to and are transported by glucose co-transporters n vitro are also known, e.g., using isolated primary cultures of rat villus tip intestinal enterocytes and enterocyte-like cultures of HT-29 colon carcinoma cells. That a test compound according to the invention is transportable may be determined by adding the compound to the extracellular medium, washing the cells to remove non-specifically associated test compound cells (e.g., by centrifugation through isobutyl pthylate or Ficoll), and then measuring the amount of test compound which has entered the cells. Specificity of transport may be established, as above, by removing Na+ ions or adding phlorizin.

Saccharide transporter, as set forth above, is intended to mean a cellular membrane protein capable of binding a saccharide and transporting that saccharide from one location to another on/in the cell. Representative examples of saccharide transporters include glucose transporters (e.g., GLUT 1, 2, 3, 4 and 5), galactose transporters, mannose transporters, fructose transporters, arabinose transporters and the like. Those skilled in the art are cognizant of methods by which test compounds may be shown capable of binding to a saccharide transporter, examples of which are provided below.

"Brain penetration index", abbreviated BPI, is intended to mean the mathematical ratio calculated as the amount of one or more of the instant compounds in brain tissue per gram of brain tissue, divided by the amount of the compound (or compounds) in liver tissue per gram liver tissue. The liver being chosen as a reference organ because of its intimate contact with blood and relative lack of barriers. Measurements of BPI may be made for instance at 5-60 minutes after administration of a test compound, e.g., by oral, subcutaneous or intravenous routes. The subject mathematical ratio is commonly expressed as a percentage, i.e., by multiplying the ratio by 100%. This procedure has the advantage that even for a sparingly soluble lipophilic drugs, (which tend to remain largely at an injection site with slow diffusion into the circulation), the amounts of drug in the liver will reflect the actual amount which is systemically available and not the initial dose injected. Certain of the preferred compounds according to the instant invention have BPIs in the range of about 2% to about 500%, most preferred compounds have a BPI of about 10% to about 200%.

Methods for determining that a test compound according to FORMULA I, i.e., with a drug selected from TABLE A or TABLE B, is suitable for use in one or more of the instant methods, (i.e., for treating neurologic dysfunction or for use as a CNS-acting drug), are known to those skilled in the art of neuropsycopharmacology. For instance, the test compound may be evaluated in behavioral tests in experimental animals; e.g., to determine whether it exhibits one or more of the following: namely, a Pergolide-like dopaminergic activity, stimulation induced release of dopamine, locomotor activity in a murine test model, anticonvulsant activity, analgesic activity, cognition/memory, DAT transportability, activity in an MPTP-induced model of locomotor impairment.

"N-linked glycosyl prodrug", when used herein in regard to a pharmaceutical agent, is intended to mean an "A"-moiety CNS acting prodrug compound according to FORMULA I, linked through an amine or amide according to FORMULA I to a saccharide.

"Pharmaceutical composition", is intended to mean a composition containing one or more N-linked glycosyl CNS-acting prodrug compounds according to FORMULA I and a formulary effective to provide a dosage form suitable for administration to man or domestic animals. Representative examples of formularies and dosage forms so suitable are provided below.

"Formulary" is intended to mean an agent added to a pharmaceutical composition comprising said hydrophilic N-linked CNS acting prodrug compound. Representative examples of formulary agents include additives, stabilizers, carriers, binders, buffers, excipients, emollient water-in-oil and oil-in-water emulsions, disintegrants, lubricating agents, antimicrobial agents, preservative and the like; as disclosed further below.

"Dosage form" is intended to mean a form of a pharmaceutical composition suitable for administration to a subject in need thereof. Representative dosage forms include solids and liquids, e.g., perenteral and injection solutions, powders and granules, emollient creams, syrups and elixirs, nasal and ophthalmic drops, intrabronchial inhalants, timed-release capsules, lozenges, troches, suppositories, dermal patches, impregnated bandages and the like.

Embodiments of the invention provide pharmaceutical compositions, supra, containing one or more of the instant N-linked prodrug compounds in a form suitable for administration to man or domestic animals. Representative examples of forms so suitable include compositions in which the instant compound is in solid and liquid mixtures with optional additives, stabilizers, carriers, binders, buffers, excipients, emollients, disintegrants, lubricating agents, antimicrobial agents and the like. The instant pharmaceutical compositions are distinct, in that the instant compound comprising the active ingredient in the subject compositions has all of the following properties: namely, (i) it is transportable in an intact form by a saccharide transporter, e.g., as that receptor is expressed in nature in an intestinal cell or in a red blood cell; (ii) it is transportable in an intact form across the blood brain barrier by a saccharide transporter, i.e., as that transporter is expressed in nature in an endothelial cell; (iii) it is transportable by DAT; and, (iv) it is capable of binding to a dopaminergic receptor in a neural cell, i.e., as that receptor is expressed in nature in a neural cell.

"Intestinal cell" is intended to mean a columnar epithelial cell, e.g., a microvillus luminal cell, lining the small or large intestine, or lining the colon.

"Endothelial cell" is intended to mean a cell lining a blood vessel, e.g., a capillary cell or a cell of an artery or a vein.

"Neural cell" is intended to mean cells of the nervous system, including neurons, glial cells, Schwann cells and the like.

"Transportable in an intact form" is intended to mean that the subject instant compound is not an inhibitor of GLUT transporters, and is not substantially chemically altered during transport, e.g., it is not metabolized or converted to a glucuronide during transport, such that when the instant compound is transported from one side of a cell to the another side it remains substantially unchanged. "Substantially unchanged" means that only conservative modifications of certain $R_1$, $R_4$, $R_5$, $R_6$, $R_7$, $R_8$, $R_9$, $R_{11}$ or $R_{12}$ group substituents (supra) may occur during transport, e.g., removal of a halogen atom and replacement with a hydrogen, conversion of a hydroxyl to a methoxy (e.g., an —$OCH_3$ in an acetal or a hemiacetal) and the like.

In other embodiments, the invention provides pharmaceutical compositions containing one or more of the instant compounds in combination with optional stabilizers, carriers, binders, buffers, excipients, emollients, disintegrants, lubricating agents, antimicrobial agents and the like. For oral administration, the instant pharmaceutical compositions may be liquid, solid or encapsulated. For perenteral administration, the instant pharmaceutical compositions may be sterile liquids or solids may be provided in a form suitable for reconstitution, e.g., powdered or granulated.

The instant compounds may be administered alone or in combination with pharmaceutically acceptable carriers, in either single or multiple doses. Suitable pharmaceutical carriers may include inert solid diluents or fillers, sterile aqueous solutions, and various nontoxic organic solvents. The pharmaceutical compositions formed by combining the instant compound with the pharmaceutically acceptable carrier may then be readily administered in a variety of dosage forms such as tablets, lozenges, syrups, injectable solutions, and the like. These pharmaceutical carriers can, if desired, contain additional ingredients such as flavorings, binders, excipients, and the like. Thus, for purposes of oral administration, tablets containing various excipients such as sodium citrate, calcium carbonate, and calcium phosphate may be employed along with various disintegrants such as starch, and preferably potato or tapioca starch, alginic acid, and certain complex silicates, together with binding agents such as polyvinylpyrolidone, sucrose, gelatin, and acacia. Additionally, lubricating agents, such as magnesium stearate, sodium lauryl sulfate, and talc are often useful for tableting purposes. Solid compositions of a similar type may also be employed as fillers in salt and hard-filled gelatin capsules. Preferred materials for this purpose include lactose or milk sugar and high molecular weight polyethylene glycols. When aqueous suspensions of elixirs are desired for oral administration, the instant compound therein may be combined with various sweetening or flavoring agents, colored matter or dyes, and if desired, emulsifying or suspending agents, together with diluents such as water, ethanol, propylene glycol, glycerin, and combinations thereof. For parenteral administration, solutions of the instant compound in sesame or peanut oil or in aqueous polypropylene glycol may be employed, as well as sterile aqueous saline solutions of the corresponding water-soluble pharmaceutically acceptable metal salts previously described. Such an aqueous solution should be suitably buffered if necessary and the liquid diluent first rendered isotonic with sufficient saline or glucose. These particular aqueous solutions are especially suitable for intravenous, intramuscular, subcutaneous, and intraperitoneal injection. The sterile aqueous media employed are all readily obtainable by standard techniques well known to those skilled in the art.

It may prove desirable to stabilize the instant compounds e.g. to increase their shelf life and/or pharmacokinetic half-life. Shelf-life stability may be improved by adding excipients such as: a) hydrophobic agents (e.g., glycerol); b) non-linked sugars (e.g., sucrose, mannose, sorbitol, rhamnose, xylose); c) non-linked complex carbohydrates (e.g., lactose); and/or d) bacteriostatic agents. Pharmacokinetic half-life of the instant compounds varies depending upon the pyranosyl or furanosyl moiety selected, whether the saccharide units therein are multimeric, whether the multimer constitutes an oligosaccharide, and whether the multimers or oligosacharride are derivatized, i.e., chemically modified by methylation, sulfation, nitration and the like. Pharmacokinetic half-life and pharmacodynamics may also be modified by: a) encapsulation (e.g., in liposomes); b) controlling the degree of hydration (e.g., by controlling the extent and type of saccharide units); and, c) controlling the electrostatic charge and hydrophobicity of the saccharide units.

Pharmaceutically acceptable salts can be readily prepared from the instant compounds by conventional methods. Thus, such salts may be, for example, prepared by treating the instant compound with an aqueous solution of the desired pharmaceutically acceptable metallic hydroxide or other metallic base and evaporating the resulting solution to dryness, preferably under reduced pressure in a nitrogen atmosphere. Alternatively, a solution of the instant compound may be mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, furmarate, succinate, tartrate, and the like.

Freely-soluble salts of the instant compounds may also be converted to salts of low solubility in body fluids by modification with a slightly water-soluble pharmaceutically acceptable salt, e.g., tannic or palmoic acid, or by inclusion in a time-release formulation such as covalently coupled to a larger carrier, or in timed-release capsules and the like. In general, the acid addition salts of instant compounds with pharmaceutically acceptable acids will be biologically equivalent to the compounds themselves. Pharmaceutically acceptable salts can be readily prepared from the instant compounds by conventional methods. Thus, such salts are, for example, prepared by treating with an aqueous solution of the desired pharmaceutically acceptable metallic hydroxide or other metallic base and evaporating the resulting solution to dryness, preferably under reduced pressure in a nitrogen atmosphere. Alternatively, a solution of a compound is mixed with an alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosylate, citrate, maleate, furmarate, succinate, tartrate, and the like.

The preferred pharmaceutical compositions for inocula and dosage will vary with the clinical indication. The inocula may typically be prepared from a dried compound by suspending the compound in a physiologically acceptable diluent such as water, saline, or phosphate-buffered saline. Some variation in dosage will necessarily occur depending upon the condition of the patient being treated, and the physician will, in any event, determine the appropriate dose for the individual patient. The effective amount of the instant compound per unit dose depends, among other things, on the body weight, physiology, and chosen inoculation regimen. A unit does of the instant compound refers to the weight of compound (according to FORMULA I) without the weight of carrier (when carrier is used). Generally, the amount of active ingredient administered to a subject in need thereof according to the practice of the invention will be in the range of about 1 mg/day to about 2.5 gm/day. Single unit dosage forms and multi-use dosage forms are considered within the scope of the invention, as disclosed further below.

The instant pharmaceutically acceptable carriers may be formed, filled and sealed for ease of use. Representative forming, filling and sealing methods are known in the pharmaceutical ara. For instant, the instant compositions may be formulated with pharmaceutically acceptable carriers into pharmaceutical preparations suitable for inclusion in timed-release capsules, tablets, lozenges, syrups and the like.

Pharmaceutically acceptable salts may be prepared from the instant compounds by conventional methods. For example, such salts may be prepared by treating one or more of the instant compounds with an aqueous solution of the desired pharmaceutically acceptable metallic hydroxide or other metallic base and evaporating the resulting solution to dryness, preferably under reduced pressure in a nitrogen atmosphere. Alternatively, a solution of the instant compound may be mixed with a alkoxide to the desired metal, and the solution subsequently evaporated to dryness. The pharmaceutically acceptable hydroxides, bases, and alkoxides include those with cations for this purpose, including (but not limited to), potassium, sodium, ammonium, calcium, and magnesium. Other representative pharmaceutically acceptable salts include hydrochloride, hydrobromide, sulfate, bisulfate, acetate, oxalate, valarate, oleate, laurate, borate, benzoate, lactate, phosphate, tosulate, citrate, maleate, furmarate, succinate, tartrate, and the like.

The route of delivery of the instant compounds is determined by the disease and the site where treatment is required. For topical, intrathecal, intramuscular or intra-rectal application it may be desirable to apply the instant compounds as a salve, ointment or emollient pharmaceutical composition at the local site, or to place an impregnated bandage or a dermal timed-release lipid-soluble patch. For intra-rectal application, it may be desirable to apply the instant compounds as a pharmaceutical composition in a suppository. In other situations, it may prove desirable to administer the compositions by intranasal or intrabronchial instillation (e.g., as a pharmaceutical composition suitable for use in a nebulizer), or gastrointestinal delivery (e.g., with a capsule, tablet, trouch or suppository). In one preferred embodiment, the instant pharmaceutical compositions are administered via suppository taking advantage of saccharide transporters in the colon for transport of the instant compound into the blood stream in a timed-release type manner for metabolic replacement therapy in patients with Parkinson's and related diseases.

The instant compounds find use in treatment of a variety of pathological central and peripheral nervous system dysfunctions, neuromotor conditions and cardiovascular diseases in subjects in need of treatment. For example, the subject conditions include, but are not limited to, i) toxic dystrophy, (e.g., chemical or drug-induced secondary dystrophy in the nervous system), ii) vascular impairment e.g. resulting in damage to nervous tissues, iii) central nervous system degeneration or peripheral nerve degeneration, iv) nervous system lesions induced by physical trauma, v) nervous system complications of illnesses and infections (e.g., viral or bacterial); and vi) hereditary nervous system impairment. Representative illness, diseases, and conditions having neurologic dysfunction have been classified and codified ("International Classification of Diseases, Washington D.C., 1989). Representative examples of subjects in need of treatment may include humans and domestic animals having e.g., a condition of hyper- or hypo-dopaminergic activity, such as may be evident in a patient with schizophrenia, Parkinson's disease, epilepsy, locomotor deficiency, hyperprolactinemia, Tourette's syndrome, Huntington's disease, psychosis, chronic psychiatric illness with amotivation, apathy, asociality, psychomotor adverse effects of drugs of abuse (e.g., cocaine, amphetamine, neuroleptics), subolivopontocerebellar atrophy (sOPCA), multiple system atrophy (MSA), bipolar disorder, chronic alcoholism, cocaine abuse, mood disorders, attention deficit disorder, physiologic stress, pesticide exposure (e.g., organochlorine insecticides), juvenile neuronal ceroid lipofuscinosis (JNCL), detached personality syndromes (as e.g. determined using the Karolinska Scales of Personality questionnaire) and the like. Representative examples of conditions exhibiting hyper-dopaminergic activity include schizophrenia, chronic psychiatric illness with hallucinations and delusions. Also representative are, patients with coronary hypertension, angina, ischemic myocardium and the like. In addition, prophylactic methods are envisaged for lowering aortic and pulmonary artery pressure during and after coronary bypass surgery and liver, kidney and heart transplant surgery. Vasodilation mediated by the instant compounds is without impairment of oxygen delivery or impairment of intrinsic neural or hormonal control systems.

"Parkinson's related disease", as used herein, is intended to mean a disease characterized by one or more symptoms which are also evidenced clinically in a patient with Parkinson's disease. Representative examples of symptoms evidenced in patients with Parkinsonism include seizure, loss of neuromotor control of muscle movements, tardive dyskinesia, Alzheimer's disease, Wilson's disease, post-encephalitic syndromes, Parkinsonism secondary to trauma and stroke, dementia, Lou Gehrig's disease, psychomotor retardation, schizophreniform behavior, anxiety and depression. Clinical features of Parkinson's related diseases are disclosed in Hurtig, 1997, incorporated herein by reference in its entirety.

"Metabolic replacement therapy", as used herein, is intended to mean that the instant compound, when administered in the instant pharmaceutical composition, is effective, following transport into a neural cell, to satisfy one or metabolic requirements of catecholamine synthesis in the neural cell of a subject having a nigrostriatal dopamine insufficiency. Representative examples of compounds so capable include derivatives of L-Dope, e.g., Levodopa.

The routes and methods for delivery of the instant preparations are determined by the particular disease. Disclosure of therapeutic methods of treating disease appear in Applicants co-pending U.S. patent application Ser. Nos. 10/274,798, 10/198,798 and 09/547,501, incorporated herein by reference in their entirety.

In yet other embodiments, the special aqueous solubility of the instant prodrug compounds provides novel pharmaceutical compositions containing relatively high concentrations of active ingredients (e.g., up to 500 mg/ml) included in relatively small volumes (e.g., up to about 500 mg/ml), allowing administration of relatively small volumes of therapeutically effective unit doses. The latter attribute of the instant compounds is a particular advantage in the instant pharmaceutical compositions, i.e., especially in multi-dose, time-release, subcutaneous and intradermal, buccal, trouch, and suppository preparations. The subject attributes may also be especially useful for achieving steady state plasma levels in a subject in need thereof. Where conventional methods of administration are ineffective in certain patients, the subject high solubility attributes of the instant compounds make it feasible to administer metabolic replacement therapy via an implantable mini-pump such as those used for delivery of insulin in patients with Type 1 insulin-dependent diabetes mellitus.

Non-limiting illustrative preparations and formulations are disclosed in the EXAMPLES, section which follows.

Example 1

Preparation of Dopamine Gluconamide

Scheme 1

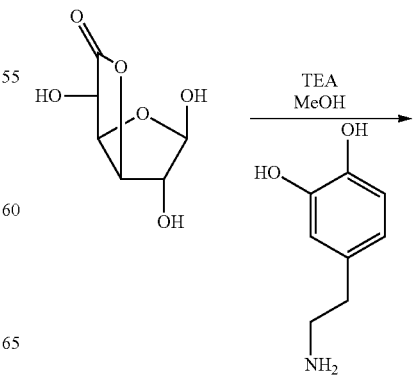

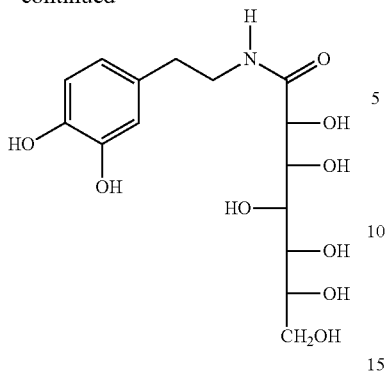

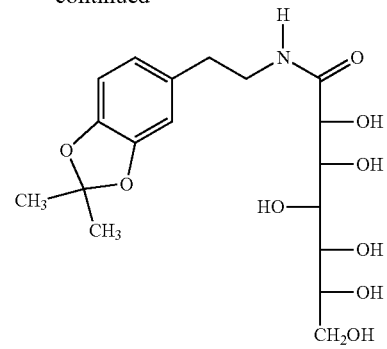

Gluconolactone (1.9 gm, 10.5 mmol) and triethylamine (TEA; 1.1 gm, 10.5 mmol) were added to methanol (25 mL) in a 100 mL round bottom flask with stirring. The gluconolactone was allowed to dissolve. When the solid was dissolved, the solution was stirred for an additional 10 minutes and then 3-hydroxytyramine (2.0 gm, 10.5 mmol) was added slowly, i.e., allowing it to dissolve. The reaction mixture was stirred in the dark for about 2 hrs. during which time a white solid precipitant appeared. The white solid precipitant was collected by filtration, washed with methanol (5 mL) and dried in vacuo for 6 hrs. to give dopamine gluconamide (1.69 gm, 5.10 mmol, 48.6% yield). Melting point of the synthesis product was 154-155° C. Predicted: $C_{14}H_{21}N_1$ (331.32): C, −50.75%; H, −6.39%; N, −4.23%; analysis results of synthetic product: C, 50.65; H, 6.63; N, 4.44.

Dopamine gluconamide (EXAMPLE 1, supra; 0.75 gm, 2.26 mmol) was added to acetone (40 mL) in a 100 mL round bottom flask with stirring. Them, the reaction mixture was refluxed for 2 hrs., after which time it was allowed to cool to room temperature (about 22-25 C). The resultant white solid was removed by filtration and dried in vacuo for 7 hrs. yielding the isopropylidine protected dopamine gluconamide (0.68 gm, 1.83 mmol, 81.0% yield). Melting point of the synthesis product was 170° C.

Example 3

Reduction of Isopropylidine Protected Dopamine Gluconamide

Scheme 3

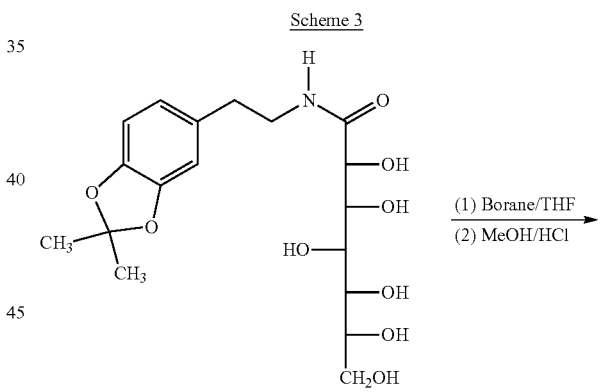

Example 2

Protection of Aromatic Dopamine Hydroxyl Residues

Scheme 2

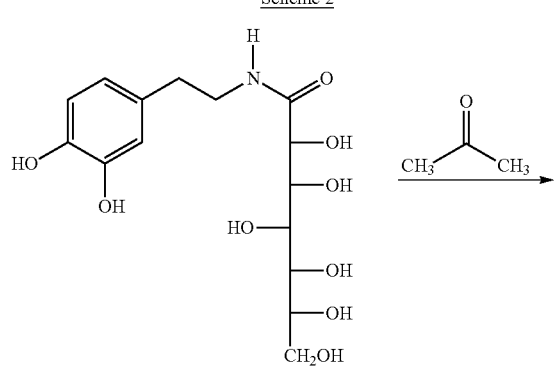

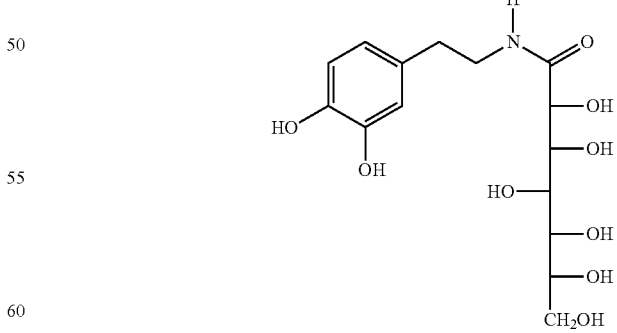

Isopropylidene protected dopamine gluconamide (EXAMPLE 2, supra; 0.68 gm, 1.83 mmol) was slowly added to a 1 M Borane solution in THF (25 ml) in a 100 mL round bottom flask, with stirring. The reaction mixture was refluxed for 2 hrs. and then allowed to cool to room temperature.

Excess solvent was removed by rotary evaporation. Methanolic HCl was added to the resultant residue and the solution refluxed for 2 hrs., after which time solvent was removed by evaporation and the solid recrystallized using a mixture of acetonitrile and ethanol. The recrystallized reduced dopamine gluconamide product was dried in vacuo for 6 hrs giving the dopamine gluconamine-HCl salt (0.22 gm, 0.62 mmol, 33.8% recovery). Melting point for the synthesis product was 151-152° C. Predicted $C_{14}H_{24}N_1$ (353.80); C, 47.53; H, 6.84; N, 3.96; Analysis result of synthesis product: C, 47.48; H, 6.93; N, 3.88.

Example 4

Preparation of Dopamine Ribonamide

D-(+)-Ribonic acid gamma-lactone (2.0 gm, 13.5 mmol) was added to methanol (25 mL) in a 100 mL round bottom flask with stirring until dissolved, and then an additional 5 min. 3-Hydroxytyramine (2.6 gm, 13.5 mmol) was added slowly, allowing it to dissolve, with stirring, over the course of about 10 minutes. Triethylamine (1.4 gm, 13.5 mmol) was then added and the reaction mixture refluxed for 4 hr. in the dark, during which time the solution acquired a slight yellow color. Solvents were removed by rotary evaporation using anhydrous ethanol as an azeotrope to remove any residual water. The resultant dried product constituted a thick syrup which solidified upon standing (1 hr.) to give a white solid. The white solid product was stirred (1 hr.) with acetone (40 mL), again resulting in a white solid as a product. The resultant solid was collected by filtration and dried in vacuo for 6 hrs. yielding dopamine ribonamide (3.83 gm, 12.7 mmol, 94.1% yield.) $^1$H and $^{13}$C-NMR results and CHN analyses were consistent with structure. Molting point was 90-91° C. Predicted $C_{13}H_{19}N_1$: (301.30): C, 51.82; H, 6.36; N, 4.65; Analysis results of synthesis product: C, 51.67; H, 6.40; N, 4.69.

Example 5

Preparation of Dopamine Isopropylidine Ribonamide

Aromatic hydroxyl groups in dopamine ribonamide were protected by synthesizing the isopropylidine compound. Dopamine ribonamide (EXAMPLE 4; 1.0 gm, 3.32 mmol) was added to acetone (30 mL) in a 100 mL round bottom flask with stirring. The reaction mixture was refluxed for 5 hrs. and then allowed to cool to room temperature. The resultant white solid was collected by filtration and dried in vacuo for 7 hrs. to yield the isopropylidine protected dopamine ribonamide (0.99 g, 2.90 mmol, 87.6% yield). $^1$H and $^{13}$C-NMR results were consistent with structure. Melting point was found to 142-143° C.

Example 6

Reduction of Isopropylidine Protected Dopamide Ribonamide Yielding Dopamine Ribonamine Isopropylidine-protected dopamide ribonamide (EXAMPLE 5; 0.70 gm; 2.05 mmol) was added slowly to 1 M Borane in THF (25 mL) in a 100 mL round bottom flask with stirring. The reaction mixture was refluxed for 2 hr. and allowed to cool to room temperature. Excess solvent was removed by rotary evaporation and methanolic HCl was added to the resulting residue. The resuspended residue was refluxed for 2 hr. and solvent was then evaporated yielding a thick hygroscopic syrup (complicating melting point analysis). The syrup was dried in vacuo for 6 hrs. to give the dopamine ribonamine-HCl salt as product (0.20 gm., 0.62 mmol, 30.3% yield.) $^1$H and $^{13}$C-NMR results were consistent with structure.

Example 7

Ready Solution for Administration as a Measured Dose

An illustrative ready solution for administration as a measure dose was prepared according to the formulation of TABLE A, below.

TABLE A

| Component: | Amount: |
|---|---|
| Compound #1 or #2* | 2.5 gm |
| Methyl-p-aminobenzoic acid | 0.014 gm |
| Propyl-p-aminobenzoic acid | 0.020 gm |
| Saccharin sodium | 0.050 gm |
| Flavoring agent | 0.001 gm |
| Citric acid | 0.200 gm |
| Sodium citrate | 0.320 gm |
| Distilled water USP q.s. to | 100 ml |

*Compound #1, Dopamine gluconamide (EXAMPLE #1, supra); Compound #2, Dopamine gluconamine.

Example 8

Powder Composition for Reconstitution Prior to Use

An illustrative powder composition for reconstitution prior to use was prepared according to the formulation of TABLE B, below.

TABLE B

| Component: | Amount: |
|---|---|
| Compound #1 or #2* | 2.5 mg |
| Sodium citrate | 20.0 mg |
| Sorbitol | 2.0 mg |
| Flavoring agent | 0.1 mg |
| Distilled water USP for reconstitution: | 10.0 ml |

*Compound #1, Dopamine gluconamide (EXAMPLE #1, supra; Compound #2, Dopamine gluconamine.

Example 9

Tablets for Oral Administration

An illustrative tablet for oral administration was prepared according to the formulation of TABLE C, below.

TABLE C

| Component: | Amount: |
|---|---|
| Compound #1 or #2* | 250 mg |
| Starch | 17 mg |
| Sodium glycolate (starch) | 40 mg |
| Polyvinal pyrrolidene | 7.0 mg |
| Microcrystalline cellulose | 45 mg |
| Magnesium sterate | 2.0 mg |

*Compound #1, Dopamine gluconamide (EXAMPLE #1, supra); Compound #2, Dopamine gluconamine.

Example 10

Tablet for Sublingual Administration

An illustrative tablet for sublingual administration was prepared according to the formulation of TABLE D, below.

TABLE D

| Component: | Amount: |
|---|---|
| Compound #1 or #2 | 250 mg |
| Gum arabic | 10 mg |
| Lactose | 90 mg |
| Ammonium glycyrrhiznate | 20 mg |
| Sodium saccharin | 2 mg |
| Flavor | 10 mg |
| Magnesium sterate | 7 mg |

*Compound #1, Dopamine gluconamide (EXAMPLE #1, supra); Compound #2, Dopamine gluconamine.

Example 11

Dopamine Receptor Binding

To illustrate biological activity, i.e., dopaminergic activity, and putative pharmaceutical utility, dopamine receptor binding activity of Compounds #1 (EXAMPLE 2, product) and Compound #2 (EXAMPLE 3, product) was tested in vitro using COS-7 cells transiently transfected with pCD-PS expression vectors containing human D1, human D5 and human D2 (long) inserts, i.e., according to Materials and Methods disclosed further below. Binding to dopaminergic receptors was tested as ability to compete binding of specific receptor ligands (i.e., [$^3$H]-SCH-23390 for D1; [$^3$H]-emonapride for D2), as well as, the ability to trigger intracellular second messengers, i.e., cAMP.

Competition binding assays were initiated in duplicate with 0.5 ml aliquots of membrane preparations from cell cultures transfected with cDNA encoding human D1- or D2-receptors. Test compounds (Compounds #1 or #2, supra) were added as competitors to achieve a final concentration in the assay in the range of $10^{-4}$M to $10^{-11}$ M. As binding ligand, [$^3$]-SCH-23390 (a D1-selective agonist) or [$^3$H]-Emonapride (a D2-selective agonist) was added to each assay. After 90 minutes incubation at room temperature the assay was terminated by rapid filtration and membrane bound [$^3$H] was determined by scintillation spectrometry.

Test Compounds #1 and #2 successfully competed [$^3$H]-SCH-23390 binding to dopamine receptors in cells transiently expressing receptors, i.e., in a dose-response and uniphasic type manner. Under these particular conditions of assay, the illustrative test Compounds #1 and #2 showed selectivity for D5-over D1-receptors, i.e., a property held in common with natural dopamine agonist.

Agonist functional activity assays were conducted by evaluating ability of test compound to trigger production of second messengers in dopamine receptor transfected COS-7 cells, i.e., cAMP. Incubation with test compound (or dopamine as a positive control) were conducted at 37° C. (5% $CO_2$) for 15 min. and cAMP accumulation was determined by radioimmunoassay. For comparison, dopamine as a positive control stimulated accumulation of cAMP by about 5-fold in D1-transfected cells and about 3-fold in D5-transfectants. In dopamine receptor transfectants, Compound #2 stimulated cAMP accumulation in a dose-response manner to levels near those achieved in dopamine control cultures. Co-incubation of dopamine with Compound #2 did not reduce the levels of cAMP accumulation recorded, suggesting strongly that the compounds produced according to the instant methods act as agonists, not antagonists.

Example 12

Dopamine Transporter Binding Activity

To further illustrate biological activity, i.e., transportability within the brain, Compounds #1 and #2 (supra) dopamine transporter (DAT) binding activity of Compounds #1 and #2 was evaluated by measuring their ability to compete uptake of $^3$H-labeled dopamine by human DAT-transfected cells over the course of a 5 hour incubation period. To obtain differing levels of DAT expression, cells were transiently transfected) with plasmids containing a DAT cDNA insert (hDAT), or alternatively, control irrelevant cDNA insert (Negative Control, NC). After 48-72 hrs. culture, dopamine transport was measured in the transiently transfected hDAT-cells by incubation for 5 hrs. in the presence of $^3$H-labeled dopamine (Positive Control, PC). Competition of $^3$H-dopamine uptake was observed with both Compound #1 and Compound #2.

Example 13

Parkinson's Animal Model Studies

Study #1: Anti-Parkinson's Effect in MPTP-Lesioned Mice

Dopaminergic neurotoxin 1,2,3,6-methyl-phenyl-tetrahydropyridine (MPTP) is a chemical contaminant first found in contaminated synthetic street heroin. This chemical produces Parkinsons-like neuropathological changes and clinical features in man, monkey and mice. Like the natural dopamine mediator, MPP$^+$ is taken up into the dopaminergic nigral terminal by dopamine transporters (DAT) with resultant cellular changes similar to those mitochondrial complex I defects found in Parkinson's Disease. MPTP-treated mice are one accepted Parkinson's-like animal models.

The first phase of the project involved testing to measure anti-Parkinson's effects of COMPOUND #1 in an MPTP-mouse model of nigral injury. Experimental mice were lesioned with MPTP (i.e., 40 mg/kg, ip twice, 1 month).

FIG. 1. MPTP treatment significantly reduced the Rota-Rod mean time—i.e., by over 65%. Rota-Rod performance times of C57BL/6 mice before and after lesioning with MPTP, or as a negative control, NaCl.

Figure 2:
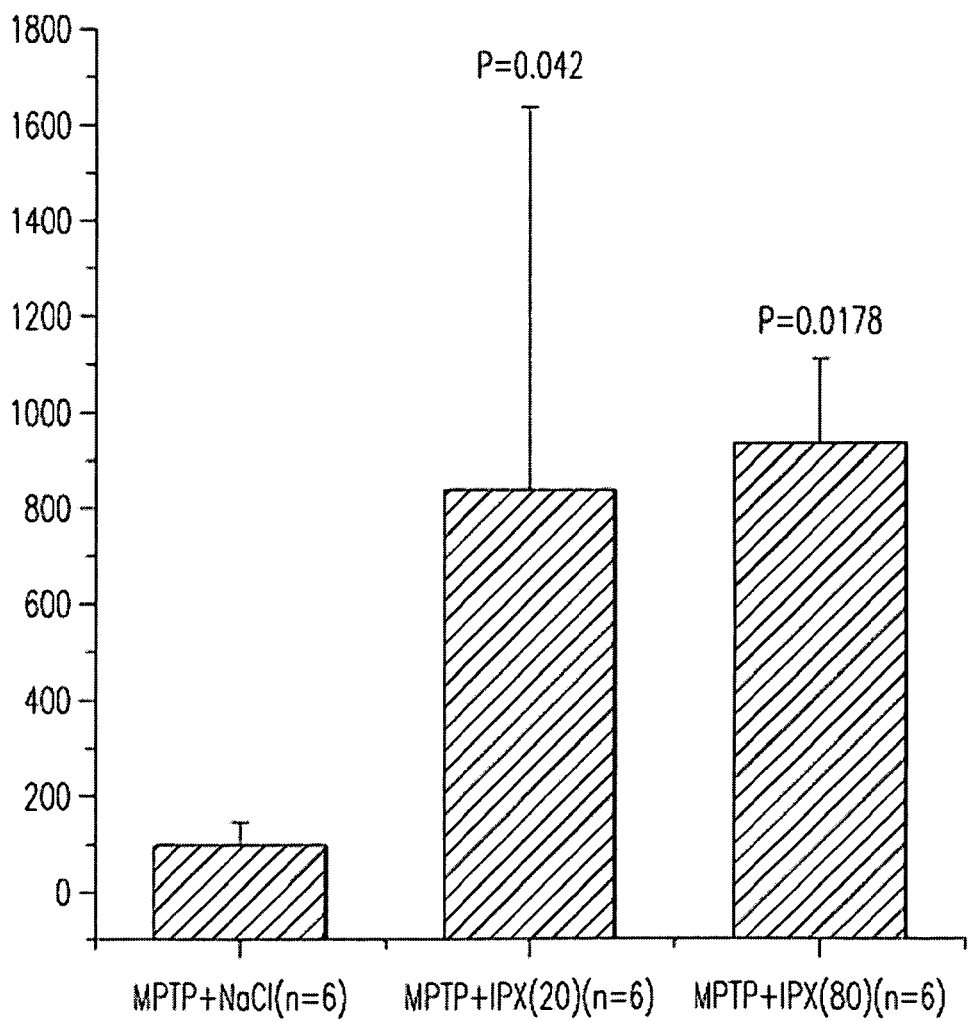
FIG. 2. MPTP-lesioned mice (FIG. 1) were treated with COMPOUND #1 twice daily and tested for Rota-Rod performance times at weekly intervals as depicted graphically in the figure and set forth further in regard to EXAMPLE 13, below.

FIG. 2. MPTP-lesioned mice were treated with COMPOUND #1 twice daily (20 mg/kg or 80 mg/kg) and tested at weekly intervals. The results presented show improved Rota-Rod performance times at the fourth week of COMPOUND #1 treatment, i.e., 8-9 fold better than NaCl-treated controls (p<0.05). Rota-Rod performance of MPTP-lesioned mice after four weeks of treatment with either 20 mg/kg or 80 mg/kg COMPOUND #1 or, with vehicle control (0.9% NaCl). Both treatment groups showed statistically significant increases (p<0.05) in the Rota-Rod times. (Y-axis: time in seconds).

Figure 3:
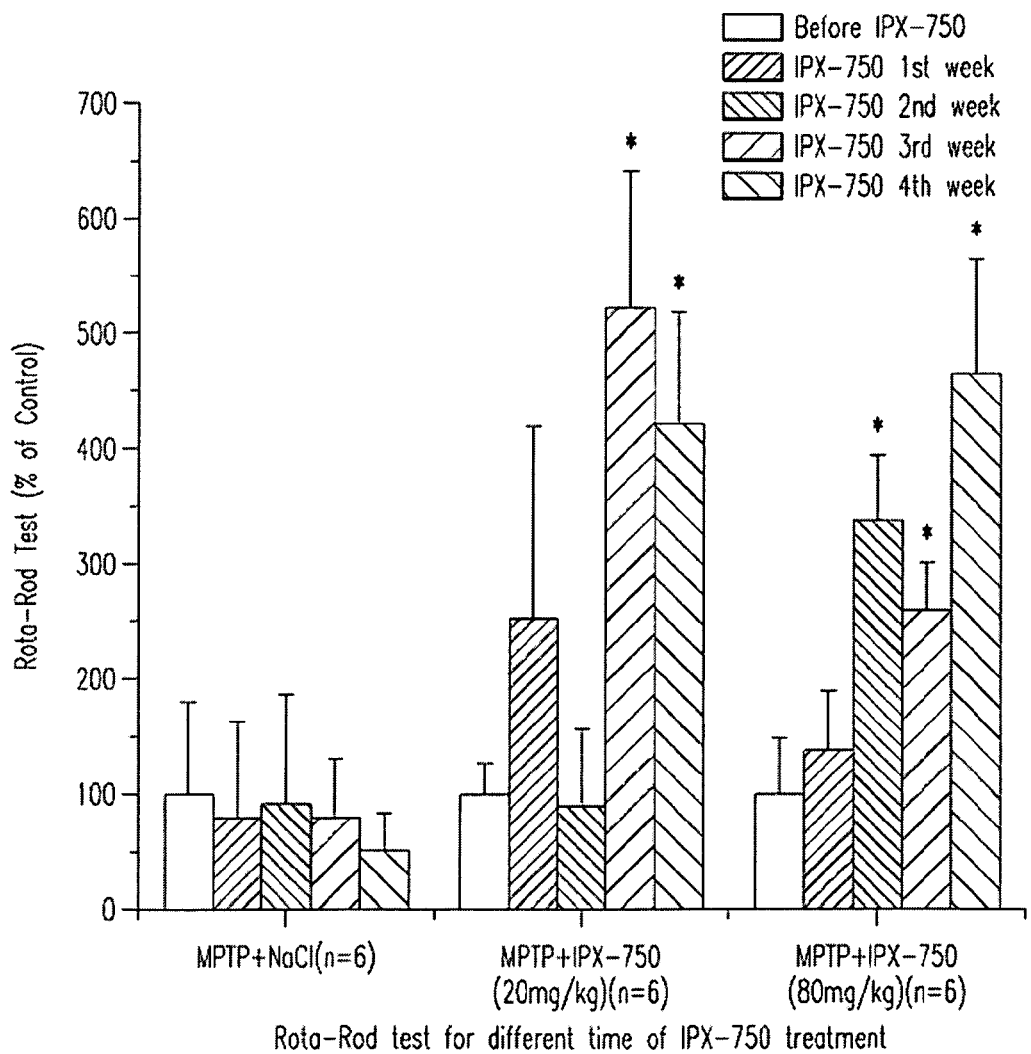
FIG. 3. Significant improvements in Rota-rod performance times were observed in COMPOUND #1-treated MPTP-leisioned mice (FIG. 1), i.e., as depicted graphically in the figure and set forth further in regard to EXAMPLE 13, below. ($*p<0.05$.)

FIG. 3. Significant improvements in Rota-rod performance times were observed in COMPOUND #1 treated animals beginning at about the third week of treatment at a dose of 20 mg/kg, and at about the second week at the higher dose of 80 mg/kg. Kinetics of onset of anti-Parkinsons therapeutic effects on COMPOUND #1 treatment. MPTP-lesioned mice treated daily at 20 mg/kg or 80 g/kg COMPOUND #1, or vehicle control (0.9% NaCl). Rota-Rod times were statistically different from control at 3-4 wks. In the 20 mg/kg treatment group; and 2-4 wks. in the 80 mg/kg treatment group. (*p<0.05.)

Figure 4:
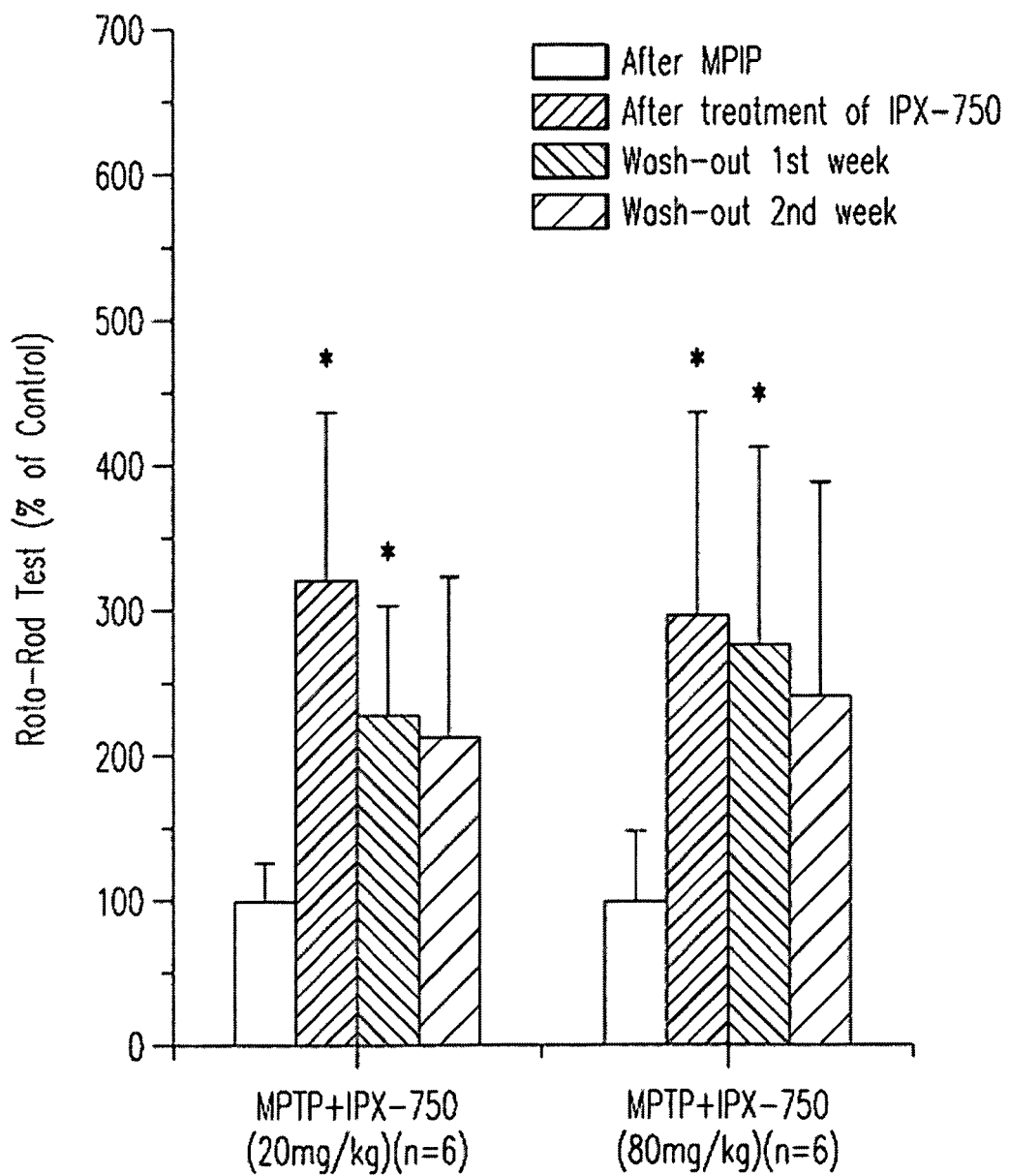
FIG. 4. 'Washout' experiments to determine how long therapeutic effects remained evident after cessation of COMPOUND #1 therapy in MPTP-leisioned mice, i.e., as as depicted graphically in the figure and set forth further in regard to EXAMPLE 13, below. ($*p<0.05$).
Figure 7:
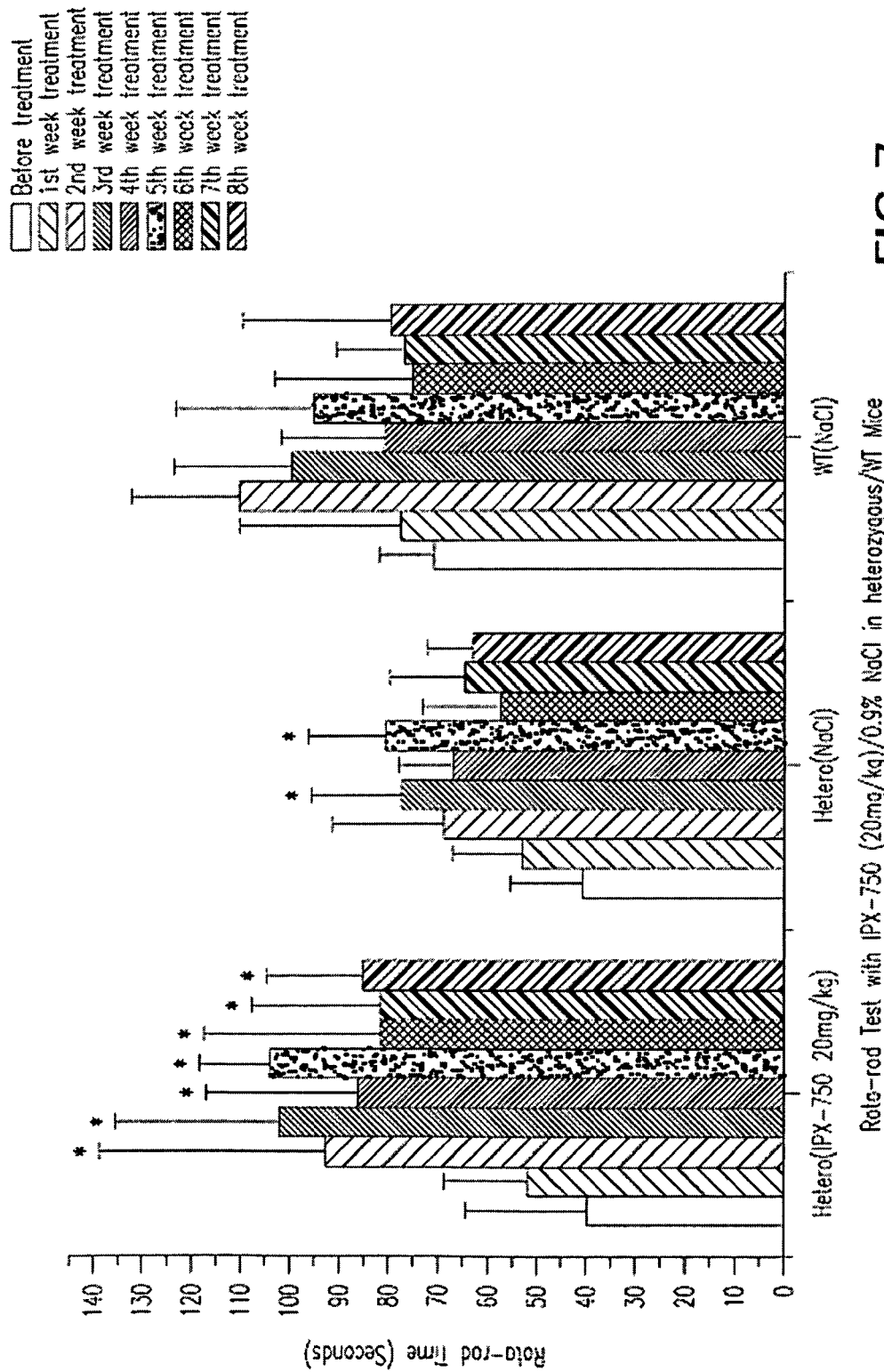
FIG. 7. Nurr1 genetically deficient stem-cell knockout mice were treated with COMPOUND #1 or saline and observed weekly for RotoRod performance (time) as depicted graphically in the figure and set forth further in regard to EXAMPLE 15, below. $*p<0.05$.

FIG. 4. 'Washout' experiment to determine how long therapeutic effects remained evident after cessation of COMPOUND #1 therapy. MPTP-lesioned mice were treated for 4 wks. At either 20 mg/kg or 80 mg/kg and then left untreated for an additional 1 or 2 wks. The results presented in FIG. 7 show a gradual return of symptoms in the MPTP-lesioned mice (i.e., a decrease in Rota Rod performance), but therapeutic effects of COMPOUND #1 were still evident in these animals even after a two-week washout time period. Washout of COMPOUND #1 therapeutic effects in MPTP-lesioned mice left untreated for an additional 1 or 2 weeks. (Clear bar: MPTP-lesioned/no therapy $2^{nd}$ bar: MPTP-lesioned/4 wks. therapy with COMPOUND #1). (*p<0.05).

CONCLUSIONS: The data indicate that COMPOUND #1 possesses anti-Parkinsons effects in MPTP-lesioned mice and that COMPOUND #11 when administered at 20 mg/kg exhibits similar efficacy to when it is administered at 80 mg/kg.

DISCUSSION: A discussion of the animal model data is presented in EXAMPLE 17, below.

METHODS: Rota-Rod performance measures the length of time each animal manages to maintain its balance on the rotating lucite rod. Prior to MPTP-lesioning animals, the performance was conditioned in three training sessions. The general training and testing procedure was as follows: namely, Animals were placed on a stationary rod for 30 sec to accustom the behavior and establish familiarity with the environment. During this time if an animal fell, it was placed back on the rod; Next, animals were conditioned (or tested) at a constant speed of 5 rpm for 90 sec.;

Any animal that failed a first test was re-tested two more times; Any animal that failed a third test at 5 rpm was removed from the experiment; Thirty-minutes (30 min) after the last 5 rpm trial, each animal was placed back on the rod the speed was increased to 10 rpm; The length of time that each animal was able to maintain balance on the rod was measured at the constant speed of 10 rpm, i.e., data collection.

Example 14

Parkinson's Animal Model Studies

STUDY #2. Effects of IPX750 in 6-OHDA-Lesioned Rats

Effects of COMPOUND #1 were next tested in a 6-OHDA-induced nigral-injury model in SD rats. Anti-Parkinson's effects of COMPOUND #1 were tested by measuring rotational behavior ('spinning' or circular wandering) of rats Induced by apomorphine, i.e., as measuring using a Rota-Count-8 unit (Columbus Instruments). In this animal model, Parkinsons-like symptoms similar to the human condition are produced by treating animals with 6-OHDA, a dopamine-depleting drug. The nigral dopamine depletion is induced by using unilateral injections of 6-OHDA directly into the nigrostriatal system (AP: −4.4 mm, ML: 1.1 mm, DV: 7.5 mm, AP: −4.0 mm, ML: 0.8 mm, DV: 7.8 mm). As a result of the 6-OHDA dopamine depletion dopaminergic receptors in post-synaptic terminals are 'hyper-sensitized' to the action of dopaminergic compounds. Thus, animals treated with 6-OHDA having the unilateral lesion will exhibit an uncontrolled 'spinning', circular wandering and other rotational behaviors after the administration of apomorphine and certain other dopaminergic agonists.

Figure 5:
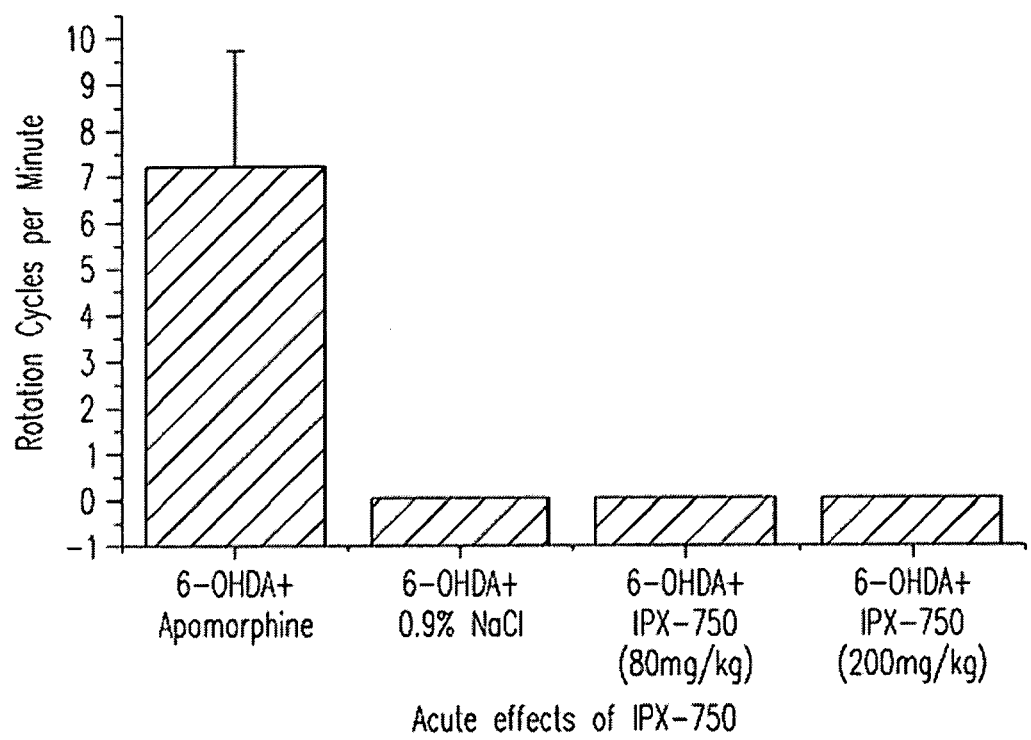
FIG. 5. The effects of COMPOUND #1 were tested in the 6-hydroxydopamine (6-OHDA) rat nigrostriatal-leision model and rotational behavior induced by apomorphine, i.e., as depicted graphically in the figure and set forth further in regard to EXAMPLE 14, below.

FIG. 5. The possible agonist effects of COMPOUND #1 were tested at 80 mg/kg and 200 mg/kg in this 6-OHDA model. Like dopamine, administration of IPX750, at either 80 mg/kg or 200 mg/kg, did not trigger visible effects in this animal model.

To investigate the effects of COMPOUND #1,6-OHDA-lesioned rats were treated with COMPOUND #1 at 5 mg/kg or 20 mg/kg daily for 4 weeks and the rotational response of the animals to apomorphine was tested at weekly intervals. Rotation in 6-OHDA-unilateral-lesioned rats: Comparing apomorphine-induced rotation after treating with COMPOUND #1 at 80 mg/kg or 200 mg/kg.

Figure 6:
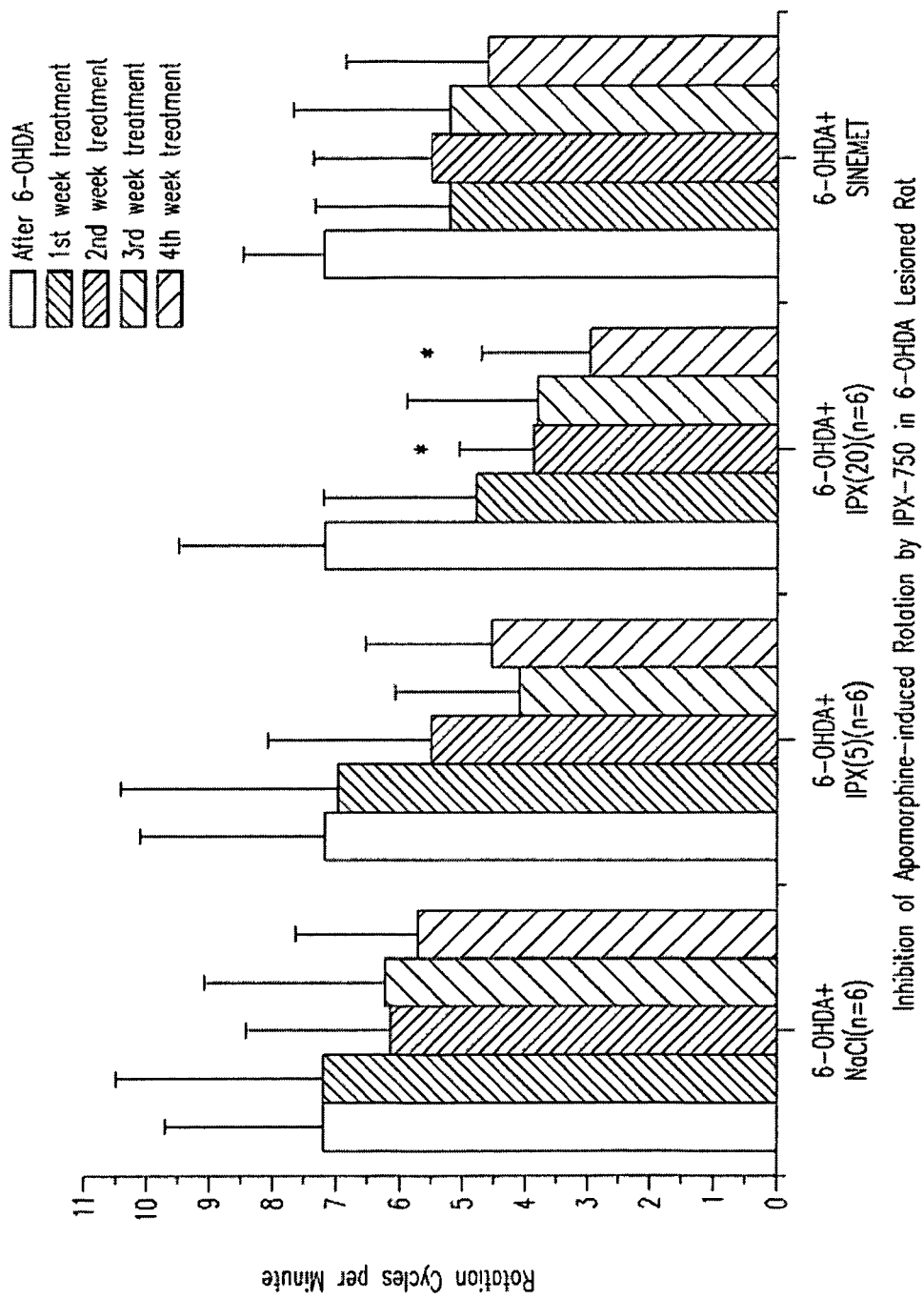
FIG. 6. Treatment of 6-OHDA leisioned rats (FIG. 5) with COMPOUND #1 significantly decreased apomorphine-induced rotation in 6-hydroxydopamine-leisioned animals, i.e., as depicted graphically in the figure and set forth further in regard to EXAMPLE 14, below. ($p<0.05$).

FIG. 6. The results show that COMPOUND #1 treatment at 20 mg/kg significantly decreased apomorphine-induced rotation. Animals in the vehicle control group (receiving only 0.9% NaCl) did not show this decreased responsiveness to apomorphine. COMPOUND #1 at 5 mg/kg or 20 mg/kg in comparison with SINEMET (20 mg/kg): Effect on apomorphine-induced rotation; at 20 mg/kg (p<0.05).

CONCLUSIONS: The data indicate COMPOUND #1 (20 mg/kg) possesses anti-Parkinson's effects in 6-OHDA lesioned rats.

DISCUSSION: A discussion of the animal model data is presented in EXAMPLE 17, below.

METHODS for STUDY #2: The Rota-Count 8 unit is an eight channel rotational meter. The system utilizes a digital rotary encoder and each encoder is mounted in a small bowl with a cable attachment; thereby, rotations of rats are automatically recorded. 6-OHDA in 0.9% NaCl at a concentration of 0.2% (w/v)-8 μl injected into the nigrostriatum. To control for injection failures in the injections, only 6-OHDA-lesioned rats that rotated more than 5 cycles/min at 7 days post-injection were selected for experimental use. Treatments ip with COMPOUND #1 or SINEMET administered twice daily 2-wks. after 6-OHDA.

Example 15

Parkinson's Animal Model Studies

STUDY #3. Effects of IPX750 in Nurr1 Genetic-Knockout Mice

Genetic knockout mice having defective expression of the Nurr1 gene exhibit age-related selective agenesis at dopaminergic neurons in the midbrain, i.e., similar to the genetic defects observed in patients with Parkinsons disease. Possible anti-Parkinson's effects of COMPOUND #1 were observed in Nurr1 deficient mice at an age when locomotor activity was first determined to be significantly defective (Clear bars, FIG. 10) in comparison with similarly aged wild type (WT, FIG. 7) mice, i.e., in Rota Rod measurements. Treatments consisted of twice daily administration of 20 mg/kg COMPOUND #1, or as a control, saline. Rota rod performance measurements were made on a weekly basis during an 8 week treatment period. Performance of COMPOUND #1 treated animals was significantly improved, i.e., about 2-fold to near WT performance times, relative to saline treated controls within just two weeks of treatment and performance of treated animals remained stable during the course of the 8-week treatment study (FIG. 7).

FIG. 7. Nurr1 genetically deficient mice treated with COMPOUND #1 or saline were observed weekly for RotoRod performance (time). Before treatment, RotaRod times showed a significant decrease in Nurr1 deficient mice compared with WT mice. Nurr1 deficient mice treated with COMPOUND #1 (20 mg/kg) showed significant increase of Rota-Rod time within two weeks of treatment, i.e., a statistically significant increase in performance when compared with pretreatment performance times. *p<0.05.

To determine the washout kinetics for COMPOUND #1, treatment was terminated at the 8$^{th}$ week and RotaRod performance measurements of mice were made in each of the successive three weeks.

Figure 8:
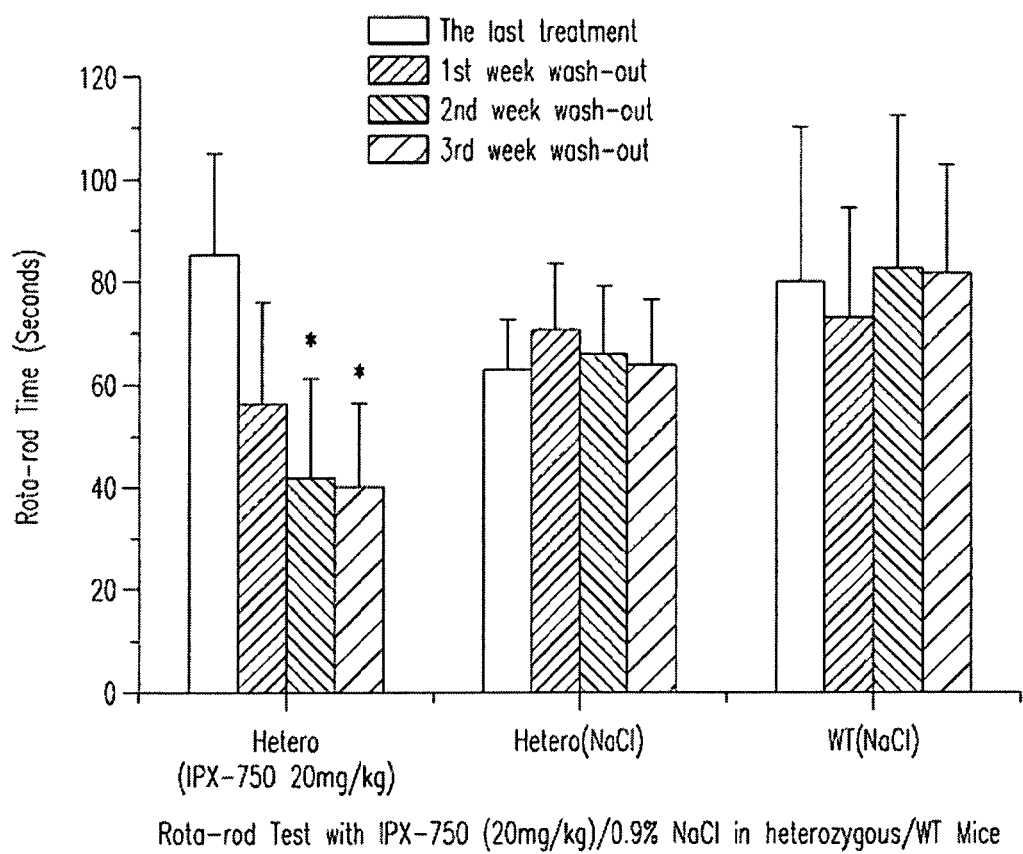
FIG. 8. Washout of COMPOUND #1 treatment in Nurr1 deficient mice as evidenced by returining disability in the Rota-Rod performance time measurements (FIG. 1) of animals after removal of therapy, i.e., as depicted graphically in the figure and as set forth further in regard to EXAMPLE 15, below. *p<0.05.

FIG. 8. Washout of COMPOUND #1 treatment in Nurr1 deficient mice. Rota-Rod performance measurements were performed over three successive weeks following cessation of COMPOUND #1 treatment. Rota-Rod performance degraded significantly within one week and returned to pretreatment values within 2 weeks. *p<0.05.

CONCLUSIONS: The data indicate COMPOUND #1 (20 mg/kg) possesses anti-Parkinson's effects in Nurr1 deficient mice.

DISCUSSION: A discussion of the animal model data is presented in EXAMPLE 17, below.

MATERIALS AND METHODS: RotaRod performance measurements (time that balance was maintained on the rod) were performed (as in Study #1), each week during 8 weeks of treatment. After RotaRod testing, COMPOUND #1 (20 mg/kg) was administered twice daily ip; Vehicle control animals received NaCl twice daily; WT control animals received NaCl twice daily.

Example 16

Measurements of Tyrosine Hydroxylase Levels in the Nigrostriatal Region of Mice Treated with Compound #1

Mice lesioned with MPTP and treated with 20 mg/kg of Compound #1, or NaCl as a negative control, for two months according to EXAMPLE 13 were sacrificed and brains were prepared for immunocytochemistry with an aim toward detecting both (i) the numbers of neurons in the nigrostrial region that stain positively for the presence of TH; and, (ii) the amount of TH per neuron.

The results of these experiments indicated, significantly, that:

(i) the number of neurons staining positively for TH were approximately 20-30% greater, (but not statistically significant due to the small numbers of animals per group, i.e., n=6), in mice treated with Compound #1; and, (ii) the amount of TH per neuron was qualitatively much higher in the Compound #1 treated animals.

Normal, non-MPTP-lesioned mice treated for two months according to EXAMPLE#13 with Compound #1 at 20 mg/kg (daily/ip) showed normal locomotor activity and brain histology without any evidence of overt or histologic toxicity. MPTP-lesioned mice treated for two months with Compound #1 at 20 mg/kg (daily/ip) recovered locomotor activity and histologically showed no evidence of any neural toxicity over-and-above that shown by control MPTP-lesioned NaCl-treated animals.

DISCUSSION: The results obtained in the present EXAMPLE 16, are discussed in EXAMPLE 17, below.

Example 17

Low-Level Delivery of Compounds #1 and #2 Effects Cross-Coupling of Transcriptional Regulation of the Tyrosine Hydroxylase Gene as Mediated Through DAT and GLUT Transporters Citations made in this EXAMPLE 17 appear at the end of this particular examples section. By convention, genes are referred to herein with italices and their protein products in regular text.

DISCUSSION OF EXAMPLES 13-16 follows a definition of terms and an introductory Background section, below.

Definition of Terms Used in Example 17:

Tyrosine hydroxylase (ID is a tetrahydrobiopterin-(BH4; 6-(R)-erythro-5,6,7,8-tetrahydrobiopterin) requiring, iron-containing monooxygenase enzyme which catalyzes the first and rate-limiting step of catecholamine synthesis, i.e. conversion of tyrosine to L-Dopa. TH expression is necessary for neurotransmitter specification of all catecholaminergic neurons. Nigrostriatal synthesis of dopamine accounts for the majority of dopamine in the central nervous system. Indicative of its Importance, TH is regulated by nearly every reported form of regulation including multiple gene-level transcription controls, alternative splicing, mRNA stability, translational control, enzyme stability, feedback inhibition on enzyme activity by end products such as dopamine, allosteric modulation of enzyme activity and phosphorylation-dependent activation of the enzyme by various kinase systems. TH protein, and the TH gene, are stress responsive. Up-regulation of TH/TH activity and expression is triggered during hypoxia and may supply neurotransmitters needed for critical sympathoadrenal stress-responsive functions such as changing breathing and heart rate and liver function.

Dopamine beta-hydroxylase (DBH) catalyzes conversion of dopamine (DA) to noradrenaline (NA) and is selectively expressed in noradrenergic and adrenergic neurons and neuroendocrine cells.

DAT is intended to mean the dopamine (DA) presynaptic monoamine transporter encoded by the DAT gone. DA regulates extracellular levels of DA by reuptake of released DA. DAT is an important site of action of amphetamine and cocaine. Hic-5 is an adaptor protein associated with the intracellular domain of DAT and involved in signal transduction mediated by DAT. Hic-5 contains multiple Lin-11, Isl-1 and Mec-3 (LIM) domains. Hic-3 activation, i.e., phosphorylation, occurs during the course of dopamine binding and transport. Hic-5 is a ligand for Nurr-1. GLUT3-LIM protein is intended to mean a GLUT3 adaptor protein associated with the intracellular domain of GLUT3 and having multiple Lin-11, Isl-1 and/or Mec-3 domains. GLUT3-LIM is activated, i.e., phosphorylated, during the course of Compound #1 binding and transport.

VMAT2 is the vesicular monoamine transporter responsible for vesicle sequestration of dopamine that has been transported into the cell via DAT.

GLUT is intended to mean a family of structurally related, membrane-spanning glycoproteins that mediate the facilitative transport of glucose across plasma membranes. Six GLUT isoforms have been cloned (to date) with GLUT1 widely expressed in endothelial cells of the vasculature including neural vasculature; GLUT3 expressed strongly in the trophoblast and neural cells of the brain and retina; GLUT4 expressed in somatic cells including muscle and adipose tissue; and GLUT2 expressed primarily in the pancreas and liver but also in the intestine and kidney. GLUT2 gene regulation may act in molecular sensor mechanisms determining production of insulin by pancreatic beta-cells and GLUT4 gene regulation may act in hepato-portal molecular sensor mechanisms regulating systemic glucose concentrations.

GLUT1 is intended to mean the endothelial glucose transporter isoform associated with neural endothelial cells. Resident in the cytosol, these transporters are rapidly mobilized to and from the plasma membrane in response to changes in extracellular glucose concentrations. The GLUT1 gene is stress responsive and hypoxia or hypoglycemia induce increased levels of GLUT1 mRNA, increased translocation of and induces increased.

GLUT3 is intended to mean the neural glucose transporter isoform associated with neural cells.

Hypoxia is intended to mean low oxygen tension, e.g., less than 5% $O_2$. Hypoxia increases expression of both the tyrosine hydroxylase (TH) and certan GLUT gene products in neural cells. The response to hypoxia is a cell-type specific, not generalized, and the gene-level response shows differences in regulation for different isoforms of GLUT. i.e., GLUT1 and GLUT3 are activated for increased transcription while GLUT2 is down-regulated.

HIF-1 is intended to mean HIF-1α, HIF-1β and/or HIF-2α, which are hypoxia-inducible transcription factors in somatic, (e.g. myoblasts, cardiac muscle cells, fibroblasts, epithelial cells and the like), and neural cells, (e.g. cells of the central and peripheral nervous system), respectively. HIP-1α is capable of forming functional regulatory heterodimers with aryl hydrocarbon nuclear translocator (ARNT) and is encoded by a gene whose promoter contains a hypoxia response element (HRE). HIF-1 is capable of up-regulating TH, GLUT1 and GLUT3. Activity of HIF-1α protein may also be increased in cells exposed to low oxygen tension.

VHL is intended to mean von Hippel-Lindau protein which interacts with HIF-1α and decreases HIF-1α degradation by inhibiting ubiquination.

Pitx3 is intended to mean the pair-like homeodomain transcription factor 3 also known as pituitary homeobox 3. Pitx3RE is the GGCTT response element for Pitx3.

Pro-OHases is intended to mean prolyl-4-hydroxylases active in hydroxylation of HIF-1 resulting in ubiquitination and subsequent proteasome-dependent degradation.

NFκB is intended to mean the nuclear transcription factor kappa B. NFκB is mobilized from the cytoplasm of cells into the nucleus in response to cytokines, (e.g., IL-1, TNF-α, IFN-γ), hypoxia and certain other cellular stress insults. NFκB increases transcription of stress related genes.

PKC is protein kinase C; PKA is protein kinase A; PI3K is posphoinositol-3 kinase; PP1 is protein phosphatase 1; PP2A is protein phosphatase 2A; and, MEK 1/2 kinase is mitogen enhanced kinase 1 or 2.

CREM is intended to mean cAMP-responsive element modulator; is also known as CREB, an acronym for cAMP response element binding protein; and, CBP, CREB binding protein that is a co-activator of CREB.

AP-1 is intended to mean activator protein-1 transcription factor, AP-1 is intended to mean a genomic AP-1 binding site such as commonly present in a gene promoter region; IRE is intended to mean an insulin response element in a promoter region of a gene; SRE is a serum-response element in a promoter region of a gene; TRE is a TPA (phorbol myristate) sensitive response element in a promoter region of a gene; FSE is a fat specific response element that is present within neural cells at an AP-1 regulatory site that may be responsive to NGF signaling through the Fos/Jun transcription complex; NBRE is the nerve growth factor induced protein I-B binding site response element which is a Nurr1 response element, also referred to herein as NRE; GRE is glucocorticoid response element; and RAR is the retinoic acid response element.

VGCC is intended to mean voltage-gated $Ca^{2+}$ channels involved in membrane depolarization changes and $Ca^{2+}$ influx.

BDNF is brain-derived neurotrophic factor; GCNF is glial cell neurotrophic factor; CRH is corticotropin-releasing hormone; PDGF is platelet-derived growth factor; IL-1 is interleukin-1; TNF-α is tumor necrosis factor-alpha; IFN-γ is interferon-gamma; NGF is nerve growth factor; and, FGF is fibroblast growth factor.

PACAP is intended to mean pituitary adenylate cyclase-activating polypeptide.

ERK is intended to mean the extracellular-regulated kinase involved with c-fos in $Ca^{2+}$ calmodulin dependent responses to hypoxia; PIK3 is the phosphoinositide-3 kinase cascade.

Nurr1 is Nur-related factor 1 a member of the Nur subfamily of orphan nuclear receptors which are ligand activated nuclear receptors, i.e., Nurr1 is also known as aka NOT, TINUR, RNR-1, HZF-3, and NR4A2; Nurr2, also known as Nurr1a, is an alternatively spliced and frame-shifted carboxy-truncated form of Nurr which negatively regulates the binding of several members of the Nur subfamily to NBRE sites; RXR is the retinoid X receptor activator of Nurr1; and, SRC is a steroid receptor coactivator of Nurr1 protein.

Background:

Tyrosine hydroxylase catalyzes the rate-limiting step in biosynthesis of catecholamines including dopamine, norepinephrine and epinephrine. Regulation of the enzyme and gene encoding the enzyme represent the central means for controlling midbrain synthesis of these important central and sympathetic neurotransmitters and adrenomedullary hormones. Accordingly, tyrosine hydroxylase appears to be modulated by nearly every documented form of regulation including e.g. all of the following: namely, (i) gene transcriptional regulation of TH mRNA levels; (ii) alternative mRNA processing/splicing that generates four different enzyme isoforms with differences in activity; (iii) regulation of mRNA stability; (iv) possible translational control; (v) enzyme stability controls; (vi) enzyme co-factor requirements for tetrahydrobiopterin; (vii) enzyme feedback inhibition of the enzyme protein by catecholamine end- and intermediate-products, e.g. dopamine, L-dopa, and NE; (viii) allosteric modulation of enzyme activity; and, (ix) phosphorylation-dependent activation of enzyme activity. At the gene level, transcription controls are exerted as depicted by the inventors in FIG. 9.

Figure 9A:
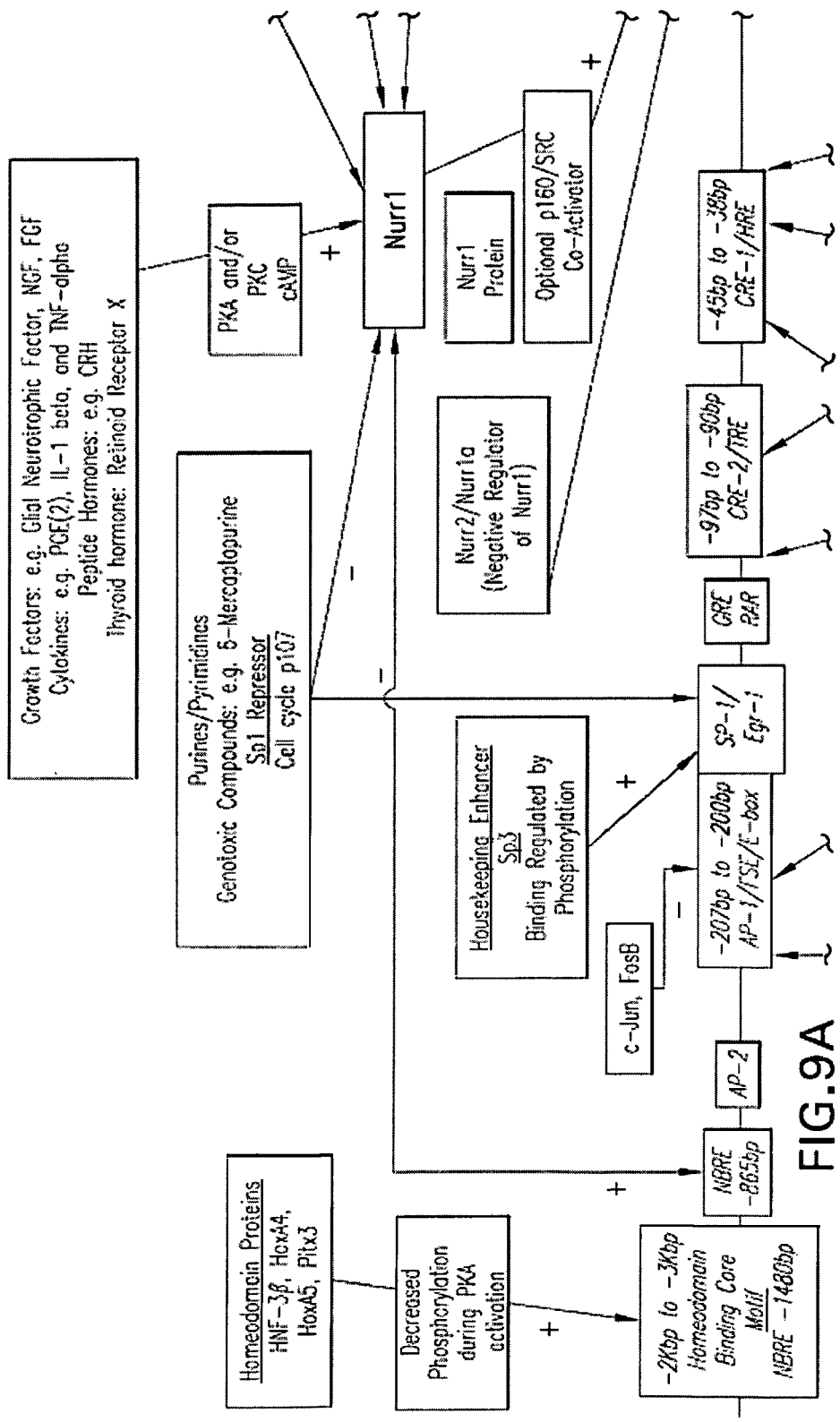
FIG. 9 schematically depicts the disclosed regulatory mechanisms operative at the Tyrosine Hydroxylase gene by cis- and trans-acting elements affecting the promoter region of the gene, i.e., as set forth further in regard to EXAMPLE 17, below.
Figure 9B:
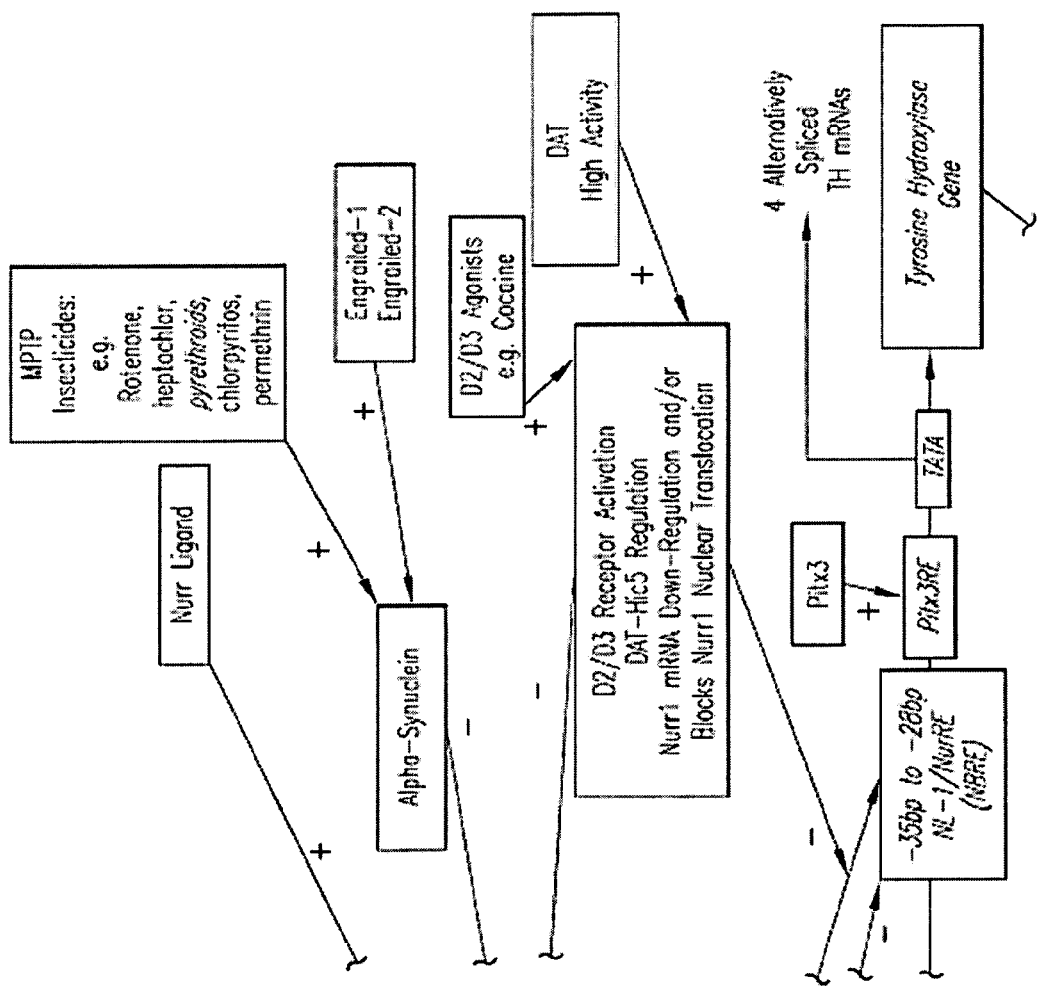
Figure 9C:
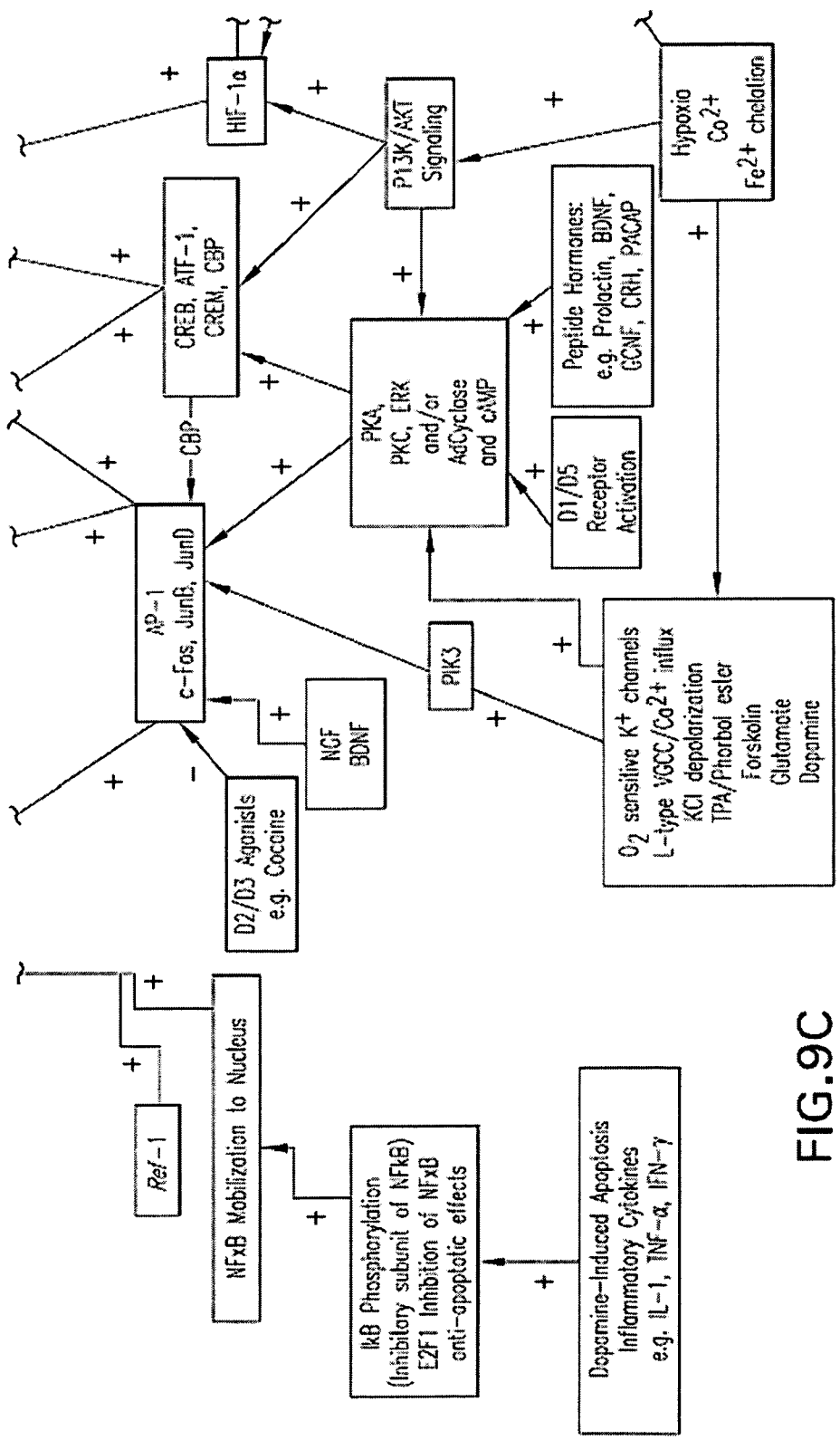

FIG. 9 schematically depicts regulation of the Tyrosine Hydroxylase gene by cis- and trans-acting elements affecting the promoter region of the gene. In FIG. 9-12, positive (+) signs associated with arrows depict that the factor at the beginning of the arrow increases expression or activity of the factor at the arrow head; negative (−) signs depict that the indicated factor decreases expression or activity; and, all indicated activities are as they would occur in wild-type neural cells in the *substantia nigra*. Unless otherwise indicated, all cell-type specific gene regulatory interactions presented in FIG. 9-13 are as they occur in human nigrostriatal neural cells.

The MPTP Model of Parkinsonism:

N-methyl-4-phenyl-1,2,3,6-tetrahydropyridine as oxidized by monoamine oxidases in neural cells to $MPP^+$ is currently believed to be a potent inhibitor of mitochondrial electron transport, increasing oxidative stress, and inducing apoptotic mechanisms responsible for programmed cell death in the nigrostrial region of mice, monkeys and man. MPTP chemical-leisioning results in fewer TH-positive nigral neurons with decreased expression of pre-synaptic DAT and post-synaptic dopaminergic receptors of the D1 and D2 families and increased expression of the alpha synuclein gene (37); and, with the appearance of behavioral abnormalities well correlated with decreased expression of the DAT, VMAT and TH genes (38). MPTP treatment has also been disclosed by certain investigators to increase DA turnover in a manner inhibited by pre-treating mice with 17β-estradiol, progesterone and raloxifene (39). Interestingly, the estradiol pr-treatment reportedly preserve TH and DAT mRNA levels in these MPTP lesioned animals (39).

The 6-Hydroxydopamine Model of Parkinsonism:

The destruction of dopaminergic and serotonergic neural cells by 6-hydroxydopamine (OHDA) is a common tool used in elucidation of function and in investigating pharmaceutical efficacy of Parkinson's and Alzheimer's disease test compounds. Apoptosis is commonly believed to be induced by common oxidative stress mechanisms possibly involving oxidation of toxins into quinones or production of toxic hydrogen peroxide by-products.

The Nurr1 kKnock-Out Mouse Model of Parkinsonism:

Nurr1 (also called NOT. TINUR, RNR-1, HZF-3, and NR4A2) is a member of the nuclear receptor transcription factor superfamily [1], i.e., in the NR4A subfamily with NGFI-B (nerve growth factor-induced gene B) and NOR-1 (neuron-derived orphan receptor-1). Receptors are in this general family are heterodimeric proteins that bind growth factors, steroids and hormones and modify housekeeping gene expression by acting as transcription factors at gene promoter binding sites. The gene for Nurr1 has been mapped to chromosome 2q22-23 and is essential for the developmental induction of nigral dopaminergic neurons, as well as, for the maintenance of mature dopaminergic neuronal function [2,3]. It has been demonstrated that Nurr1 gene activation can enhance TH and DAT expression [4,5]. Dr. W-D. Le and coworkers at Baylor in 1991 generated a Nurr1 knock-out mice model by disrupting the Nurr1 gene in exon 3. Interestingly, these knockout mice demonstrated massive apoptosis of dopaminergic precursor neurons, suggesting that Nurr1 gone function is required for both development and maintenance of dopaminergic neurons. In Nurr1 knock-out mice cellular apoptosis eventually leads to agenesis of nigral DAergic neurons [1]. Features of this Parkinson's animal model include: (i) homozygous Nurr1 knock-out (Nurr1−/−) mice display a selective and complete loss of dopaminergic neurons in the *substantia nigra* (SN); (ii) DA concentrations in the striatum are not detectable; and, (iii) the homozygous mice die within 24 hr of birth. In contrast, heterozygous Nurr1 gene knock-out (Nurr1+/−) mice survive [6] but they are more vulnerable to dopaminergic neurotoxin MPTP compared with the wild-type (Nurr1+/+) mice [7]. In addition, at middle age these heterozygous Nurr1+/− mice develop locomotor impairment, (15 month or older), with features similar to Parkinson's disease. As disease progresses in the heterozygous mice they exhibit a chronic progressive deficiency of nigral dopaminergic function which correlates with progressive impaired motor performance, i.e., with 42% decrease in locomotor activity at 15-16 months and 62% at 22-23 months, (i.e., as evaluated using Rota-Rod measurements). The disease progression in this animal model is also accompanied by both (i) marked progressive reduction in the levels of striatal DA with e.g. a 36% decrease at 15-16 months and 59% at 22-23 months; and, (ii) loss of TH-positive neurons with a 31% decrease at 15-16 months and 54% at 22-23 months.

Nurr1: Developmental Significance:

Recognizing that Nurr1 is a transcription factor appearing critical for the development of midbrain dopaminergic (DA) neurons, Chuang t al. (8) modified mouse embryonic stem (ES) cells to constitutively express Nurr1. The increased Nurr1-expression in the stem cells lead to an up-regulation of all dopaminergic neuronal markers tested, i.e., resulting in a 4- to 5-fold increase in neurons with a dopaminergic phenotype during development.

Alpha-Synuclein: A Coordinate Transcription Regulator of Dopamine Synthesis and Nurr1:

Abnormal accumulation of alpha-synuclein in Lewy bodies is a neuropathological hallmark of both sporadic and familial Parkinson's disease (PD). Although mutations in alpha-synuclein have been identified in autosomal dominant PD, the mechanism by which dopaminergic cell death occurs remains largely unknown, although recent investigations are beginning to shed significant some light on these events. Investigating transcriptional changes in neuroblastoma cell lines transfected with either normal or mutant (A30P or A53T) alpha-synuclein using microarrays, with confirmation of selected genes by quantitative RT-PCR, Baptists and coworkers (9) found significantly altered expression of several genes included members of diverse functional gene groups such as stress response, transcription regulators, apoptosis-inducing molecules, transcription factors and membrane-bound proteins. Among the genes with altered expression these investigators found (i) dihydropteridine reductase, which indirectly regulates the synthesis of dopamine; (ii) GTP cyclohydrolase, sepiapterin reductase (SR), tyrosine hydroxylase (TH) and aromatic acid decarboxylase, i.e., apparently co-ordinately down-regulated by wild-type alpha-synuclein but not mutant alpha-synuclein; and, (iii) Nurr1, the orphan receptor which is a member of the nuclear hormone receptor superfamily NR4A subgroup. In combination, these results suggest that wild type alpha-synuclein coordinately down-regulates DA synthesis and Nurr (9).

Nurr1: A Transcription Regulator of Tyrosine Hydroxylase:

Kim et al. (10) recently disclosed that the product of the Nurr1 gene may transactivate the promoter of the TH gene in a cell type-dependent manner. Nurr1 did not apparently exert regulator effects at the dopamine bet-hydroxylase (DBH) promoter. (i.e., the terminal enzyme in noradrenalin synthesis). Consistant with these results, only the TH promoter contains multiple sequence motifs homologous to the known Nurr1-binding motif; NBRE. Deletion analysis in the tyrosine hydroxylase promoter indicated the presence of three NBRE motifs <1.0 kb upstream from the origin of gene transcription, i.e. NL1, NL2 and NL3. Among these potential motifs, site-directed mutational analysis showed that NL1, residing from −35 to −28 bp, which is reportedly most critical for mediating the transactivation by Nurr1. However, DNase I footprinting and electrophoretic mobility shift assays showed that NL3, but not NL1 or NL2, has high binding affinity to Nurr1 (10). Kessler et al. (11) in studies of the TH promoter region apparently identified an additional regulatory motif in the upstream TH promoter region at −2 kb to −9 kb relative to the transcription start site and within these regions were also potential recognition sites for NR4A2 (Nurr1), HNF-3beta, HOXA4, and HOXA5. These results suggest that Nurr1 may play a direct developmental and maintenance role in specifying the identity of dopaminergic cells by activating tyrosine hydroxylase gene transcription in a cell context-dependent manner.

Chu et al. (12) disclosed that virtually all of tyrosine hydroxylase-immunoreactive (TH-ir) neurons within the young adult human *substantia nigra* were Nurr1-immunoreactive (Nurr1-ir) positive. Stereologic counts reportedly revealed a significant reduction in the number of Nurr1-ir nigral neurons in middle-aged (23.13%) and aged (46.33%) individuals relative to young subjects. The loss of Nurr1-ir neurons was associated with a similar decline in TH-ir neuron number. In this regard, TH-ir neuronal number was reportedly decreased in middle-aged (11.10%) and in aged (45.97%)

subjects, and this loss of TH-ir neurons was highly correlated (r=0.92) with the loss of Nurr1-ir neurons.

Nurr1: Regulation by Purine Nucleosides Released in Stress Responses:

As set forth above, Nurr1 is an orphan member of the nuclear hormone receptor superfamily NR4A subgroup along with its close relative NOR-1. This subgroup is categorized as immediate early response genes that are induced through multiple signal transduction pathways. They have been implicated in cell proliferation, differentiation, T-cell apoptosis, chondrosarcomas, neurological disorders, inflammation and atherogenesis. However, the mechanism of transcriptional activation, coactivator recruitment, and agonist mediated activation remains largely obscure. Recent studies of NOR-1 indicate that a variety of 6-MP analogs all efficiently activated NOR-1. These findings lead the inventors to believe that signaling pathways already known to modulate cell proliferation through inhibition of de novo purine and/or nucleic acid biosynthesis may also be involved in regulating the activity of transcription factors in the NR4A family and Nurr1.

Abayratna Wansa and coworkers (13) suggested that transcription factors of the NR4A subgroup may be regulated by and mediates the genotoxic stress response, i.e., this subgroup of transcription factors are suggested to function as sensors to identify modified purines which could result in genotoxicity.

Ordentlich et al. (14) investigated Nurr1 instead of NOR-1 and found, in similar manner, that Nurr1 appears to be subject to regulation by purine nucleosides and may be activated by 6-mercaptopurine (14). From these combined findings it now appears possible to the inventors that altered nucleosides and/or purine nucleosides released in stroke and other genotoxic stress responses may down-regulate expression of Nurr1 resulting in-turn in decreased dopamine synthesis.

Nurr1: Possible Relation by Kinase Pathways:

Studying expression of Nurr1, NGFI-B and NOR-1, Satoh et al. (15) report that all are expressed constitutively in various human neural and non-neural cell lines under the serum-containing culture condition and their levels are up-regulated in human neurons by activation of protein kinase A or protein kinase C pathway.

The NGFI-B (Nur77) subfamily of orphan nuclear receptors (NRs), which also includes Nurr1 and NOR1, bind the NurRE regulatory element as either bomo- or heterodimers formed between subfamily members. These nuclear receptors reportedly mediate the activation of pituitary proopiomelanocortin (POMC) gene transcription by the hypothalamic hormone corticotropin-releasing hormone (CRH), a link between neuronal and endocrine components of the hypothalamo-pituitary-adrenal axis. CRH effects on POMC transcription do not require de novo protein synthesis, suggesting that the signaling mechanisms may be pre-existent in cells. Elucidating these mechanisms, Maira et al. (16) recently reported that CRH activates Nur factors via the cyclic AMP/ protein kinase A (PKA) pathway. CRH induction of PKA apparently rapidly increases nuclear DNA binding activity of NGFI-B dimers but not monomers. PKA-activated Nur dimeric factors have enhanced binding to target response elements in the POMC gene promoter. Providing additional mechanistic understanding, Maim et al. (16) reported that p160/SRC coactivators were recruited to the Nur dimers (but not to monomers) and that coactivator recruitment to NurRE was enhanced in response to CRH. Thus, in this system PKA activation apparently activates coactivator-induced potentiation of transcription factor dimmer binding at gene regulatory sites. Taken together, these results suggest to the inventors that Nurr1 dimeric transcription factors may be activation targets in PKA signaling pathway triggered by peptide hormones.

Multiple Requirements and Other Dopaminergic Diseases:

In reviewing evidence from recent transgenic knock-out animal model studies, Ells (17) reminds (i) that alterations in dopaminergic neurotransmission have been implicated in a number of human neuropathologies including Parkinson's disease, schizophrenia and attention deficit/hyperactivity disorder; and, (ii) that there are multiple requirements for development, transmission and maintenance of DA neurons: namely, for development the genes engrailed-1 and -2, lmx1b and Nurr1; for neurotransmission tyrosine hydroxylase (TH), vesicular monoamine transporter, dopamine transporter (DAT) and the D2 and D3 receptors; and, for neuronal survival alpha-synuclein, glial neurotrophic factor and superoxide dismutase.

Dysregulation in dopaminergic neurotransmission might play a role in the pathogenesis of schizophrenia, and therefore genetic components of the dopamine (DA) pathway could conceivably confer a genetic risk. Since NR4A2/Nurr1 is essential for the development and maintenance of mesencephalic DA-synthesizing neurons and the Nurr1 gene product forms heterodimer with the retinoid X receptor (RRX), it is possible that disturbances in retinoid-signaling could be involved in susceptibility to schizophrenia. However, Iwayama-Shigeno et al. (18) report that data do not support the notion that haplotype analysis of schizophrenic polymorphisms in Japanese do not support a role for the NR4A2/ Nurr1 gene plays a major role in determining statistical risk.

Modulation of the NURR subfamily of nuclear receptors may also be an important mechanism regulating pathways associated with inflammatory joint disease. In studies conducted by McEnvoy et al. (19) the signaling mechanisms for induction of inflammatory mediators in rheumatoid arthritis synovial tissue was reported to involve the possible regulation by the NURR subfamily. Markedly enhanced expression of NURR1 is observed in synovial tissue of patients with RA compared with normal subjects and in primary RA and normal synoviocytes and Nurr1 (but not NOR-1 or NUR77) mRNA and protein were increased in response to PGE(2), IL-1beta, and TNF-alpha.

Nurr1: Summary:

Recent findings suggest to the inventors that dysregulation at the level of Nurr1 has the potential to decrease tyrosine hydroxylase mRNA levels, decreasing levels of dopamine synthesis in the *substantia nigra*—i.e., a Parkinson's hallmark phenotype. Dysregulation in Nurr1 could potentially result from any combination of the following: namely, (i) increased steady-state down-regulation of Nurr1 mediated by alpha synuclein, age-related decreases in Nurr1 or decreased levels of Nurr1 activators (e.g., intracellular levels of purines and pyrimidines and the like); (ii) altered Nurr1 protein activity resulting in lowered responsiveness to PAK activity and/or age-related decrease in the activity of one or more Nurr1 co-activator/enhancer (telomeric) proteins like p160/SRC co-activators (iii) defects or alterations in Nurr1 dimer formation with NR4A family member proteins; (iv) mutant altered Nurr1 or Nurr1 co-activator or dimer partner protein; or, (v) genetically altered promoter binding sites in target genes or in the Nurr1 promoter region.

In studies of Nurr1 allelic variation in Parkinson's patients, Le and coworkers (20) have reportedly identified a homozygous polymorphism in Intron 6 of the human Nurr1 gene that seems associated at a higher frequency with familial Parkinson's than with spontaneous Parkinson's.

At least one recent study suggests an additional possibility: namely, that chronic long-term stimulation at the D2 receptor, i.e., in cocaine users, may lead to decreased Nurr1 expression in human brain (21). In other receptor-driven expression systems, it is appreciated that compensatory down-regulation of transcription can occur in response to chronic long-term receptor activation. Thus, it is also possible that chronic production of inflammatory mediators by microglial cells (macrophages) in the brain may down-regulate Nurr1 activity.

Reservoir Delivery:

Gene transfer studies conducted by others have reported negative feedback regulation from simultaneous expression of the genes for TH; GTP-cyclohydrolase-I, (rate limiting in tetrahydrobiopterin -BH1- co-factor synthesis); and, aromatic L-amino decarboxylase (capable of converting the TH L-Dopa product into dopamine), i.e., the reconstructed cells produced dopamine and the synthesis was then apparently down-regulated by the dopamine end-product (29). Negative feedback regulation was reportedly overcome in these gene therapy studies (29) by also supplying a vesicular monoamine transporter with the aim of sequestering the synthesized L-dopa and dopamine within vesicles. Such findings reinforce the inventors belief in the great importance of Compound #1 binding and transport by DAT and GLUT transporters, as well as, the importance of this uptake route in establishing sequestration into vesicles, as discussed further below.

Coordinated DAT/GLUT3 Signaling:

DAT and GLUT are transporters, to the inventor's knowledge these plasma membrane proteins have not previously been implicated in signal transduction or gene-level regulatory controls.

Discussion:

In Vitro and In Vivo Studies:

The results presented in EXAMPLES 13-16, supra, show that Compound #1 alleviated locomotor symptoms in three different animal models commonly used to evaluate a Parkinson's drug candidate: namely, the MPTP-lesioned mouse model (EXAMPLE 13); 6-hydroxydopamine lesioned rats (EXAMPLE 14); and, the Nurr1 genetic knockout mouse model (EXAMPLE 15).

Potential Mechanisms of Action:

Attempting to explain therapeutic mode of action, binding of Compound #1 to neural cells in the striatum may occur according to one or more of the following mechanisms: namely, (i) binding as an agonist at D1/D5 receptors post-synaptically to supply needed dopamine for post-synaptic innervation; (ii) binding as an agonist at D1/D5 receptors located on pre-synaptic plasma membrane; (iii) binding as an agonist, at a low level, at a D2/D3 receptor; (iv) transport via a pre-synaptic DAT transporters; and, (iv) transport via a pre- or post-synaptic neural GLUT3 transporter.

The results of in vitro experiments presented in EXAMPLES 11 and 12 show that (a) Compound #1 has predominantly D1/D5 binding specificity and that receptor binding triggers signal transduction with changes in intracellular cAMP; (b) Compound #1 is transportable at DAT; and, (c) Compound #1 is transportable at GLUT1, i.e., as evidenced by the locomotor effects disclosed in EXAMPLES 13-16 confirming transport via GLUT1 at endothelial cells of the blood brain barrier. Possible binding at a D2/D3 receptor site in vivo, thus, seems less likely than binding to a D1/D5 receptor.

D1/D5 Agonist Activity:

Binding at D1/D5 pre- or post-synaptic receptors with associated triggering of a kinase-mediated signal transduction cascade (e.g. through PKA, PKC or calmodulin kinase II with cAMP, $Ca^{2+}$ flux and possible CREB involvement) may up-regulate TH gene expression, e.g. through CRE or AP-1 response elements as depicted in FIG. 9. However, the results presented in EXAMPLE 16 also show increased TH protein in the nigrostriatal neurons of MPTP-lesioned animals treated with Compound #1. This singular finding indicates that at least some of the important effects of Compound #1 must be exerted pre-synaptically, i.e., increasing TH levels and up-regulating the TH gene—but how? The common perception is that end-products like dopamine feedback on gene function in a negative manner: so, either this is a misconception with respect to Compound #1, or there must be some other explanation for the findings of increased TH protein in Compound #1-treated animals. Theoretically, increased immunoresponsive TH protein levels in treated animals could result from either: (a) increased protein stability, i.e., decreased turnover; (b) increased mRNA stability, i.e., decreased turnover, with increased TH protein synthesis; or, (c) from increased mRNA transcription and translation. At present it is believed most likely that the majority of the increased TH protein results from increased TH mRNA transcription and translation. It is believed less likely that stability of mRNA and protein accounts for the observed changes in the striatum of animals treated with Compound #1. Assuming in argumentum that this is the case, then even if Compound #1 is binding and activating D1/D5 it is likely that up-regulation of TH relates to some other property of the instant class of compounds.

Coordinated Therapeutic Mode of Action:

Potential in vim binding sites for Compound #1, i.e., in addition to D1/D5 receptor sites, may be reasoned as follows: namely, (i) Dopamine re-uptake transporters, i.e., DAT, mediate pre-synaptic re-uptake of dopamine from the synaptic cleft and VMAT2 transporters sequester the reuptake-dopamine preventing possible toxicity associated with dopamine oxidation products. It seems likely to the inventors that DAT reuptake processes are monitored at a gene level and that response elements must exist in the TH regulatory region to account for DAT activity. Similarly, DAT associated co-factors such as Hic-5, LIM or other adaptor proteins must serve functions in signal transduction to the TH gene. Thus, is currently believed highly likely that Compound #1 binding and translocation at DAT trigger changes effective to up-regulate the TH gene. Signaling through DAT and regulatory affects of DAT transport on TH gene expression have, to the inventor's best knowledge, not been previously disclosed;

(ii) It is also believed highly likely that GLUT3 facilitative transporters on nigral neural cells mediate uptake of Compound #1. It is believed highly likely that glucose response elements exist in the TH gene regulatory region and that GLUT3 transport is monitored at a gene level. Again, to the inventor's best knowledge, signaling through GLUT and regulatory effects on TH gene expression have not previously been disclosed; and, (iii) it is believed highly likely that monitoring glucose transport through GLUT3 and dopamine reuptake through DAT constitutes a novel important sensor system operative within striatal neural cells for controlling bodily metabolic responses to stress and trauma. Again, to the inventor's best knowledge a coordinated DAT/GLUT3 sensor system operative in nigral cells at the level of TN gene regulation has not been previously disclosed.

Advantageous Properties of the Instant Therapeutic Compounds:

Transport of Compound #1 by DAT and GLUT transporters insures that uptake and sequestration into VMAT2 and GLUT3 cytoplasmic vesicles, thereby alleviating potential dopamine intracellular toxicity of the degradation and oxidation products of Compound #1, as well as, possible negative feedback inhibitory activity of dopamine at both the enzyme and gene transcription levels. Vesicular storage also allows time for processing of pro-drug Compound #1 into glucose and dopamine, and assures that the processed dopamine is readily available for synaptic release. Vesicular storage in striatal neural cells in the midbrain, acting in combination with gradual release of Compound #1 from GLUT1 receptors on red blood cells and regulated transport of Compound #1 via endothelial cells at the blood brain barrier, are all presently believed to be key in achieving the therapeutic efficacy of the instant class of therapeutic agents, i.e., via gradual sustained release at low levels.

Figure 12A:
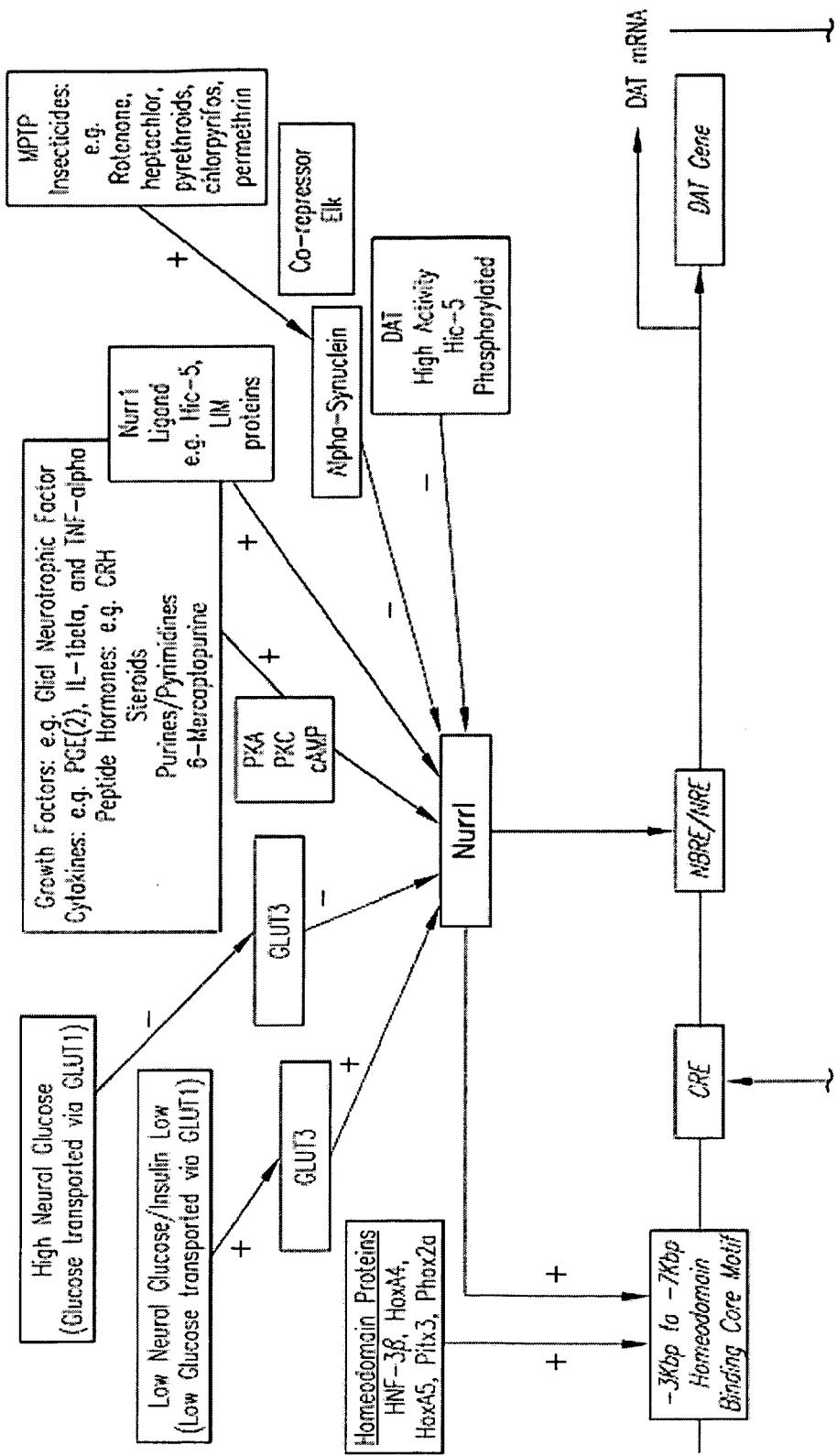
Figure 12B:
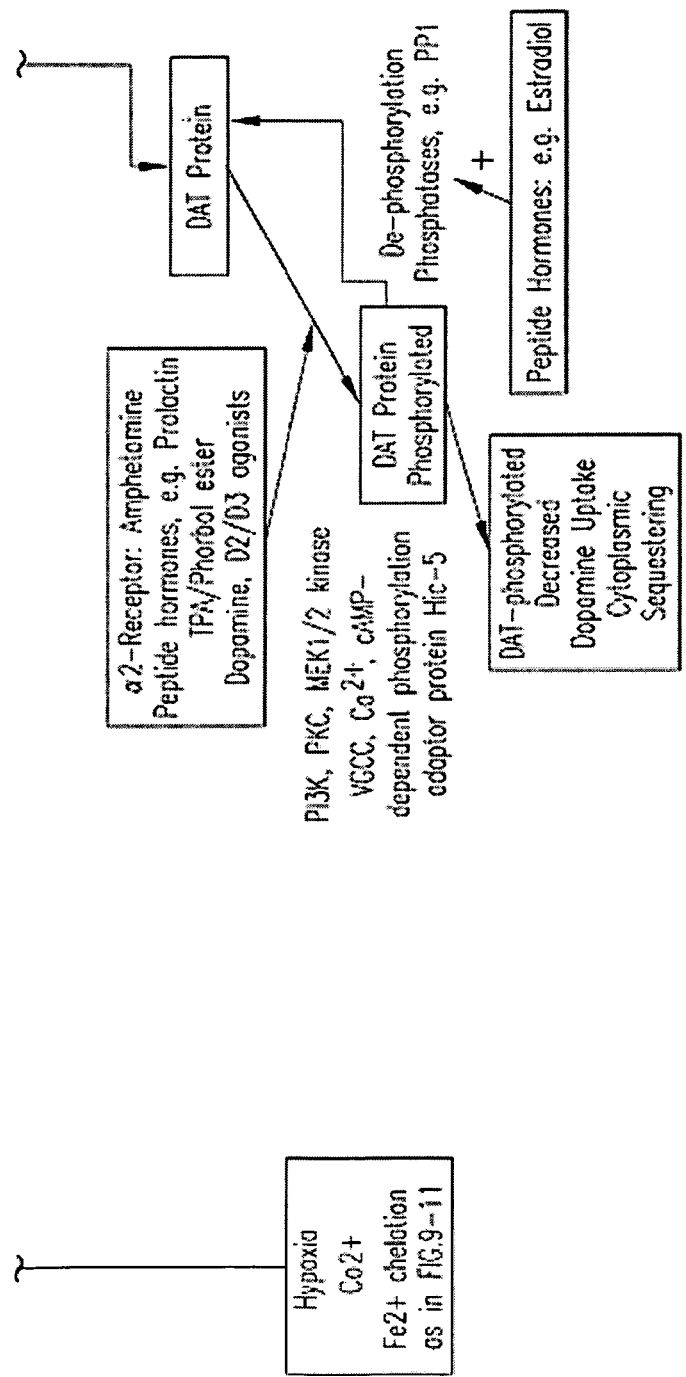
Figure 13A:
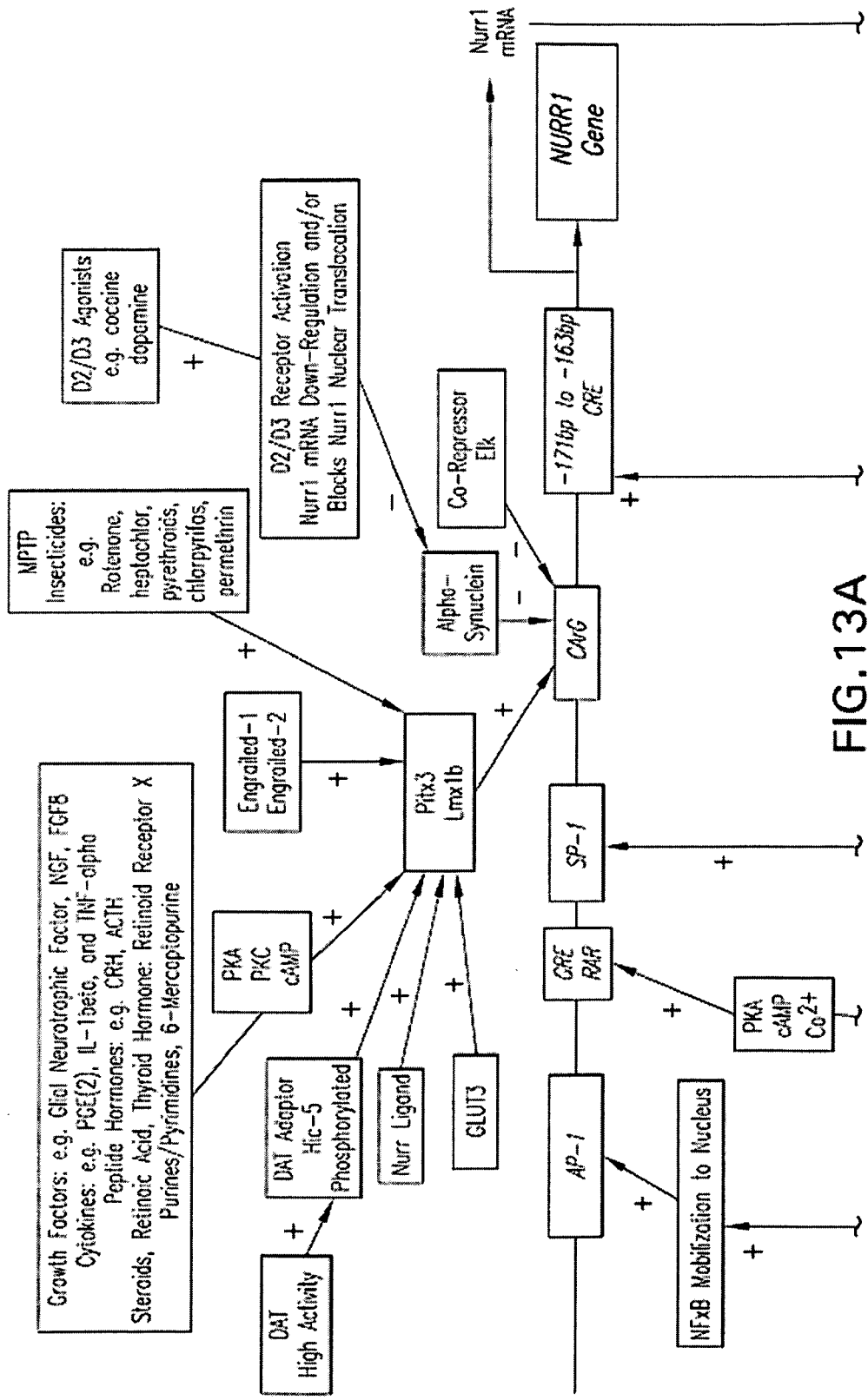
FIG. 13 schematically depicts the disclosed regulatory mechanisms operative at the Nurr gene by cis- and trans-acting elements affecting the promoter region of the gene, i.e., as set forth further in regard to EXAMPLE 17, below.
Figure 13B:
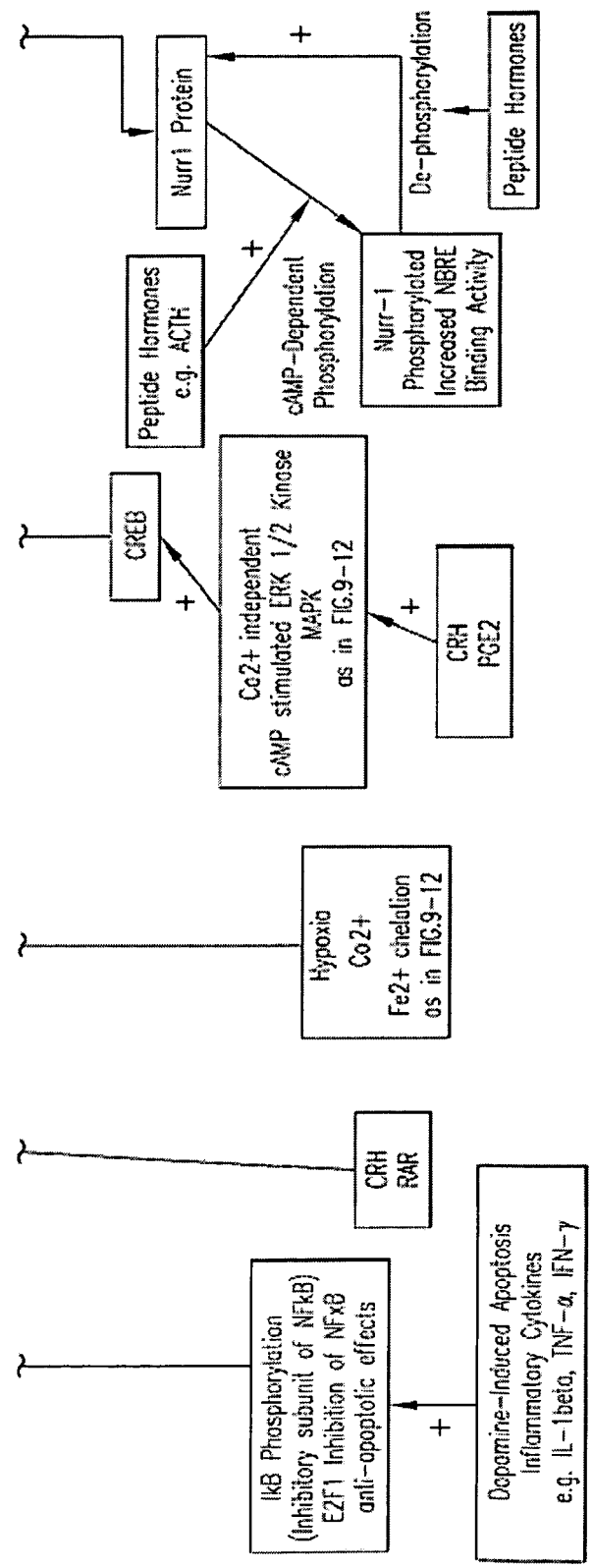
Figure 14B:
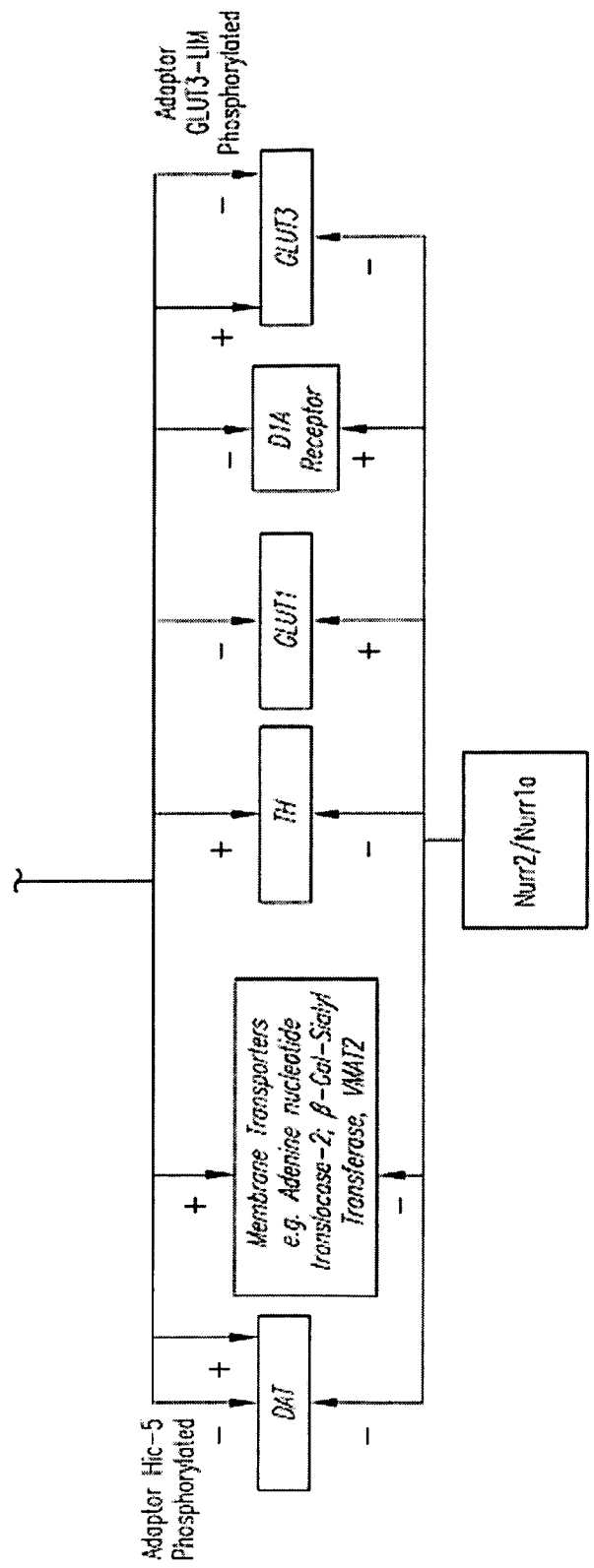
FIG. 14 schematically depicts coordinate regulatory mechanisms exerted by SP1, SP2, Nurr1 and Nurr2 at the gene regulatory regions of the DAT, VMAT2 (the dopamine vesicular storage transporter), TH, GLUT1, GLUT3, D1A (Dopaminergic receptor-1A) and membrane transporters Adenine nucleotide translocate-2 and beta-galactosidase-sialyltransferase, i.e., as set forth further in regard to EXAMPLE 17, below.

A Novel Drug Target:

In summary, the finding that TH immunoreactive protein is increased in striatal neurons in Compound #1-treated MPTP-lesioned mice (EXAMPLE 16) is considered to be highly significant as it indicates to the inventors a previously unrecognized linkage between TH gene expression and compounds, like Compound #1, that are capable of simultaneously accessing GLUT3 and DAT. Further, the findings indicate highly likely gene regulatory controls exerted on TH transcription and/or enzyme protein which are responsive to GLUT3 and DAT transporter activity. The following additional reasoning may be posited: namely, 1) Why should there be coupling of signaling at GLUT3, DAT and TH? Important clues about possible coordinate coupling of regulation at GLUT3, DAT and TH is evident in detailed analysis of TH gene regulation: e.g., responsiveness of TH gene promoter elements to adrenocorticoid hormones, insulin, glucose levels and hypoxia. Teliologically, the presence of "fight-or-flight" glucocorticoid regulatory elements (GRE) in the TH promoter region along with glucose sensor capability suggests that in the process of responding to a "flight" directive from adrenal gland hormones the brain may judge it to be wise to check available bodily reserves of both dopamine and glucose, and if necessary, increase brain glucose transport, expression of TH and output of parasympathetic and sympathetic mediators;

2) Assuming in argumentum that the midbrain nigrostrital region contains a coordinated sensor for glucose and dopamine, then what is it and how does it work? Again, the key rate limiting enzyme in catecholamine synthesis is tyrosine hydroxylase. The importance of this enzyme is affirmed by the findings that virtually every form of known regulation is exerted upon the TH gene. mRNA and protein (as summarized in the Background section above). Even breathing and heart rate are regulated by the catecholamine neurotransmitters whose synthesis is catalyzed by TH. Thus, the promoter regulatory region of the TH gene and its associated transcription factors is believed by the inventors to be the key sensor system for balancing dopamine synthesis in response to glucose transport (mediated through GLUT3) and dopamine reuptake through DAT. The following details, below, are offered up in answer to the question "how does it work?";

3) FIGS. 9-14 disclose the inventors understanding of signaling events relating to regulation of the TH (FIG. 9), GLUT1 (FIG. 10), GLUT3 (FIG. 11), DAT (FIG. 12) and Nurr1 genes (FIG. 13), as well as how coordinate regulation is achieved through the counter-balancing effects of SP1/SP3 and Nurr1/Nurr2 (FIG. 14).

FIG. 9 schematically depicts regulation of the Tyrosine Hydroxylase gene by cis- and trans-acting elements affecting the promoter region of the gene. In FIG. 9-12, positive (+) signs associated with arrows depict that the factor at the beginning of the arrow increases expression or activity of the factor at the arrow head; negative (−) signs depict that the indicated factor decreases expression or activity; and, all indicated activities are as they would occur in wild-type neural cells in the *substantia nigra.*

Figure 10A:
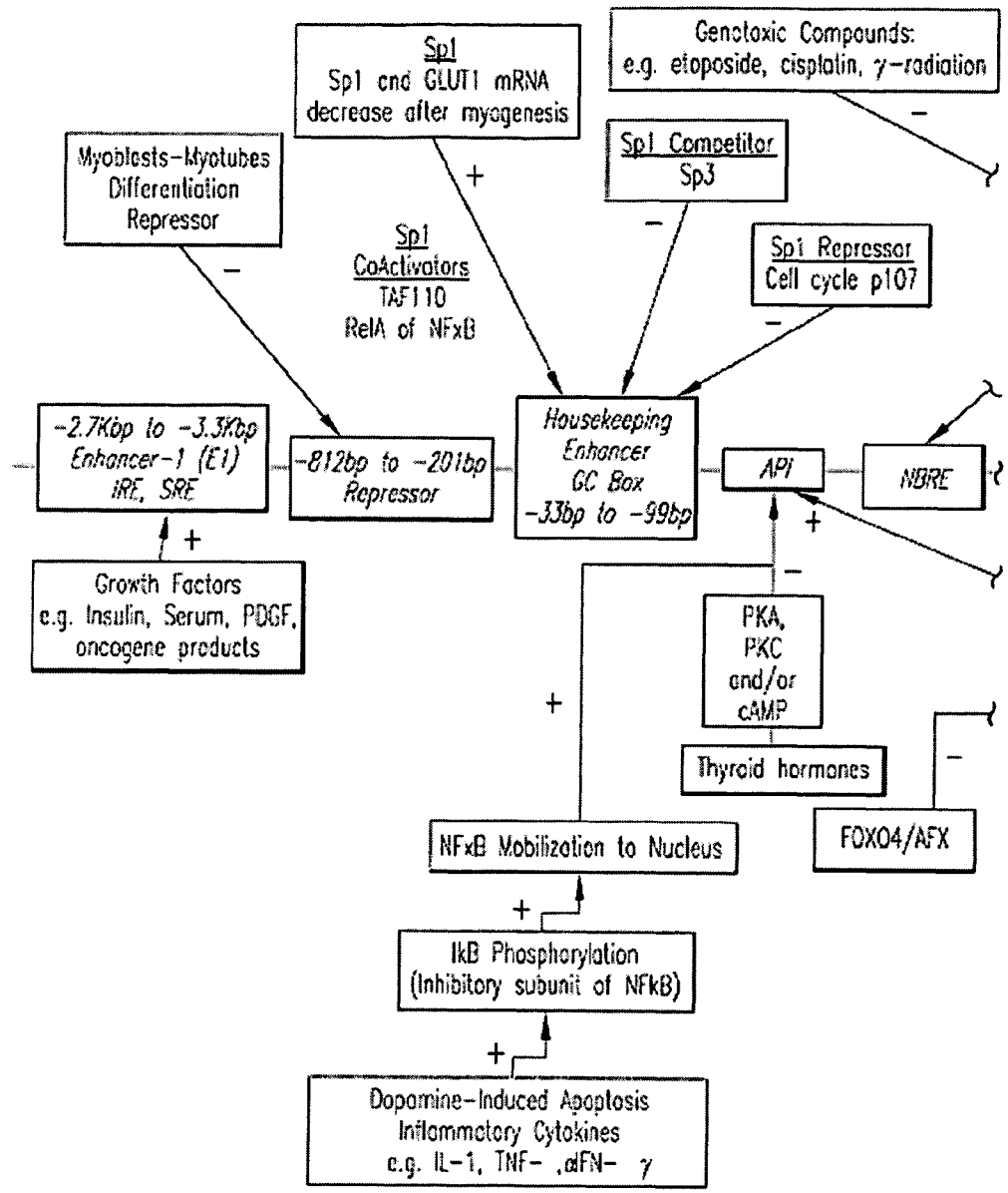
Figure 10B:
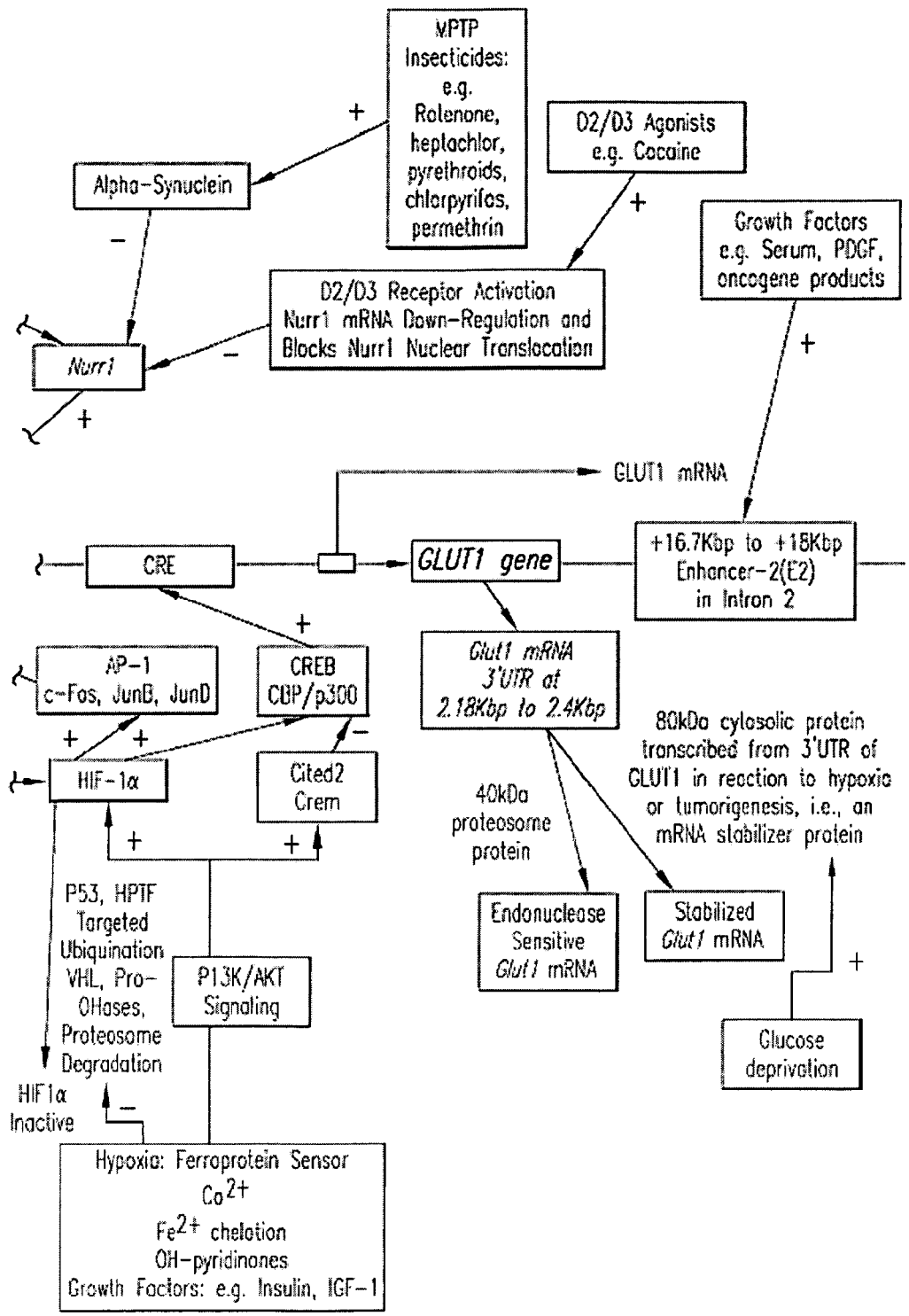

FIG. 10 schematically depicts the disclosed regulatory mechanisms operative at the GLUT (vascular endothelial glucose transporter) gene by cis- and trans-acting elements affecting the promoter region of the gene.

Figure 11A:
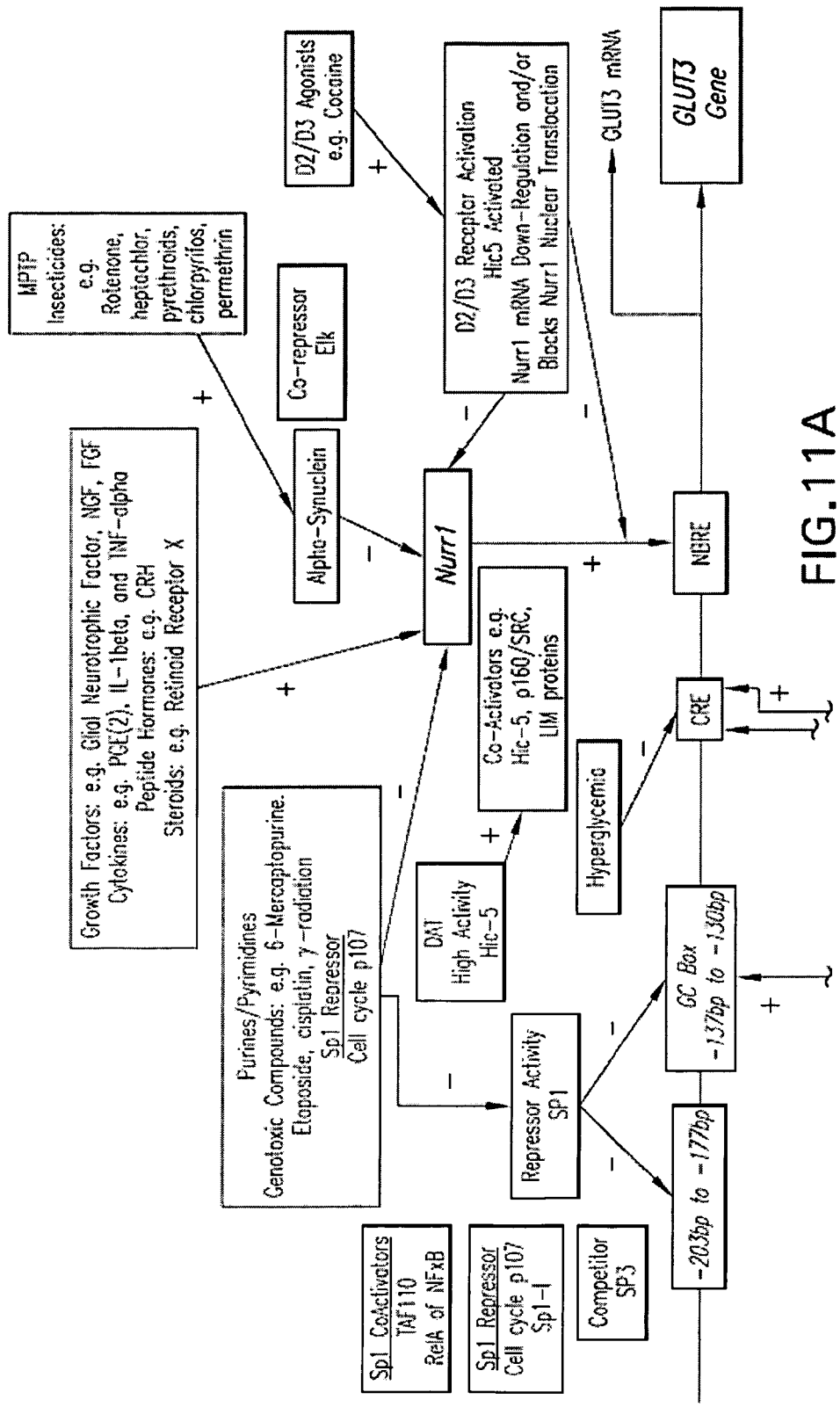
Figure 11B:
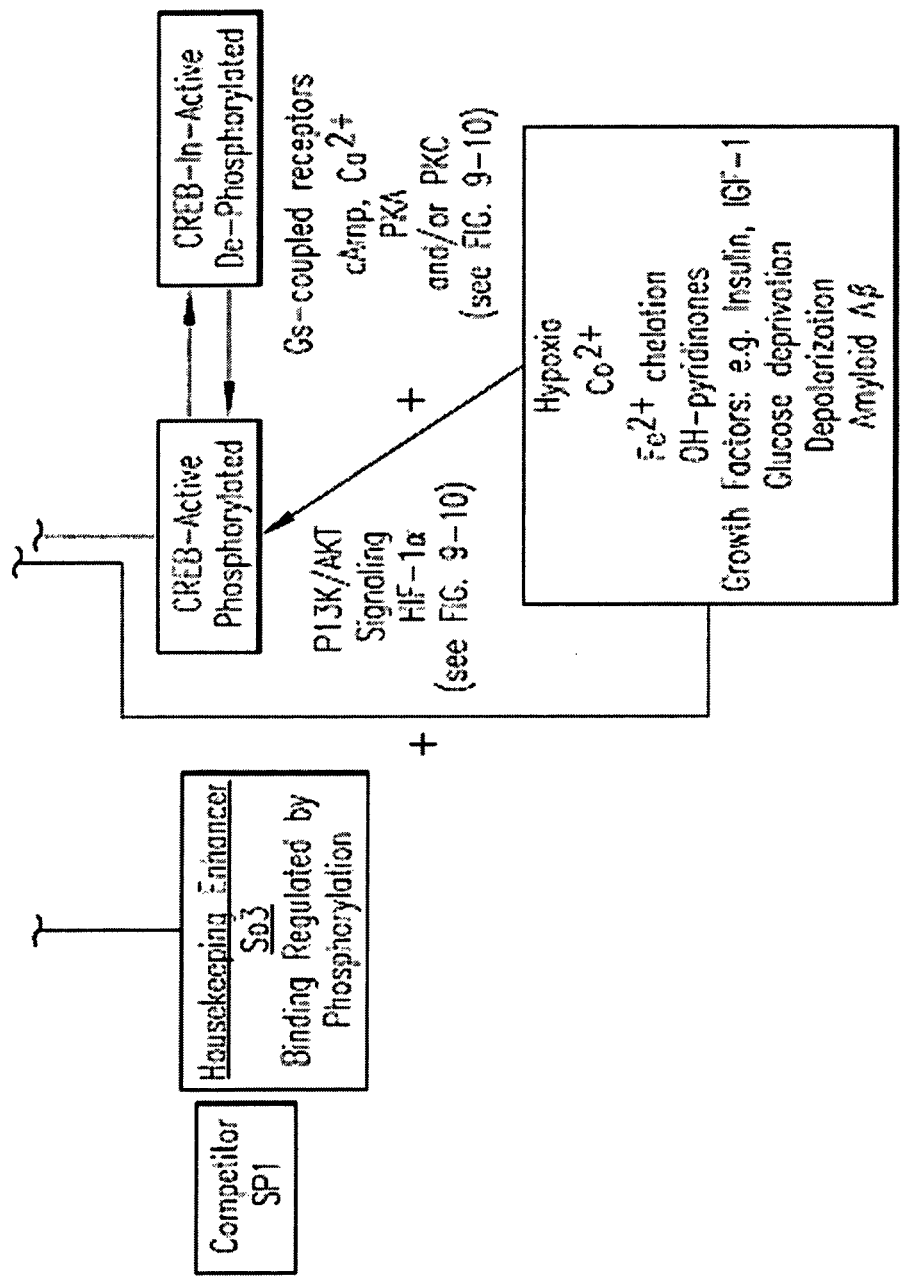

FIG. 11 schematically depicts the disclosed regulatory mechanisms operative at the GLUT3 (neural glucose transporter) gene by cis- and trans-acting elements affecting the promoter region of the gene.

FIG. 12 schematically depicts the disclosed regulatory mechanisms operative at the DAT (dopamine re-uptake neural transporter) gene by cis- and trans-acting elements affecting the promoter region of the gene.

FIG. 13 schematically depicts the disclosed regulatory mechanisms operative at the Nurr gene by cis- and trans-acting elements affecting the promoter region of the gene.

FIG. 14 schematically depicts coordinate regulatory mechanisms exerted by SP1, SP2, Nurr1 and Nurr2 at the gene regulatory regions of the DAT, VMAT2 (the dopamine vesicular storage transporter), TH, GLUT1, GLUT3. D1A (Dopaminergic receptor-1A) and membrane transporters Adenine nucleotide translocate-2 and beta-galactosidase-sialyltransferase.

4) To the inventors thinking, a coordinated rapid system for responding to stress, trauma, hypoxia and inflammation requires a single effector operative in simultaneously up-regulating the critical dopaminergic gene functions, i.e., the transcription factor Nurr1. A critical system for responding to stress also requires counteracting balances, i.e., Nurr2, as well as a multiplicity of backup components, i.e., the regulatory mechanisms set forth in FIG. 9-13. However, such a rapid-response system is undoubtedly not suitable for day-to-day balancing and tuning of nigral dopamine products. Thus, as set forth schematically in FIG. 14, it is believed most likely that reciprocal SP1/SP3-mediated balancing controls exerted on DAT, GLUT 3, T, and other dopaminergic components (FIG. 14) provides basal level balanced +/− regulatory controls to fine-tune ongoing cellular functions, i.e., housekeeping functions. The multiplicity of backup components for maintaining control of critical catecholamine synthesis are depicted in FIG. 9-13.

Defects in Existing L-Dopa, Carbidopa and Synemet Treatments:

Existing treatments of Parkinson's disease suffer fundamental mechanistic flaws in view of the instant disclosed regulatory interactions, as also supported by certain recent disclosures from others. For example, Guttman et al. (30) disclosed results of PET studies in patients with early Parkinson's disease (PD), wherein binding activity of test compounds at dopamine transporters (DAT) was reportedly reduced after therapeutic administration of L-dopa. Similarly, Torstenson et al. (31) disclosed results of L-DOPA influx rates after levodopa infusion as recorded in PET studies in patients with mild PD or advanced PD. Influx rates were decreased in patients with mild PD and Increased in patients with advanced PD, suggesting to these authors a positive upregulation in patients with advanced disease. In wild-type rats, L-Dopa:carbidopa (50:5 mg/kg) administered three times daily significantly decreased DAT levels (32). Looking at DAT transporters expressed *Xenopus oocytes* and rat striatum, Gulley et al. (33) disclosed down-regulation of DAT function after repeated brief exposure to dopamine, AMPH or tyramine. Down-regulation of DAT is very counter-productive to successful long-term therapy and may also account for the significant fluctuations seen in patient responsiveness, with time, to therapy.

Defects in Existing D2 Agonist Treatments:

As depicted schematically in FIG. 9, D2 receptor agonists, but not D1 agonists, have been disclosed by others to down-regulate transcription of the tyrosine hydroxylase gene in vitro, in tissue slices (e.g. 34), in fetal grafts in animals (e.g. 35) and in patients. Down-regulation may occur as a result of D2-agonist induced decreased CRE activity (36), i.e., deleterious to transcription of the TH gene (FIG. 9). Down-regulating synthesis of tyrosine hydroxylase is very counterproductive to successful long-term therapy and may also account for the significant fluctuations seen in patient responsiveness, with time, to therapy. D1 agonists act in vitro to increase, rather than decrease, CRE activity (36) i.e., A change advantageous to increased TH gene transcription (FIG. 9).

At the Gene Level:

As set forth in regard to the FIGURES above, the instant invention discloses that agonists binding at presynaptic D2/D3 receptors down-regulate Nurr1 gene expression (FIG. 13) with resultant decreased positive-transcription regulation at the DAT gene promoter (FIG. 12) and also at the TH gene (FIG. 9). As a result, despite supplying substrate L-dopa for dopamine synthesis these D2/D3 agonists actions amply any nigrostriatal deficiencies in TH and DAT, i.e., a counter-productive in a long term therapy designed to correct a defect in transcription regulation of a TH gene.

At the Protein Level: As schematically depicted in FIG. 12, dopaminergic agonists at D2/D3 receptors may activate phosphorylation of DAT through the actions of PIK3, PKC and/or MEK 1/2. Phosphorylation of DAT down-regulates dopamine re-uptake by (a) sequestering phosphorylated DAT in cytoplasmic vesicles, thereby reducing plasma membrane DAT available for re-uptake of dopamine; and, (b) reducing the Vmax of dopamine transport by DAT. Both of these actions are counter-productive in a long term therapy designed to correct a nigrostriatal dopamine deficiency.

Additional Therapeutic Methods of Use:

The ventral tegmental area (VTA) and *substantia nigra* pars compacta (SNC) regions of the striatum includes cells whose synapses impinge in brain areas implicated in locomotion; conditioning, learning and motivation of appetite and feeding behavior; alcohol withdrawal seizures; and, reward. The disclosed association of DAT, GLUT3 and TH (above) indicates additional uses for the compounds of the instant invention in treatments of feeding disorders, e.g., binging eating leading to obesity and increasing risk of Type 2 diabetes, bulimia nervosa, anorexia and the like. Other uses of the compounds of the instant invention include the following: namely, (i) reversing DAT blockade by psychostimulants such as cocaine, e.g. in an acute care setting; (ii) treatments for alcohol withdrawal symptoms including seizures; (iii) treatments for insecticide poisoning related to dysfunctional regulation of TH and DAT; (iv) treatments for sleep apnea and/or narcolepsy as related to dysfunctional regulation of TH aid DAT; (v) treatments for schizophrenia, attention deficit disorder and hyperactivity syndromes; (vi) treatments for panic disorders; ad, (vii) treatments of die rheumatoid synovium, lung and immune systems, wherein the aim of each of the foregoing treatments is to restore a more normal transcription regulation of DAT and TH to a patient in need thereof.

CITATIONS MADE IN EXAMPLE 17

1. Saucedo-Cardenas O, Quintana-Hau J D, Le W D), et al. Nurr1 is essential for the induction of the dopaminergic phenotype and the survival of ventral mesencephalic late dopaminergic precursor neurons. PANS USA. 1998, 95:4013-4018
2. Zetterstrom R. H., Solomin L., Jansson L., et al. Dopamine neuron agenesis in Nurr1-deficient mice. Sciences 1997; 276:248-250
3. Castillo S. O. Baffi J. S., Palkovits M. et al. Dopamine biosynthesis is selectively abolished in *substantia nigra/ventral tegmental area* but not in hypothalamic neurons in mice with targeted disruption of the Nurr1 gene. Mol Cell Neurosci 1998; 11:36.46
4. Iwawaki T., Kohno K., Kobayashi K. Identification of potential Nurr1 response element that activates the tyrosine hydroxylase gene promoter in cultured cells. Biochem Biophys Res Comm 2000, 274:590-595
5. Sacchetti P, Mitchell T. R., Grameman J. G., Bannon M. J. Nurr1 enhances transcription of the human dopamine transporter gene through a novel mechanism. J Neurochem 2001; 76:1565-1572
6. Le W. D., Zou L. L., Conneely O. M., et al. Selective agenesis of mesencephalic dopaminergic neurons in Nurr1 deficient mice. Exp Neurol 1999; 159; 451-458
7. Le W. D., et al. Reduced Nurr1 expression increases the vulnerability of mesencephalic dopamine neurons to MPTP-induced injury. J. Neurochem. 1999; 73:2218-2221
8. Chung S, Sonntag K C, Anderson T, Bjorklund L M, Park J J, Kim D W, Kang U J, Isacson O, Kim K S. Genetic engineering of mouse embryonic stem cells by Nurr1 enhances differentiation and maturation into dopaminergic neurons. Eur J Neurosci 2002 November; 16(10):1829-38
9. Baptist. M J, O'Farrell C, Daya S, Ahmad R, Miller D W, Hardy J, Farner M J, Cookson M R. Coordinate transcriptional regulation of dopamine synthesis genes by alpha-synuclein in human neuroblastoma cell lines. J Neurochem 2003 May; 85(4):957-68
10. Kim K S, Kim C H, Hwang D Y, Seo H, Chung S, Hong S J, Lim L K, Anderson T, Isacson O. Orphan nuclear receptor Nurr1 directly transactivates the promoter activity of the tyrosine hydroxylase gene in a cell-specific manner. J Neurochem 2003 May; 85(3):622-34
11. Kessler M A, Yang M, Gollomp K L, Jin H, Iacovitti L. The human tyrosine hydroxylase gene promoter. Brain Res Mol Brain Res 2003 Apr. 10; 112(1-2):8-23
12. Chu Y, Kompoliti K, Cochran E J, Mufson E J, Kordower J H. Age-related decreases in Nurr1 immunoreactivity in the human *substantia nigra*. J Comp Neurol 2002 Aug. 26; 450(3):203-14
13. Abayratna Wansa K S. Harris J M, Yen G, Ordentlich P, Muscat G E. The AF-1 domain of NOR-1/NR4A3 mediates trans-activation, coactivator recruitment, and activation by the purine anti-metabolite 6-Mercaptopurine. 2003 J Biol Chem April 22; [epub ahead of print]
14. Ordentlich P, Yen Y, Zhou S, Heyman R A. Identification of the anti-neoplastic agent 6-mercaptopurine as an activator of the orphan nuclear hormone receptor Nurr1, 20033 J Biol Chem April 22 [epub ahead of print]
15. Satoh J, Kuroda Y. The constitutive and inducible expression of Nurr1, a key regulator of dopaminergic neuronal differentiation, in human neural and non-neural cell lines. Neuropathology 2002 December; 22(4):219-32
16. Maira M, Martens C, Batsche E, Grauthier Y, Drouin J. Dimer-specific potentiation of NGF1-B (Nur77) transcriptional activity by the protein kinase A pathway and AF-1-dependent coactivator recruitment. Mol Cell Biol 2003 February; 23(3):763-76

17. Fells, J. B. The control of dopamine neuron development, function and survival: insights from transgenic mice and the relevance to human disease. Curr Med Chem 2003 May; 10(10):857-70
18. Iwayama-Shigeno Y, Yamada K, Toyota T, Shimizu H, Hattori E, Yoshitsugu K, Fujisawa T, Yoshida Y, Kobayashi T, Toru M, Kurumaji A, Detera-Wadleigh S, Yoshikawa T. Distribution of haplotypes derived from three common variants of the NR4A2 gene in Japanese patients with schizophrenia. Am J Med Genet 2003 Apr. 1; 118B(1):20-4
19. McEvoy A N, Murphy E A, Ponnio T, Conneely O M, Bresnihan B, FitzGerald O, Murphy, E P. Activation of nuclear orphan receptor NURR1 transcription by NF-kappa B and cyclic adenosine 5'-monophosphate response element-binding protein in rheumatoid arthritis synovial tissue. J Immunol 2002 Mar. 15; 168(6):2979-37
20. Xu P Y, Liag R, Jankovic J, Hunter C, Zeng Y X, Ashizawa T, Lai D, Le W D. Association of homozygous 7048G7049 variant in the intron six of Nurr1 gene with Parkinson's disease. Neurology 2002 Mar. 26; 58(6):881-4
21. Bannon M J. Pruetz B, Manning-Bog A B, Whitty C J, Michelhaugh S K, Sacchetti P, Granneuman J G, Mash D C, Schmidt C J. Decreased expression of the transcription factor NURR1 in dopamine neurons of cocaine abusers. Proc Natl Acad Sci USA 2002 Apr. 30; 99(9):6382-5
22. Saucedo-Cardenas O, Quintana-Hau J D, Le W D, et al. Nurr1 is essential for the induction of the dopaminergic phenotype and the survival of ventral mesencephalic late dopaminergic precursor neurons. PANS USA. 1998; 95:4013-4018
23. Zetterstrom R. H., Solomin L., Jansson L., et al. Dopamine neuron agenesis in Nurr1-deficient mice. Sciences 1997; 276:248-250
24. Castillo S. O. Baffi J. S., Palkovits M. et al. Dopamine biosynthesis is selectively abolished in *substantia nigra*/ventral tegmental area but not in hypothalamic neurons in mice with targeted disruption of the Nurr1 gene. Mol Cell Neurosci 1998; 11:36-46
25. Iwawaki T., Kohno K., Kobayashi K. Identification of potential Nurr1 response element that activates the tyrosine hydroxylase gene promoter in cultured cells. Biochem Biophys Res Comm 2000; 274:590-595
26. Sacchetti P, Mitchell T. R., Grameman J. G., Bannon M. J. Nurr1 enhances transcription of the human dopamine transporter gene through a novel mechanism. J Neurochem 2001; 76:1565-1572
27. Le W. D, Zou L. L., Conneely O. M., et al. Selective agenesis of mesencephalic dopaminergic neurons in Nurr1 deficient mice. Exp Neurol 1999; 159; 451-458
28. Le W. D., et al. Reduced Nurr1 expression increases the vulnerability of mesencephalic dopamine neurons to MPTP-induced injury. J. Neurochem. 1999; 73:2218-2221
29. Kang U J, Lee W Y, Chang J W. Gene therapy for Parkinson's disease: determining the genes necessary for optimal dopamine replacement in rat models. Hum. Cell. 2001 March; 4(1):39-48.
30. Guttman M., Stewart D., Hussey D., Wilson A., Houle S., Kish S. Influence of L-dopa on striatal dopamine transporter in early PD. 2001; Neurology 56(11): 1559-64.
31. Torstenson R., Hartvig P., Langstrom B., Westerberg G., Tedroff J. Differential effects of levodopa on dopaminergic function in early and advanced Parkinson's disease. Ann. Neurol. 1997; 41(3): 334-40.
32. Reveron M E, Savelieva K Y, Tillerson J L, McCormack A L, Di Monte D A, Miller G W. L-DOPA does not cause neurotoxicity in VMAT2 heterozygous knockout mice. Neurotoxicity 2002 23 (4-5): 611-9.
33. Gulley, J M, Doolen, S., Zahniser, N R. Brief, repeated exposure to substrates down-regulates dopamine transporter function in *Xenopus oocytes* in vitro and rat dorsal striatum in vivo. 2002; J. Neurochem. 83 (2): 400-11.
34. Hu G, Jin G Z. (−)-Stepholidine antagonizes the inhibition by D2 receptor agonists on synaptosomal tyrosine hydroxylase in rat corpus striatum. Zhongguo Yao Li Xue Bao. 1995 16(4): 376-9.
35. Meloni R., Gale, K. Pharmacological evidence for feedback regulation of dopamine metabolism in solid fetal *substantia nigra* transplants. J Pharmacol Exp Ther. 1990 253 (3):1259-64.
36. Takeuchi Y., Fukunaga K. Differential regulation of NF-kappa B, SRE and CRE by dopamine D1 and D2 receptors in transfected NG 108-15 cells. J. Neurochem. 1003 35(3): 729-39.
37. Kuhn K, Wellen J, Link N, Maskri L, Lubbert H, Stichel C C. The mouse MPTP model: Gene expression changes in dopaminergic neurons. Eur. J. Neurosci. 2003, 17(1): 1-12.
38. Tillerson J L, Caudle W M, Reveron M E, Miler G W. Detection of behavioral impairments correlated to neurochemical deficits in mice treated with moderate doses of 1-methyl-4-phenyl-1,2,3,6-tetrahydropyridine. Exp. Neurol. 2002, 178(1): 80-90.
39. D'Astous M, Morissette M, Tanguay B, Callier S, Di Paolo T. Dehydroepiandrosterone (DHEA) such as 17beta-estradiol prevents MPTP-induced dopamine depletion in mice. 258 Synapse 2002 47(1): 10-14.

CITATIONS MADE IN THE BACKGROUND, DETAILED DESCRIPTION AND EXAMPLES 1-16

Alexander, N., Yoneda, S. Vlachakis, N. D. and R. F. Maronde. 1994. Role of conjugation and red blood cells for inactivation of circulating catecholamines. Am. J. Physiol. 247 (1): R203-R207.
Alvarado, F. and R. K. Crane. 1960. Florizin as a competitive inhibitor of the active transport of sugars by hamster small intestine, in vitro. Biochim. Biophys. Acta 56: 170-172.
Arita, H. and J. Kawanami. 1980. Studies on uptake of phenyl glycosides as inhibitors of D-glucose uptake by Rhesus monkey kidney calls. J. Biochem. 88: 1399-1406.
Barnett, J. E. G., Holman, G. D. and K. A. Munday. 1973. Structural requirements for binding to the sugar transport system of the human erythrocyte. Biochem. J. 131: 211-221.
Barnett, A., McQuade, R. D. and C. Tedford. 1992. Highlights of D1 dopamine receptor antagonist research. Neurochem. Int. 20 (Suppl.): 119S-122S.
Bencsics, A., Sershen. H., Baranyi, M., Hashim, A., Lajtha, A. and E. S. Vizi. 1997, dopamine, as well as norepinephrine, is a link between noradrenergic nerve terminals and splenocytes. Brain Res. 761 (2): 236-243.
Berger, J. G., Chang, W. K., Clader, J. W., Hou, D., Chipkin, R. E. and A. T. McPhail. 1989. Synthesis and receptor affinities of some conformationally restricted analogues of the dopamine D, selective ligand (5R)-8-chloro-2,3,4,5-tetrahydro-3-methyl-5-phenyl-1H-3-benzazepin-7-ol. J. Med. Chem. 32: 1913-1921.
Brewster, W. K., Nichols, D. E., Riggs, R. M., Mottola, D. M., Lovenberg., t. W., Lewis, M. H. and R. B. Mailman. 1990, trans-10,11-dihydroxy-5,6,7,8,12b-hexahydrobenzo[a] pehnanthridine: A highly potent selective dopamine $D_1$ full agonist. J. Med. Chem. 33: 1756-1764.
Bodor et al. 1978. J. Pharm. Sci, 67 (5): 685.

Bodor, 1976. "Novel Approaches for the Design of Membrane Transport Properties of Drugs". In: "Design of Biopharmaceutical Properties Through Prodrugs and Analogs", Ed. E. B. Roche et al. APhA Academy of Pharmaceutical Sciences, Washington, D.C., pp. 98-135

Bodor et al, 1981. Science 214: 1370-1372.

Bodor et al, 1983. Pharmacology and Therapeutics 19 (3): 337-336.

Casagrande, C., Santagelo, F., Saini, C., Doggi, F., Gerli, F. and C. Cerri. 1986. Synthesis and chemical properties of Ibopamine and of related esters of N-substituted dopamines: Synthesis of Ibopamine metabolites. Arzneim. Forsch. 36 (2a): 291-303.

Chen, N., Ferrer, J. V., Havitch, J. A. and J. B. Justice. 2000. Transport-dependent accessibility or a cytoplasmic loop cysteine in human dopamine transporter. J. Biol. Chem. 275(3): 1608-1614.

Choi, S. W., Elmaleh. D. R. Hanson, R. N. and A. J. Fishman. 2000. Novel 3amilnomethyl- and 4aminopiperidine analogues of 1-[2-(diphenylmethoxy)ethyl]-4-(3-phenylpropyl)piperazines: Synthesis and evaluation as dopamine transporter ligands. J. Med. Chem. 43 (2): 205-213.

Clarkson, E. D., Edwards-Prasad, J., Freed, C. R. and K. N. Prasad. 1999. Immortalized dopamine neurons: A model to study neurotoxicity and neuroprotection. Proc. Soc. Exp. Biol. Med. 222 (2): 157-163.

Claustre, J. Pequignot, J. M., Bui-Xuan, B., Muchada. R., Cottet-Emard, R. M. and L. Peyrin. 1990. Conjugation and deamination of circulating dopamine: Relationship between sulfated and free dopamine in man. J. Auton, Nerv. Syst. 29 (2): 175-182.

Coffey, L. L. and M. Reith. 1994. [$^3$H]WIN 35,428 binding to the dopamine uptake carrier. I. Effect of tonicity and buffer composition. J. Neurosci. Methods 51 (1): 23-30.

Daily D, Vlamis-Gardikas A, Offen D, Mittelman L, Melamed E, Holmgren A, Barzilai A. Glutaredoxin protects cerebellar granule neurons from dopamine-induced apoptosis by activating NF-kappa B via Ref-1. J Biol Chem. 2001 Jun. 12; 276(2):1335-44.

Daily D, Vlamis-Gardikas A, Offen D, Mittelman L, Melamed E, Holmgren A, Barzilai A. Glutaredoxin protects cerebellar granule neurons from dopamine-induced apoptosis by dual activation of the ras-phosphoinositide 3-kinase and jun n-terminal kinase pathways. J Biol Chem. 2001 Jun. 15; 276(24):21618-26. Epub 2001 Apr. 4.

Dandrige, P. A., Kaiser, C., Brenner, M., Gaitanopoulos, D., Davis, L. D., Webb, R. L., Foley, J. J. and H. M. Sarau. 1984. J. Med. Chem. 27: 28.

Diez-Sampedro, A., Urdaneta, E., Lostao, M. P. and A. Barber. 1999. Galactose transport inhibition by cytochalasin E in rat intestine in vitro. Can. J. Physiol. Pharmacol. 77 (2): 96-101.

Duport, S. Robert, F., Muller, D., Grau, G., Parisi, L. and L. Stoppini. 1998. An in vitro blood-brain barrier model: Cocultures between endothelial cells and organotypic brain slice cultures. Proc. Natl. Acad. Sci. USA 95 (4): 1340-1345.

Earles, C. and J. O. Shenk, 1999. Multisubstrate mechanism for the inward transport of dopamine by the human dopamine transporter expressed in HEK cells and is inhibition by cocaine. Synapse 33 (3): 230-231.

Figlewicz, D. P. 1999. Endocrine regulation of neurotransmitter transporters. Epilepsy Res. 37 (3): 203-210.

Findlay, J., Levy, G. A. and C. A. Marsh. 1958. Inhibition of glycosidases by aldonolactones or corresponding configuration. 2. Inhibitors of β-N-acetylglucosaminidase. Biochemical J. 69: 467-476.

Fischer, Y., Thomas, Y., Kamp, J., Juengling, E. Rose, H., Carpen, C. and H. Kammermeier. 1995, 5-Hydroxytryptamine stimulates glucose transport in cardiomyocytes via a monoamine oxidase-dependent reaction. Biochem. J. 311 (2): 575-583.

Fodor at al. 1961. Acts Chim. Aced. Sci. Hung. 28 (4): 409.

Freeman, H. S. and J. D. McDermed. 1982. In: Chemical Regulation of Biological Mechanisms. Eds., Crieghton, A. M. and S. Turner. Royal Soc. Chemistry, London, pp 154-165.

Gainetdinov, R. R., Jones, S. R. and M. G. Caron. 1999. Functional hyperdopaminergia in dopamine transporter knock-out mice. Biol. Psychiatry 46 (3): 303-311.

Gee, J. M., DuPont, M. S., Rhodes, M. J. and I. T. Johnson. 199. Quercetin glucosides interact with the Intestinal glucose transporter pathway. Free Radic. Biol. Med. 25 (1): 19-25.

Gerding, T. K., Drenth, B. F. H., DeZeeuw, R. A., Topper, P. G. and A. S. Horn. 1990. Metabolism and disposition of the dopamine agonist 2-(N-propyl-N-2-thienylethylamino)-5_hydroxytetraline in conscious monkeys after subsequent iv, oral and ocular administration. Drug. Matab. Dispos. 18(6): 923-928.

Geurts, M., Hermans, E. and J. M. Maloteaux. 1999. Assessment of striatal D1 and D2 dopamine receptor-G protein coupling by agonist-induced [$^{35}$S]GTP gamma S binding. Life Sci. 65 (16): 1633-1645.

Giros, B., el Mestikawy, S., Bertrand, L. and M. G. Caron. 1991. Cloning and functional characterization of a cocaine-sensitive dopamine transporter. FEBS Lett. 295: 149-154.

Giros, B., el Mestikawy, S., Godinot, N., Zheng, K., Han, H., Yang-Feng, T. and M. G. Caron. 1992. Cloning, pharmacological characterization and chromosome assignment of the human dopamine transporter. Mol. Pharmacol. 42 (3): 383-390.

Green, M. D. and T. R. Tephly. 1996. Glucuronidation of amines and hydroxylated xenobiotics and endobiotics catalyzed by expressed human UGT1.4 protein. Drug Metab. Dispos. 24 (3). 356-363.

Haspel, H. C., Stephenson, K. N., Davies-Hill, T., El-Barbary, A., Lobo, J. F., Croxen, R. L., Mougrabi. W., Koehler-Stec, E. M., Fenstermacher, J. D. and I. A. Simpson. 1999. Effects of barbiturates on facilitative glucose transporters are pharmacologically specific and isoform selective. J. Membr. Biol. 169 (1): 45-53.

Hibert, M. F., Gittos, M. W., Middlemiss, D. N., Mir. A. K. and J. R. Fozard. 1988. Graphics computer-aided mapping as a predictive tool for drug design: Development of potent, selective and stereospecific ligands for the 5-HT$_{1A}$ receptor. J. Med. Chem. 31: 1087-1093.

Horton. D. 1969. Monosaccharide Amino Sugars. In: "The Amino Sugars": The Chemistry and Biology of Compounds Containing Amino Sugars. Vol. 1A. Ed. R. W. Jeanloz Academic Press, N.Y. pp. 4-18.

Hou S T, Cowan E, Walker T, Ohan N, Dove M, Rasqinha I, MacManus J P. The transcription factor E2F1 promotes dopamine-evoked neuronal apoptosis by a mechanism independent of transcriptional activation. J Neurochem. 2001 July; 78(2):287-97.

Hurtig. H. I. 1997. Problems with current treatment of Parkinson's disease. Exper. Neurol. 144: 10-16.

Husbands, S. M., Izenwasser, S., Kopajtic, T. Bowen, W. D., Vilner, B. J., Katz, J. L. and _, A. H. 1999. Structure activity relationships at the monoamine transporters as sigma receptors for a novel series of 9-[3-(cis,5-dimethyl-1-piperazinyl)propyl]carbazole (micazole) analogues. J. Med. Chem. 42 (21): 4446-4455.

Hyson, D. H., Thomson, A. B. and C. T. Kappagoda. 1996. Calcium channel blockers modify jejunal uptake of D-galactose in rabbits. Dig. Dis. Sci. 41(9): 1871-1875.

Hyson. D. H., Thomson, A. B., Keelan, M. and C. T. Kappagoda. 1997. A high cholesterol diet blocks the effect of calcium channel blockers on the uptake of sugars in rabbit intestine. Can. J. Physiol. Pharmacol. 75 (1); 57-64.

Iorio, L. C., Barnett, A., Billard, W. and E. H. Gold. 1986. Benzazepines structure-activity relationships between $D_1$ receptor blockade and selected pharmacological effect. In: Neurobiology of Central D1 Dopamine Receptors, Eds., G. R. Breese and I. Creese, Plenum Press, NY. pp. 1-14.

Jaber, M., Dumartin, B. Sagne, C., Haycock, J. W., Roubert, C., Giros, B., Bloch, B. and M. G. Caron. 1999. Differential regulation of tyrosine hydroxylase in the basal ganglion of micro lacking the dopamine transporter. Eur. J. Neurosci. 11 (10): 3499-3511.

Jones, S. R., Joseph, J. D., Barak, L. S., Caron, M. G. and R. M. Wightman. 1999. Dopamine neuronal transport kinetics and effects of amphetamine. J. Neurochem. 73 (6): 2406-2414.

Jork, R., Lossner, B. and H. Matthies. 1980. The influence of dopamine on the incorporation of different sugars into total proteins of hippocampal slices. Pharmacol. Biochem. Behav. 13 (2): 303-304.

Kaiser, C., Dandridge, P. A., Garvey, E., Hahn, R. A., Sarau H. M., Setler, P. E., Bass, L. S. and J. Clardy. 1982. J. Med. Chem. 25: 697.

Kawasaki, H. and M. Yago. 1983. The identification of two N-acyldopamine glucosides in the left colleterial gland of the praying mantid, *Tenodera aridifolla sinensis* Saussure, and their role in the cothecal sclerotization. Insect Biochem. 13: 267-271.

Kerwin, J. L. 1996. Negative ion electrospray mass spectrometry of polyphenols, catecholamines and their oxidation products. J. Mass Sprectrom. 31:1429-1439.

Kerwin, J. L. 1997. Profiling peptide adducts of oxidized N-acetyldopamine by electrospray mass spectrometry. Rapid Commun. Mass Sprectrom. 11: 557-566.

Kilbourn, M. R., Kuszpit, K. and P. Sherman. 2000. Rapid and differential losses of in vivo dopamine transporter (DAT) and vesicular monoamine transporter (VMAT2) radioligand binding in MPTP-treated mice. Synapse 35 (4): 250-255.

Kilty, J. E., Lorang, D. and S. G. Amara. 1991. Cloning and expression of a cocaine-sensitive rat dopamine transporter. Science 254 (5031): 578-579.

Knoerzer, T. A., Nichols, D. E., Brewster, W. K., Watts, V. J., Mottola, D and R. B. Mailman. 1994. Dopaminergic benzo[a]phenanthridines: Resolution and pharmacological evaluation of the enantiomers of dihydrexidine, the full efficacy D, dopamine receptor agonist. J. Mad. Chem. 37: 2453-2460.

Kuchel, O. 1999. Peripheral dopamine in hypertension and associated conditions. J. Hum. Hypertens. 13 (9); 605-615.

Kuipers, W., Duse, C. G., van Wijngaarden. I., Standaar, P. J., Martin, T. M., Tulp, N. V., Spek, A. L. and A. P. Ijzerman. 1997, 5-$HT_{1A}$ vs. $D_2$-receptor selectivity of Flesinoxan and analogous $N^4$-substituted and $N^1$-arylpiperazines. J. Med. Chem. 40: 300-312.

Kumagai, A. K. 1999. Glucose transport in brain and retina: Implications in the management and complications of diabetes. Diabetes Metab. Res. Rev. 15 (4): 261-273.

Leal, M., Hayes, M. J. and M. L. Powell. 1992. The metabolism of CGS15873 in man using stable isotope pattern recognition techniques. Biopharm. Drug Dispos. 13 (3): 617-628.

Lichtenthaler, F. W. Efficient Reaction Channels from Mono- and Disaccharides to Enantiopure Building Blocks and Exploitation of Their Application Profiles. In: Carbohydrates: Synthetic Methods and Applications in Medicinal Chemistry, edited by Ogura. H., Hasegawa, A., and Suami, T. Tokyo:Kodansha, 1992, p. 3-27.

Liljefors, T. and H. Wikstrom. 1986. J. Med. Chem. 29:1896.

van de Waterbeemd, V., Tayer, N. E. Testa, B., Wikstrom, H. and B. Largent. 1987. J. Med. Chum. 30: 2175.

Lostao, M. P., Urdaneta. E., Martinez-Anso, E., Barber, A. and J. A. Martinez. 1998. Presence of leptin receptors in rat small intestine and leptin effect on sugar absorption. FEBS Lett. 423 (3): 302-306.

Loland, C. J., Norregaard, L. and U. Gether. 1999. Defining proximity relationships in the tertiary structure of the dopamine transporter. Identification of a conserved glutamic acid third coordinate in the endogenous $Zn^{2+}$ binding site. J. Biol. Chem. 274:36928-36934.

Luo Y, Hattori A, Munoz J, Qin Z H, Roth G S. Intrastriatal dopamine injection induces apoptosis through oxidation-involved activation of transcription factors AP-1 and NF-kappaB in rats. Mol Pharmacol. 1999 August; 56(2):254-64.

Manzi, A. E. and A. Varki. 1993. In: Glycobiology: A Practical Approach. Eds. M. Fukuda and A. Kobata. IRL Press, Oxford University, Oxford. pp 29-31.

Martin, M. G., Turk, E., Lostao, M. P., Kerner, C. ad E. M. Wright. 1996. Defects in Na+/glucose cotransporter (SGLT1) trafficking and function cause glucose-galactose malabsorption. Nat. Genet. 12 (2): 216-220.

Maltiuz, E., Freankin. R., Gillespie, T., Murphy, A., Bernstein, J. Chiur, A., Hotten, T. and K. Kassahun. 1997. Disposition and metabolism of olanzapine in mice, dogs and rhesus monkeys. Drug Metab. Dispos. 25 (5): 573-593.

McDcrmod, J. D., Freeman, H. S. and R. M. Ferris. 1978. Enantioselective binding of (+) ad (−) 2-amino-6,7-dihydroxy-1,2,3-tetrahydronaphythalenes and related agonists to dopamine receptors. In: Catecholamines: Basic and Clinical Fronteins, Eds., E. Usdin, I. J. Kopin ad J. Barchas, Pergamon Press, NY. pp 568-570.

Meyer, W., Buehring, K. U., Steiner, K., Ungethum, W. and E. Schnurr. 1992. Pharmacokinetics and first clinical experiences with an antihypertensive dopamine (DA2) agonist. Eur. Heart J. 13 (Suppl. D): 121-128.

Mico, B. A., Swagzdis, J. E., Federowicz, D. A. aid K. Straub. 1966. Function-group metabolism of dopamine-2 agonists: Conversion of 4-(2-di-N-propylaminoethyl)-2-($^3$H)-indolone to 4-(2-di-N-propylaminoethyl)-7-hydroxyl-2-($^3$H)-indolone. J. Pharm. Sci. 75 (10): 929-933.

Melikian, H. E. and K. M. Buckley. 1999. Membrane trafficking regulates the activity of the human dopamine transporter. J. Neurosci. 19 (18): 7699-7710.

Miller, G. W., Gainetdinov, R. R., Levey, A. I. and M. G. Caron. 1999. Dopamine transporters and neuronal injury. Trends Pharmacol. Sci. 20(10): 424-429.

Minor, D. L., Wyrick, S. D., Charifson, P. S. Watts, V. J., Nichols, D. E. and R. B. Mailman. 1994. Synthesis and molecular modeling of 1-phenyl-1,2,3,4-tetrahydroisoquinolines and related 5,6,8,9-tetrahydro-13bH-dibenzo[a,h]quinolizines D1 dopamine antagonists. J. Med. Chem. 37: 4317-4328

Mizuma, T., Ohta, K. and S. Awazu. 1994. The beta-anomeric and glucose preferences of glucose transport carrier for intestinal active absorption of monosaccharide conjugates. Biochim. Biophys. Acts 1200 (2): 117-122.

Mizuma, T., Ohta. K., Hayashi, M. and S. Awazu. 1992. Intestinal active absorption of sugar-conjugated compounds by glucose transport system: Implications for improvement of poorly absorbable drugs. Biochem. Pharmacol. 43: 2037-2039.

Mizuma, T., Ohta. K., Hayashi, M. and S. Awazu. 1993. Comparative study of active absorption by the intestine and disposition of anomers of sugar-conjugated compounds. Biochem. Pharmacol. 45 (7): 1520-1523.

Morgan, T. D., Hopkins, T. L., Kramer, K. J., Roseland, C. R., Czapaia, T. H., Tomer, K. B. and Crow, F. W. 1987. N-β-Alanylnorepinephrine: Biosynthesis in insect cuticle and possible role in sclerotization. Insect Biochem. 37:255-263.

Morgan, M. J. and K. B. Franklin. 1991. Dopamine receptor subtypes and formalin test analgesia. Pharmacol. Biochem. Behav. 40 (2): 317-322.

Mueller, D. D., Morgan, T. D., Wassenberg, J. D., Hopkins, T. L. and K. J. Kramer. 1993, 1H and 13C NMR of 3-O and 4-O conjugates of dopamine and other catecholamines. Bioconjug. Chem. 4(1): 47-53.

Navarro, H., Arruebo, M. P., Alcalde, A. I. and V. Sorribas. 1993. Effect of erythromycin on D-galactose absorption and sucrase activity in rabbit jejunum. Can. J. Physiol. Pharmacol. 71 (3-4): 191-194.

Panet H, Barzilai A, Daily D, Melamed E, Offen D. Activation of nuclear transcription factor kappa B (NF-kappaB) is essential for dopamine-induced apoptosis in PC12 cells. J Neurochem. 2001 April; 77(2):391-8.

Petersson, I., Liljefors, T. and K. Bogeso. 1990. Conformational analysis and structure-activity relationships of selective dopamine $D_1$ receptor agonists and antagonists of the benzazepine series. J. Med. Chem. 33: 2197-2204.

Pokorski, M. and Z. Matysiak. 1998. Fatty acid acylation of dopamine in the carotid body. Med. Hypothesis. 50 (2): 131-133.

Pocchiari, F., Pataccini, R., Casteinovo, P., Longo, A. and C. Casagrande. 1986. Ibopamine, an orally active dopamine-like drug: Metabolism and pharmacokinetics in rats. Arzneim.-Forsch. 36 (2A): 334-340.

Prakash, C., Cui, D., Baxter, J. G., Bright, G. M., Micell, J. and K. Wilner. 1998. Metabolism and excretion of a new anxiolytic drug candidate, CP-93,393, in healthy male volunteers. Drug Matab. Dispos. 26 (5): 448-456.

Prakash, K. R., Tamiz, A. P., Araldi, G. L., Zhang, M., Johnson, K. M. and A. Kozikowski. 1999. N-phenylalkyl-substituted tropate analogs of boat conformation of high selectivity for the dopamine versa serotonin transporter. Bioorg. Med. Chem. Lett. 9 (23): 3325-3328.

Rabinovic A D, Lewis D A, Hastings T G. Role of oxidative changes in the degeneration of dopamine terminals after injection of neurotoxic levels of dopamine. Neuroscience. 2000; 101(1):67-76.

Ramaswamy, K., Bhattacharyya, B. R. and R. K. Crane. 1976, 1-O-acyl derivatives of glucose as non-penetrating inhibitors of glucose transport by hamster small intestine in vitro. Biochim. Biophys. Acta 443: 284-287.

Reveron M E, Savelieva K Y. Tillerson J L, McCormack A L, Di Monte D A, Miller G W. L-DOPA does not cause neurotoxicity in VMAT2 heterozygote knockout mice. Neurotoxicology. 2002 October; 23(4-5):611-9.

Rhoads, D. B., Rosenbaum, D. H., Unsal, H., Isselbacher, K. J. and L. L. Levitsky. 1991. Circadian periodicity of intestinal Na+/glucose cotransporter I mRNA levels is transcriptionally regulated. J. Biol. Chem. 273 (16): 9510-9516.

Riggs, M. R., Nichols, D. E., Foreman, M. M., Truex, L. L., Glock, D. and J. D. Kohli. 1987. J. Med. Chem. 30: 1454.

Schauer, R. 1978. In: Methods in Enzymology, Ed. V. Ginsberg. Academic Press, NY. pp. 64-89.

Seiler, M. P. and R. Markstein. 1982. Mol. Pharmacol. 22: 281.

Seiler, M. P. and R. Markstein. 1989. J. Mol. Pharmacol. 35: 643.

Seiler, M. P., Hagenbach, A., Wuthrich, H-J. and R. Markstein. 1991, trans-Hexahydroindolo[4,3-ab]phenanthridines ("Benzergolines"), the first structural class of potent and selective D1 receptor agonists lacking a catechol group. J. Med. Chem. 34 (1): 303-307.

Shimada, S., Kitayama, S., Lin, C. L., Patel, A., Nanthakumar E., Gregor, P., Kuhar, M. and G. Uhl. 1991. Cloning and expression of a cocaine-sensitive dopamine transporter complementary DNA. Science 254 (5031): 576-578.

Shindo, H., Komai, T. and K. Kawai. 1973. Metabolism of D- and L-isomers of 3,4 dihydroxyphenylalanine (DOPA). V. Mechanism of intestinal absorption of carbon-14 labeled D- and L-dopa in rats. Chem. Pharm. Bull 21 (9): 2031-2038.

Shah, J. H., Kline, R. H., Geter-Douglass, B., Izenwasser, S., Witkin, J. M. and A. H. Newman. 1996. (+/−)-3-[4'-(N,N-dimethylamino)cinnamyl]benzazepine analogs: Novel dopamine $D_1$ receptor antagonists. J. Med. Chem. 39:3423-3428.

Snyder, S. E., Aviles-Garay, F. A., Chakraborti, R., Nichols, D. E., Watts, V. J. and R. B. Mailman. 1995. Synthesis and evaluation of 6,7-dihydroxy-2,3,4,8,9,13b-hexahydro-1H-benzo[6,7]cycloheptal [1,2,3ef][3]benzazepine, 6,7-dihydroxy-2,3,4,8,9,12b-hexahydroanthra-[10,4a,4-c,d] azepine and 10-(aminomethyl)-9,10-dihydro-1,2-dihyroxyanthracene as conformationally restricted analogs of β-phenyldopamine. J. Med. Chem. 38: 2395-2409.

Storch, A., Ludolph, A. C. and J. Schwarz 1999. HEK-293 cells expressing the human dopamine transporter are susceptible to low concentrations of 1-methyl-4-phenylpuridine acting via impairment of energy metabolism. Neurochem. Int. 35 (5): 393-403.

Sugamori, K. S., Lee, F. J., Pristupa, Z. B. and H. B. Niznik. 1999. A cognate dopamine transporter-like activity endogenously expressed in a COS-7 kidney derived cell line. FEBS Let. 451 (2): 169-174.

Takata, K., H. Hirano and M. Kasahara. 1997. Transport of glucose across the blood-tissue barriers. Int. Rev. Cytology 172: 1-53.

Umegae, Y., H. Nohta and Y. Ohkura. 1988. Anal. Chim. Acta 208: 59.

Vandenbergh, D. J., Persico, A. M. and G. R. Uhl. 1992. A human dopamine transporter cDNA predicts reduced glycosylation, displays a novel repetitive element and provides radically-dimorphic TaqI RFLPs. Brain Res. Mol. Brain Res. 15 (1-2): 161-166.

Vannucci, S. J., Clark, R. R., Koehler-Stec. E., Li, K., Smith, C. B., Davies, P., Maher, F. and I. A. Simpson. 1998. Glucose transporter expression in brain: Relationship to cerebral glucose utilization. Dev. Neurosci. 20 (4-5): 369-379.

Verhoeff N. P. 1999. Radiotracer imaging of dopaminergic transmission in neuropsychiatric disorders. Psychopharmacol. (Berl) 147 (3): 217-249.

Wang, P. C., Nguyen, T. B., Kuchel, O. and J. Genest. 1983. Conjugation patterns of endogenous plasma catecholamines in human and rat. J. Lab. Clin. Med. 101 (1): 141-451.

Wang, P. C., Kuchel, O., Buu, N. T. and J. Genest. 1983. Cathecholamine glucuronidation: An important metabolic pathway for dopamine in the rat. J. Neurochem. 40 (5): 1435-1440.

Weingarten P, Bermak J, Zhou Q Y. Evidence for non-oxidative dopamine cytotoxicity: potent activation of NF-kappa B and lack of protection by anti-oxidants. J Neurochem. 2001 March; 76(6):1794-804.

Weinstock, J., Hieble, J. P. and J. W. Wilson. 1985. Drugs Future 10: 645.

Whitfield, C. F., Rannels, S. R. and H. E. Morgan. 1974. Acceleration of sugar transport in avian erythrocytes by catecholamines. J. Biol. Chem. 249 (13): 4181-4188.

Wright, E. M., Hirsch, J. R., Loo, D. D. and G. A. Zampighi. 1997. Regulation of Na+/glucose cotransporters. J. Exp. Biol. 200 (2): 287-293.

Wu, X. and H. H. Gu. 1999. Molecular cloning of the mouse dopamine transporter and pharmacological comparison with the human homologues. Gene 233 (3): 163-170.

Xia X G, Schmidt N, Teismann P, Ferger B, Schulz J B. Dopamine mediates striatal malonate toxicity vie dopamine transporter-dependent generation of reactive oxygen species and D2 but not D1 receptor activation. J Neurochem. 2001 October; 79(1):63 70.

While the preferred embodiment of the invention has been illustrated and described, it will be appreciated that various changes can be made therein without departing from the spirit and scope of the invention.

I claim:

1. A pharmaceutical composition comprising
an agent selected from the group consisting of an additive, a stabilizer, a carrier, a binder, a buffer, an excipient, an emollient, a disintegrant, a lubricating agent, an antimicrobial agent and a preservative and
a compound having the formula:

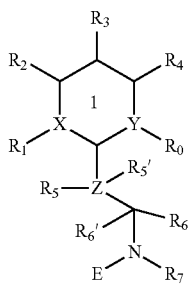

wherein:
Ring 1 is a substituted aryl ring;
X and Y are carbon atoms;
$R_0$ is hydrogen;
$R_3$ is hydroxyl;
N is the nitrogen atom of an amine or an amide;
$R_1$, $R_4$, $R_5$, $R_{5'}$, $R_6$, $R_{6'}$ and $R_7$ are hydrogen,
$R_2$ is hydroxyl,
z is a carbon atom,
E is a residue of a straight chain hexose sugar,
or a pharmaceutically acceptable salt thereof.

2. The pharmaceutical composition of claim 1, wherein E is a sugar residue having a structure:

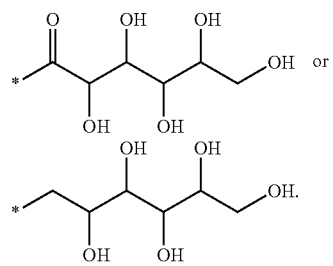

3. A pharmaceutical composition comprising
an agent selected from the group consisting of an additive, a stabilizer, a carrier, a binder, a buffer, an excipient, an emollient, a disintegrant, a lubricating agent, an antimicrobial agent and a preservative and
a dopamine ribonamide or a pharmaceutically acceptable salt thereof.

4. A pharmaceutical composition comprising
an agent selected from the group consisting of an additive, a stabilizer, a carrier, a binder, a buffer, an excipient, an emollient, a disintegrant, a lubricating agent, an antimicrobial agent and a preservative and
a dopamine amide, wherein the dopamine amide is produced by a process comprising:
a) reacting a lactone of a sugar and 3-hydroxytyramine, and
b) collecting the dopamine amide,
wherein the reaction yields a sugar residue having a structure:

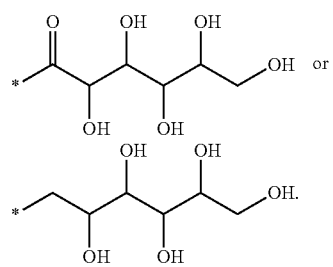

5. A process for preparing the pharmaceutical composition of claim 1, comprising:
reacting a lactone of a sugar and an optionally substituted phenethylamine, and
collecting the phenethylamide.

6. A process of preparing the pharmaceutical composition of claim 4, comprising
reacting a lactone of a sugar and 3-hydroxytyramine, and collecting the dopamine amide.

7. A method of ameliorating Parkinson's Disease in a subject in need thereof comprising administering to the subject the pharmaceutical composition of claim 1.

8. A method for ameliorating Parkinson's Disease in a subject in need thereof, comprising administering to the subject a pharmaceutical composition of claim 3.

9. A method for ameliorating Parkinson's Disease in a subject in need thereof, comprising administering to the subject a pharmaceutical composition of claim 4.

* * * * *